US007419660B1

(12) United States Patent
Denney, Jr.

(10) Patent No.: US 7,419,660 B1
(45) Date of Patent: Sep. 2, 2008

(54) VACCINES FOR TREATMENT OF LYMPHOMA AND LEUKEMIA

(75) Inventor: Dan W. Denney, Jr., Redwood City, CA (US)

(73) Assignee: Genitope Corporation, Fremont, CA (US)

(*) Notice: Subject to any disclaimer, the term of this patent is extended or adjusted under 35 U.S.C. 154(b) by 0 days.

(21) Appl. No.: 09/370,453

(22) Filed: Aug. 9, 1999

Related U.S. Application Data

(60) Division of application No. 08/761,277, filed on Dec. 6, 1996, now Pat. No. 5,972,334, and a continuation-in-part of application No. 08/644,664, filed on May 1, 1996, now Pat. No. 5,776,746.

(51) Int. Cl.
*C12N 5/06* (2006.01)
*C12N 5/10* (2006.01)
*A61K 39/00* (2006.01)

(52) U.S. Cl. .............. 424/93.21; 424/93.71; 424/277.1; 435/326

(58) Field of Classification Search .............. 424/130.1, 424/141.1, 131.1, 184.1; 435/68.1, 343.1, 435/320.1, 327, 325, 326, 372.3, 69.1; 536/23.53
See application file for complete search history.

(56) References Cited

U.S. PATENT DOCUMENTS

| | | | | |
|---|---|---|---|---|
| 4,399,216 A | 8/1983 | Axel et al. | ...................... | 435/6 |
| 4,634,665 A | 1/1987 | Axel et al. | ..................... | 435/68 |
| 4,656,134 A | 4/1987 | Ringold | ........................ | 435/91 |
| 4,683,195 A | 7/1987 | Mullis et al. | ................... | 435/6 |
| 4,683,202 A | 7/1987 | Mullis | .......................... | 435/91 |
| 4,956,288 A | 9/1990 | Barsoum | | |
| 4,965,188 A | 10/1990 | Mullis et al. | ................... | 435/6 |
| 5,043,270 A | 8/1991 | Abrams et al. | ............. | 435/69.1 |
| 5,122,464 A | 6/1992 | Wilson et al. | ............ | 435/172.3 |
| 5,179,017 A | 1/1993 | Axel et al. | ............... | 435/240.2 |

FOREIGN PATENT DOCUMENTS

| | | |
|---|---|---|
| EP | 0 433 900 A1 | 6/1991 |
| WO | 91/13632 | 9/1991 |
| WO | 94/08601 | 4/1994 |

OTHER PUBLICATIONS

Stevenson et al (1995) Annals. New York Acad Science vol. 772: pp. 212-226.*
Tao et al Nature (1993) vol. 362 pp. 755-758.*
Fundamentals of Immunology Ed Bell Paul. Chapter 38 p. 1060-1061; 1066-1067.*
Evans et al (QJM Jun. 1999;92(6):299-307).*
De The G (Blood Cells 1993;19(3):667-73;discussion 674-5).*
Chen TT et al (J. Immunology 1994; 153:4775-4787).*
Paul WE Fundamental Immunology 3rd ed, Raven Press 1993, p. 9.*
www.hyperdictionary.com —html printout; definition of "idiotype" and "idiotope".*
Cleary et al (Cell, 1986, vol. 44, pp. 97-106).*
Levy et al (Journal of Experimental Medicine, 1988, vol. 168, pp. 475-489).*
Embleton et al (Nucleic Acids Research, 1992, vol. 20, pp. 3831-3837).*
Timmerman et al, Blood, Nov. 16, 2005.*
Leonard et al, Blood, Nov. 16, 2003, vol. 102 p. 105A.*
Leonard et al, Blood, Nov. 16, 2002, vol. 100, abstract No. 4792).*
Briones et al, Blood, Nov. 16, 2001, vol. 98, p. 608A.*
Roitt et al, Immunology (text), 1998, pp. 142-143.*
Mason, et al., *Myelin Basic Protein Peptides Complexes with the Class II MHC Molecules I-$A^u$ amd I-$A^k$ Form and Dissociate Rapidly at Neutral pH*. Journal of Immunology 154: 5216-5227 (May 15, 1995).
Sambrook, et al., *Molecular Cloning*, 16.8-16.15 (1989).
Mason-Kiemle. *Interactions of Antigenic Peptides with Class II Major Histocompatibility Molecules*, A dissertation submitted to the Program in Biophysics and the Committee on Graduate Studies of Stanford University, Submitted Jan. 1995, Deposited in Falconer Library Sep. 1995.
Walls et al., (1989) "Amplification of Muticistronic Plasmids in the Humaan 293 Cell Line and Secretion of Correctly Processed Recombinant Human—Protein C," *Gene*81:139-149.
Maniatis et al., (1987) "Regulation of Inducible and Tissue-specific Gene Expression," *Science*236:1237-1244.
Voss et al., (1986) "The Role of Enhancers in the Regulation of Cell Type-Specific Transcriptional Control," *Trends Biochem. Sci.* 11:287-289.
Dijkema et al., (1985) "Cloning and expression of the Chromosomal Immune Interferon Gene of the Rat," *EMBO J.* 4:761-767.
Uetsuki et al., (1989) "Isolation and Characterization of the Human Chromosomal Gene for Polypeptide Chain Elongation Factor-1α," *J. Biol. Chem.* 264:5791-5798.
Kim et al., (1990) "Use of the Human Elongation Factor 1α Promoter as a Versatile and Efficient Expression System," *Gene* 91:217-223.
Mizushima and Nagata, (1990) "pEF-BOS, A Powerful Mammalian Expression Vector," *Nuc. Acids. Res.*, 18:5322.
Gorman et al., (1982) "The Rous Sarcoma Virus Long Terminal Repeat is a Strong Promoter When Introduced into a Variety of Eukaryotic Cells by DNA-mediated Transfection," *Proc. Natl. Acad. Sci. USA* 79:6777-6781.
Boshart et al., (1985) "A Very Strong Enhancer is Located Upstream of an Immediate Early Gene of Human Cytomegalovirus," *Cell* 41:521-530.
Sambrook et al., (1989) *Molecular Cloning: A Laboratory Manual*, 2nd ed., Cold Spring Harbor Laboratory Press, New York pp. 16.6-16.8, 7.26-7.29, 9.16-9.23.

(Continued)

*Primary Examiner*—Karen Canella
(74) *Attorney, Agent, or Firm*—Casimir Jones, S.C.

(57) ABSTRACT

The present invention provides multivalent vaccines for the treatment of B-cell malignancies (e.g., lymphomas and leukemias). The present invention also provides methods for the production of custom vaccines, including multivalent vaccines for the treatment of immune cell tumors malignancies as well as methods of treating immune cell tumors using custom vaccines.

5 Claims, 26 Drawing Sheets

OTHER PUBLICATIONS

Schmike et al., (1978) "Gene Amplification and Drug Resistance in Cultured Murine Cells," *Science* 202:1051-1055.

Kaufman, (1990) "Selection and Coamplification of Heterologous Genes in Mammalian Cells," *Methods in Enzymol.*, 185:537-565.

Bird et al., (1988) "Single-Chain Antigen-Binding Proteins," *Science* 242:423-426.

Huston et al., (1988) "Protein engineering of antibody binding sites: Recovery of specific activity in an anti-digoxin single-chain Fv analogue produced in *Escherichia coli*," *Proc. Natl. Acad. Sci. USA* 85:5879-5883.

Bebbington et al., (1992) "High-Level Expression Of A Recombinant Antibody From Myeloma Cells Using A Glutamine Synthetase Gene As An Amplifiable Selectable Marker," *Bio/Technology* 10:169-175.

Dorai and Moore, (1987) "The Effect of Dihydrofolate Reductase-Mediated Gene Amplification on the Expression of Transfected Immunoglobulin Genes," *J. Immunol.* 139:4232-4241.

Ausubel et al., (1995) *Current Protocols in Molecular Biology*, John Wiley & Sons, Inc., at 9.31 to 9.36.

Takebe et al., (1988) "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466-472.

Graham, F.L. et al., (1977) "Characteristics of a Human Cell Line Transformed by DNA From Human Adenovirus Type 5," *J. Gen. Virol.*, 36:59-72.

Harrison, T., et al., (1977) "Host-Range Mutants of Adenovirus Type 5 Defective for Growth in HeLa Cells," *Virology* 77:319-329.

Graham, F.L. et al.,(1978) "Defective Transforming Capacity of Adenovirus Type 5 Host-Range Mutants," *Virology* 86:10-21.

Laimins et al., (1984) "Host Specific Activation of Transcription by Tandem Repeats form Simian Virus 40 and Moloney Murine Sarcoma Virus 40 and Moloney Murine Sarcoma Virus," *Proc. Natl. Acad. Sci. USA* 79:6453-6457.

Bimboim and Doly, (1979) "A Rapid Alkaline Extraction Procedure for Screening Recombinant plasmid DNA,"*Nuc. Acids. Res.*, 7:1513-1523.

Kaufman and Sharp, (1982) "Amplification and Expression of Sequences Cotransfected with a Modular Dihydrofolate Reductase Complementary DNA Gene," *J. Mol. Biol.* 159:601-621.

Kaufman et al., (1985) "Coamplification and Coexpression of Human Tissue-Type Plasminogen Activator and Murine Dihydrofolate Reductase Sequences in Chinese Hamster Ovary Cells," *Mol. Cell. Biol.* 5:1750-1759.

Toneguzzo et al., (1988) "Electric Field-Mediated Gene Transfer: Characterization of DNA Transfer and Patterns of Integration In Lymphoid Cells," *Nucl. Acid Res.* 16:5515-5532.

Calos et al., (1983) "High Mutation Frequency in DNA Transfected Into Mammalian Cells," *Proc. Natl. Acad. Sci. USA* 80:3015-3019.

Kopchick and Stacey, (1984) "Differences In Intracellular DNA Ligation After Microinjection and Transfection," *Mol. Cell. Biol.* 4:240-246.

Wake et al. (1984) "How Damaged is sThe Biologically Active subpopulation of Transfected DNA?," *Mol. Cell. Biol.* 4:387-398.

Lebkowski et al., (1984) "Transfected DNA Is Mutated in Monkey, Mouse, and Human Cells," *Mol. Cell. Biol.* 4:1951-1960.

Drinkwater and Klinedinst, (1986) "Chemically Induced Mutagenesis In A Shuttle Vector With A Low-Background Mutant Frequency," *Proc. Natl. Acad. Sci. USA* 83:3402-3406.

Rice and Baltimore, (1982) "Regulated Expression of An Immunoglobulin K Gene Introduced into a Mouse Lymphoid Cell Line," *Proc. Natl. Acad. Sci. USA* 79:7862-7865.

Oi et al., (1983) "Immunoglobulin Gene Expression in Transformed Lymphoid Cells," *Proc. Natl. Acad. Sci. USA* 80:825-829.

Potter et al., (1984) "Enhancer-Dependent Expression of Human *K* Immunoglobulin Genes Introduced Into Mouse pre-B Lymphocytes by Electroporation" *Proc. Natl. Acad. Sci. USA* 81: 7161-7165.

Boggs et al., (1986) "Efficient Transformation and Frequent Single-Site, Single-Copy Insertion of DNA Can Be Obtained in Mouse Erythroleukemia Cells Transformed by Electroporation" *Exp. Hematol.* 14:988-994.

Toneguzzo et al., (1986) "Electric Field-Mediated DNA Transfer: Transient and Stable Gene Expression in Human and Mouse Lymphoid Cells," *Mol. Cell. Biol*6:703-706.

Toneguzzo and Keating, (1986) "Stable Expression of Selectable Genes Introduced Into Human Hematopoietic Stem Cells By Electric Field-Mediated DNA Transfer," *Proc. Natl. Acad. Sci. USA* 83:3496-3499.

Chu et al., (1987) "Electroportation For The Efficient Transfection of Mammalian Cells With DNA," *Nucl. Acids Res.* 15:1311-1326.

Moore et al., (1993) "Interleukin-10," *Ann. Rev. Immunol.* 11: 165-190.

Mosmann, (1994) "Properties and Functions of Interleukin-10" *Advances in Immunol.* 56:1-26.

Bromberg, (1995) "IL-10 Immunosuppression in Transplantation," *Curr. Op. Immunol.* 7:639-643.

Sharma et al., (1991) "Antigen-Specific Therapy of Experimental Allergic Encephalomyelitis by Soluble Class II Major Histompatibility Complex-Peptide Complexes" *Proc. Natl. Acad. Sci. USA* 88:11465-11469.

Tonegawa, (1983) "Somatic generation of antibody diversity," *Nature* 302:575-581.

Teilland et al., (1984) "Monoclonal Antibodies Reveal the Structural Basis of Antibody Diversity," *Science* 222:721-726.

Griffiths et al., (1984)"Somatic mutation and the maturation of immune response to 2-phenyl oxazolone," *Nature* 312:271-275.

Clarke et al., (1985) "Inter- and Intraclonal Diversity in the Antibody Response to Influenza Hemagglutinin," *J. Exp. Med.* 161:687-704.

Cleary et al. (1986) "Clustering of Extensive Somatic Mutations in the Variable Reigon of an Immunoglobulin Heavy Chain Gene from a Human B Cell Lymphoma," *Cell* 44:97.

Levy et al. (1988) "Mutational Hot Spots in Ig V Region Genes of Human Follicular Lumphomas," *J. Exp. Med .* 168:475-489.

Bahler and Levy, (1992) "Clonal evolution of a follicular lymphoma: Evidence for antigen selection," *Proc. Natl. Acad. Sci USA* 89:6770-6774.

Zelentz et al., (1992) "Clonal Expansion in Follicular Lymphona Occurs Subsequent to Antigenic Selection," *J. Exp. Med.* 176:1137-1148.

Zhu et al., (1994) "Clonal history of a human follicular lymphoma as revealed in the immunoglobulin variable region genes," *Brit. J. Haematol.* 86:505-512.

Okayama and Berg, (1983) "A cDNA Cloning Vector That Permits Expression of cDNA Inserts in Mammalian Cells," *Mol. Cell. Biol.*, 3:280-289.

Shinnick et al., (1981) "Nucleotide Sequence of Moloney Murine Leukaemia Virus," *Nature* 293:543-548.

Allison et al., (1982) "Tumor-Specific Antigen of Murine T-Lymphoma Defined with Monoclonal Antibody," *J. Immunol.*, 129:2293-2300.

Huynh, et al., (1985) "Constructing and Screening cDNA Libraries in λgt10 and λgt1 DNA Cloning: A Practical Approach," (D.M. Glover, ed.), vol. 1, IRL Press Oxford, pp. 49-78.

Jolly et al., (1983) "Isolation and Characterization of a Full-Length Expressable cDNA for Human Hypoxanthine Phosphoribosyltransferase," *Proc. Natl. Acad. Sci. USA* 80:477-481.

Saiki et al., (1988) "Primer-Directed Enzymatic Amplification of DNA with a Thermostable DNA Polymerase," *Science* 239:487-491.

Elliott et al., (1990) "Genes for Plasmodium Falciparum Surface Antigens Cloned by Expression in COS Cells," *Proc. Natl. Acad. Sci. USA* 87:6363-6367.

Seed, (1987) "An LFA-3cDNA Encodes a Phospolipid Linked Membrane Protein Homologous To Its Receptor CD2," *Nature* 329:840-842.

Moore et al., (1990) "Homology of Cytokine Synthesis Inhibitory Factor (IL-10) To The Epstein-Barr Virus Gene BCRFI," *Science* 248:1230-1234.

Hoopes and McClure, (1988), "Studies on the Selectivity of DNA Precipitation by Spermine," *Nucleic Acids Res.* 9:5493-5504.

Caras et al., (1987) "Cloning Of Decay-Accelerating Factor Suggests Novel Use Of Splicing To Generate Two Proteins," *Nature* 325:545-548.

Caras et al., (1987) "Signal For Attachment of a Phospolipid Membrane Anchor in Decay Accelerating Factor," *Science* 238:1280-1282.

Kupke et al., (1989) "Improved Purfication and Biochemical Properties of Phosphatidylinositol-Specific Phospholipase C From Bacillus Thuringiensis" *Eur. J. Biochem.* 185:151-155.

Stetler et al., (1982)"Isolation of a cDNA Clone for the Human HLA-DR Antigen α Chain by Using a Synthetic Oligonucleotide as a Hybridization Probe," *Proc. Natl. Acad. Sci. USA* 79:5966-5970.

Kunkel et al., (1987) "Rapid and Efficient Site-Specific Mutagensis Without Phenotypic Selection," *Methods in Enzymology* 154:367-382.

Russel et al., (1986) "An Improved Filamentous Helper Phage for Generating Single-Stranded Plasmid DNA," *Gene* 45:333-338.

Bell et al., (1985) "DNA Sequence and Characterization of Human Class II Major Histocompatibility Complex β Chains from the DR1 Haplotype," *Proc. Natl. Acad. Sci. USA* 82:3405-3409.

Mosmann et al., (1990) "Isolation of Monoclonal Antibodies Specific for IL-4,IL-5, IL-6, and a New Th2-Specific Cytokine (IL-10), Cytokine Synthesis Inhibitory Factor, By Using a Solid Phase Radioimmunoadsorbent Assay," *J. Immunol.* 145:2938-2945.

*Cloning by Limiting Dilution, in Current Protocols in Immunology* (J.E. Coligan et al., eds.) John Wiley & Sons, New York, section 2.5.10-2.5.11, 1992.

Lampson and Levy (1980) "Two Populations of Ia-Like Molecules on a Human B Cell Line, " *J. Immunol.*, 125:293-299.

Harlow and Lane, (1988) eds., *Antibodies: A Laboratory Manual*Cold Spring Harbor Press, New York, pp. 272 276, 341.

Kwak et al., (1992) "Induction of Immune Responses in Patients With B-Cell Lymphoma Against The Surface-Immunoglobulin Idiotype Expressed By their Tumors," *N. Engl. J. Med.* 327:1209-1215.

Hsu et al., (1996) "Vaccination of Patients with B-Cell Lymphoma Using Autologous Antigen-Pulsed Dendritic Cells," *Nature Med.* 2:52-58.

Cosson and Bonifacion, (1992) "Role of Transmembrane Domain Interactions in the Assembly of Class II MHC Molecules," *Science* 258:659-662.

Vu et al., (1991)"Molecular Cloning of a Functional Thrombin Receptor Reveals a Novel Proteolytic Mechanism of Receptor Activation," *Cell* 64:1057-1068.

Vu et al., (1991) "Domains Specifying Thrombin-Receptor Interaction," *Nature* 353:674-677.

Haas et al., (1996) "Condon usage limitation in the expression of HIV-1 envelope glycoprotein," *Curr. Biol.* 6:315-324.

Zolotukhin et al., (1996) "A 'Humanized' Green Fluorescent Protein in cDNA Adapted for High-Level Expression in Mammalian Cells," *J. Virol.* 70:4646-4654.

Tao and Levy, (1993) "Idiotype/granulocyte-macrophage colony-stimulating factor fusion protein as a vaccine for B-cell lymphoma," *Nature* 362:755-758.

Chen et l., (1994) "Idiotype-Cytokine Fusion Protein as Cancer Vaccines: Relative Efficacy of IL-2, IL-4, and Granulocyte-Marcrophage Colony-Stimulating Factor," *J. Immunol.* 153:4775-4757.

Mehta-Damani et al., (1994) "Generation of Antigen-Specific CD8+ CTLs from Naive Precursors," *J. Immunol.* 153:996-1003.

Takamizawa et al. (1995) "Cellular and Molecular Basis of Human γδ T Cell Activation: Role of Accessory Molecules in Alloactivation," *J. Clin. Invest.* 95:296-303.

Kane et al.,"Use of a Cloned Multidrug Resistance Gene for Coamplification and Overproduction of Major Excreted Protein, a transformation-Regulated Secreted Acid Protease," Mol. Cell. Biol. 8:3316 (1988).

Cockett et al., "High Level Expression Of Tissue Inhibitor Of Metalloproteinases In Chinese Hamster Ovary Cells Using Glutamine Synthetase Gene Amplification," Bio/Technology 8:662 (1990);.

Bebbington, "Use of vectors based on gene amplification for the expression of cloned genes in mammalian cell," In: *DNA Cloning 4, A Pratical Approach*, Glower and Hames, eds., Oxford University Press pp. 85-11 (1995).

Chiang and McConlogue, "Amplification and Expression of Heterologous Ornithine Decarboxylase in Chinese Hamster Ovary Cells," Mol. Cell. Biol. 8:764 (1988).

Reff et al., "Depletion of B Cells In Vivo by Chimeric Mouse Human monoclonal Antibody to CD20," Blood 83:435 (1994).

Page and Sydenham, "High Level Expression of the Humanized Monoclonal Antibody Campath-1H in Chinese Hamster Ovary Cells," Bio/Technology 9:64 (1991).

Kim and Wold, "Stable Reduction of Thymidine Kinase Activity in Cells Expressing High Levels of Anti-Sense RNA," Cell 42:129 (1985).

Gillies et al., "Expression Of Human Anti-Tetanus Toxoid Antibody in transfected Murine Myeloma Cells," Bio/Technology 7:799 (1989).

Wood et al., "High Level Synthesis of Immunoglobulins in Chinese Hamster Ovary Cells," J. Immunol. 145:3011 (1990).

Fouser et al., "High Level Expression Of A Chimeric Anti-Ganglioside GD2 Antibody: Genomic Kappa Sequences Improve Expression In COS And CHO Cells," Bio/Technology 10:1121 (1992).

Davis et al., "High Level Expression in Chinese Hamster Ovary Cells of Soluble Forms of CD4 T Lymphocyte Glycoprotein Including Glycosylation Variants," J. Biol.Chem 265:10410 (1990).

Cartier et al., "Use of the *Escherichia coli* Gene for Asparagine Synthetase as a Selective Marker in a Shuttle Vector Capable of Dominant Transfection and Amplification in Animal Cells," Mol. Cell. Biol. 7:1623 (1987).

Cartier and Stanners, "Stable, high-level expression of a carcinoembryonic antigen-encoding cDNA after transfection and amplification with the dominant and selectable asparagine synthetase marker," Gene 95:223 (1990).

Nakatani et al., "Functional Expression of Human Monoclonal Antibody Genes Directed Aganist Pseudomonal Exotoxin A In Mouse Myeloma Cells," Bio/Technology 7:805 (1985).

Hawkins et al., *Idotypic Vaccination Aganist Human B-Cell Lymphoma. Rescue of Variable Region Gene Sequences From Biopsy Material for Assembly as Single-Chain Fv Personal Vaccines*, Blood, 83(11):3297-3288 (1994).

Stevenson et al., *Idiotypic DNA Vaccines Aganist B-cell Lymphoma*, Immunological Reviews, 145:211-228 (1995).

Tyler-Smith, *Gene Amplification in Methotrexate-resistant Mouse Cells. I. DNA Rearrangement Accompanies Dihydrofolate Reductase Gene Amplification in a T-cell Lymphoma*, J. Mol. Biol., 153:203-218 (1981).

* cited by examiner

SEQUENCE LISTING

```
<160> NUMBER OF SEQ ID NOS: 77

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
tctagagcgg ccgcggaggc cgaattcg                                           28

<210> SEQ ID NO 2
<211> LENGTH: 36
<212> TYPE: DNA
<213> ORGANISM: Artificial Sequence
<220> FEATURE:
<223> OTHER INFORMATION: Synthetic

<400> SEQUENCE: 2
gatccgaatt cggcctccgc ggccgctcta gatgca                                  36

<210> SEQ ID NO 3
<211> LENGTH: 677
<212> TYPE: DNA
<213> ORGANISM: Simian virus 40

<400> SEQUENCE: 3
ggatccagac atgataagat acattgatga gtttggacaa accacaacta gaatgcagtg        60
aaaaaaatgc tttatttgtg aaatttgtga tgctattgct ttatttgtaa ccattataag       120
ctgcaataaa caagttaaca acaacaattg cattcatttt atgtttcagg ttcagggggga      180 ggtgtgggag gttttttaaa gcaagtaaaa cctctacaaa tgtggtatgg ctgattatga      240
tcatgaacag actgtgagga ctgaggggcc tgaaatgagc cttgggactg tgaatcaatg      300
cctgtttcat gccctgagtc ttccatgttc ttctccccac catcttcatt tttatcagca      360
ttttcctggc tgtcttcatc atcatcatca ctgtttctta gccaatctaa aactccaatt      420
cccatagcca cattaaactt catttttttga tacactgaca aactaaactc tttgtccaat     480
ctctctttcc actccacaat tctgctctga atactttgag caaactcagc cacaggtctg      540
taccaaatta acataagaag caaagcaatg ccactttgaa ttattctctt ttctaacaaa      600
aactcactgc gttccaggca atgctttaaa taatctttgg gcctaaaatc tatttgtttt      660
acaaatctgg cctgcag                                                     677

<210> SEQ ID NO 4
<211> LENGTH: 39
<212> TYPE: DNA
<213> ORGANISM: Artificial Sequence
<220> FEATURE:
<223> OTHER INFORMATION: Synthetic
```

```
<400> SEQUENCE: 4
ctagaattca cgcgtaggcc tccgcggccg cgcgcatgc                             39

<210> SEQ ID NO 5
<211> LENGTH: 39
<212> TYPE: DNA
<213> ORGANISM: Artificial Sequence
<220> FEATURE:
<223> OTHER INFORMATION: Synthetic

<400> SEQUENCE: 5
aattgcatgc gcgcggccgc ggaggcctac gcgtgaatt                             39

<210> SEQ ID NO 6
<211> LENGTH: 633
<212> TYPE: DNA
<213> ORGANISM: Artificial Sequence
<220> FEATURE:
<223> OTHER INFORMATION: Synthetic

<400> SEQUENCE: 6
caagcttgct gtggaatgtg tgtcagttag ggtgtggaaa gtccccaggc tccccagcag      60
gcagaagtat gcaaagcatg catctcaatt agtcagcaac caggtgtgga agtccccag     120 gctccccagc aggcagaagt atgcaaagca tgcatctcaa ttagtcagca accatagtcc    180
cgcccctaac tccgcccatc ccgcccctaa ctccgcccag ttccgcccat tctccgcccc    240
atggctgact aattttttt atttatgcag aggccgaggc cgcctcggcc tctgagctat     300
tccagaagta gtgaggaggc ttttttggag gcctaggctt ttgcaaaaag ctcctcgagc    360
tcgcatctct ccttcacgcg cccgccgccc tacctgaggc cgccatccac gccggttgag    420
tcgcgttctg ccgcctcccg cctgtggtgc ctcctgaact gcgtccgccg tctaggtaag    480
tttagagctc aggtcgagac cgggcctttg tccggcgctc ccttggagcc tacctagact    540
cagccggctc tccacgcttt gcctgaccct gcttgctcaa ctctacgtct ttgtttcgtt    600
ttctgttctg cgccgttaca gatcgcctcg agg                                  633

<210> SEQ ID NO 7
<211> LENGTH: 635
<212> TYPE: DNA
<213> ORGANISM: Moloney LTR virus

<400> SEQUENCE: 7
caagcttgcg attagtccaa tttgttaaag acaggatatc agtggtccag gctctagttt     60
tgactcaaca atatcaccag ctgaagccta tagagtacga gccatagata aaataaaaga    120
ttttatttag tctccagaaa aaggggggaa tgaaagaccc cacctgtagg tttggcaagc    180
tagcttaagt aacgccattt tgcaaggcat ggaaaatac ataactgaga atagagaagt     240
tcagatcaag gtcaggaaca gatggaacag ctgaatatgg gccaaacagg atatctgtgg    300
taagcagttc ctgccccggc tcagggccaa gaacagatgg aacagctgaa tatgggccaa    360
acaggatatc tgtggtaagc agttcctgcc ccggctcagg gccaagaaca gatggtcccc    420
agatgcggtc cagccctcag cagtttctag agaaccatca gatgtttcca gggtgcccca    480
aggacctgaa atgaccctgt gccttatttg aactaaccaa tcagttcgct tctcgcttct    540
gttcgcgcgc ttctgctccc cgagctcaat aaaagagccc acaaccctc actcggggcg    600 ccagtcctcc gattgactga gtcgccccct cgagg                               635
```

<210> SEQ ID NO 8
<211> LENGTH: 483
<212> TYPE: DNA
<213> ORGANISM: Homo sapiens

<400> SEQUENCE: 8

```
aagctttgga gctaagccag caatggtaga gggaagattc tgcacgtccc ttccaggcgg      60
cctccccgtc accaccccccc ccaacccgcc ccgaccggag ctgagagtaa ttcatacaaa    120
aggactcgcc cctgccttgg ggaatcccag ggaccgtcgt taaactccca ctaacgtaga    180
acccagagat cgctgcgttc ccgcccctc acccgcccgc tctcgtcatc actgaggtgg     240
agaagagcat gcgtgaggct ccggtgcccg tcagtgggca gagcgcacat cgcccacagt    300
ccccgagaag ttggggggag gggtcggcaa ttgaaccggt gcctagagaa ggtggcgcgg    360
ggtaaactgg gaaagtgatg tcgtgtactg gctccgcctt ttttcccgagg gtgggggaga    420
accgtatata agtgcagtag tcgccgtgaa cgttcttttt cgcaacgggt ttgccgcctc    480
gag                                                                  483
```

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9

```
aagctttgga gctaagccag caat                                            24
```

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10

```
ctcgaggcgg caaacccgtt gcg                                             23
```

<210> SEQ ID NO 11
<211> LENGTH: 1451
<212> TYPE: DNA
<213> ORGANISM: Homo sapiens

<400> SEQUENCE: 11

```
aagctttgga gctaagccag caatggtaga gggaagattc tgcacgtccc ttccaggcgg      60
cctccccgtc accaccccccc ccaacccgcc ccgaccggag ctgagagtaa ttcatacaaa    120
aggactcgcc cctgccttgg ggaatcccag ggaccgtcgt taaactccca ctaacgtaga    180
acccagagat cgctgcgttc ccgcccctc acccgcccgc tctcgtcatc actgaggtgg     240
agaagagcca tgcgtgaggc tccggtgccc gtcagtgggc agagcgcaca tcgcccacag    300
tccccgagaa gttgggggga gggtcggca attgaaccgg tgcctagaga aggtggcgcg    360
ggtaaactg ggaaagtgat gtcgtgtact ggctccgcct ttttcccgag ggtgggggag    420
aacccgtata taagtgcagt agtcgccgtg aacgttcttt ttcgcaacgg gtttgccgcc   480
agaacacagg taagtgccgt gtgtggttcc cgcgggcctg gcctctttac ggggttatggc   540
ccttgcgtgc cttgaattac ttccacgccc ctggctgcag tacgtgattc ttgatcccga    600
gcttcgggtt ggaagtgggt gggagagttc gaggccttgc gcttaaggag ccccttcgcc    660
```

-continued

```
tcgtgcttga gttgaggcct ggcctgggcg ctggggcccc cgcgtgcgaa tctggtggca      720
ccttcgcgcc tgtctcgctg ctttcgataa gtctctagcc atttaaaatt tttgatgacc      780
tgctgcgacg cttttttct ggcaagatag tcttgtaaat gcgggccaag atctgcacac       840
tggtatttcg gttttgggg ccgcgggcgg cgacggggcc cgtgcgtccc agcgcacatg       900
ttcggcgagg cggggcctgc gagcgcggcc accgagaatc ggacggggt agtctcaagc       960
tggccggcct gctctggtgc ctggcctcgc gccgccgtgt atcgcccgc cctgggcggc       1020
aaggctggcc cggtcggcac cagttgcgtg agcggaaaga tggccgcttc ccggccctgc      1080
tgcagggagc tcaaaatgga ggacgcgcg ctcgggagag cgggcgggtg agtcacccac        1140
acaaaggaaa agggcctttc cgtcctcagc cgtcgcttca tgtgactcca cggagtaccg      1200
ggcgccgtcc aggcacctcg attagttctc gagcttttgg agtacgtcgt ctttaggttg      1260
gggggagggg ttttatgcga tggagtttcc ccacactgag tgggtggaga ctgaagttag      1320
gccagcttgg cacttgatgt aattctcctt ggaatttgcc cttttgagt ttggatcttg       1380
gttcattctc aagcctcaga cagtggttca agtttttttt cttccatttc aggtgtcgtg      1440
aaaactctag a                                                          1451
```

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12

```
tctagagttt tcacgacacc tga                                              23
```

<210> SEQ ID NO 13
<211> LENGTH: 1289
<212> TYPE: DNA
<213> ORGANISM: Mus musculus
<220> FEATURE:
<221> NAME/KEY: CDS
<222> LOCATION: (88)..(741)

<400> SEQUENCE: 13

```
ttacctcact gctttccgga gcggtagcac ctcctccgcc ggcttcctcc tcagaccgct      60
ttttgccgcg agccgaccgg tcccgtc atg ccg acc cgc agt ccc agc gtc gtg     114
                                Met Pro Thr Arg Ser Pro Ser Val Val
                                  1               5 att agc gat gat gaa cca ggt tat gac cta gat ttg ttt tgt ata cct       162
Ile Ser Asp Asp Glu Pro Gly Tyr Asp Leu Asp Leu Phe Cys Ile Pro
 10              15                  20                  25 aat cat tat gcc gag gat ttg gaa aaa gtg ttt att cct cat gga ctg       210
Asn His Tyr Ala Glu Asp Leu Glu Lys Val Phe Ile Pro His Gly Leu
                30                  35                  40 att atg gac agg act gaa aga ctt gct cga gat gtc atg aag gag atg       258
Ile Met Asp Arg Thr Glu Arg Leu Ala Arg Asp Val Met Lys Glu Met
         45                  50                  55 gga ggc cat cac att gtg gcc ctc tgt gtg ctc aag ggg ggc tat aag       306
Gly Gly His His Ile Val Ala Leu Cys Val Leu Lys Gly Gly Tyr Lys
 60                  65                  70 ttc ttt gct gac ctg ctg gat tac att aaa gca ctg aat aga aat agt      354
Phe Phe Ala Asp Leu Leu Asp Tyr Ile Lys Ala Leu Asn Arg Asn Ser
 75                  80                  85 gat aga tcc att cct atg act gta gat ttt atc aga ctg aag agc tac      402
Asp Arg Ser Ile Pro Met Thr Val Asp Phe Ile Arg Leu Lys Ser Tyr
```

```
                    90                  95                 100                105
tgt aat gat cag tca acg ggg gac ata aaa gtt att ggt gga gat gat      450
Cys Asn Asp Gln Ser Thr Gly Asp Ile Lys Val Ile Gly Gly Asp Asp
            110                 115                120 ctc tca act tta act gga aag aat gtc ttg att gtt gaa gat ata att      498
Leu Ser Thr Leu Thr Gly Lys Asn Val Leu Ile Val Glu Asp Ile Ile
            125                 130                 135 gac act ggt aaa aca atg caa act ttg ctt tcc ctg gtt aag cag tac      546
Asp Thr Gly Lys Thr Met Gln Thr Leu Leu Ser Leu Val Lys Gln Tyr
            140                 145                 150 agc ccc aaa atg gtt aag gtt gca agc ttg ctg gtg aaa agg acc tct      594
Ser Pro Lys Met Val Lys Val Ala Ser Leu Leu Val Lys Arg Thr Ser
        155                 160                 165 cga agt gtt gga tac agg cca gac ttt gtt gga ttt gaa att cca gac      642
Arg Ser Val Gly Tyr Arg Pro Asp Phe Val Gly Phe Glu Ile Pro Asp
170                 175                 180                 185 aag ttt gtt gtt gga tat gcc ctt gac tat aat gag tac ttc agg aat      690
Lys Phe Val Val Gly Tyr Ala Leu Asp Tyr Asn Glu Tyr Phe Arg Asn
                190                 195                 200 ttg aat cac gtt tgt gtc att agt gaa act gga aaa gcc aaa tac aaa      738
Leu Asn His Val Cys Val Ile Ser Glu Thr Gly Lys Ala Lys Tyr Lys
                205                 210                 215 gcc taagatgagc gcaagttgaa tctgcaaata cgaggagtcc tgttgatgtt          791
Ala gccagtaaaa ttagcaggtg ttctagtcct gtggccatct gcctagtaaa gcttttttgca  851 tgaaccttct atgaatgtta ctgttttatt tttagaaatg tcagttgctg cgtccccaga   911
cttttgattt gcactatgag cctataggcc agcctaccct ctggtagatt gtcgcttatc   971
ttgtaagaaa aacaaatctc ttaaattacc acttttaaat aataatactg agattgtatc  1031
tgtaagaagg atttaaagag aagctatatt agttttttaa ttggtatttt aattttata   1091 tattcaggag agaaagatgt gattgatatt gttaatttag acgagtctga agctctcgat  1151
ttcctatcag taacagcatc taagaggttt tgctcagtgg aataaacatg tttcagcagt  1211
gttggctgta ttttcccact ttcagtaaat cgttgtcaac agttcctttt aaatgcaaat  1271
aaataaattc taaaaatt                                                 1289

<210> SEQ ID NO 14
<211> LENGTH: 218
<212> TYPE: PRT
<213> ORGANISM: Mus musculus

<400> SEQUENCE: 14

Met Pro Thr Arg Ser Pro Ser Val Val Ile Ser Asp Asp Glu Pro Gly
1               5                  10                  15

Tyr Asp Leu Asp Leu Phe Cys Ile Pro Asn His Tyr Ala Glu Asp Leu
            20                  25                  30

Glu Lys Val Phe Ile Pro His Gly Leu Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110
```

-continued

```
Asp Ile Lys Val Ile Gly Gly Asp Leu Ser Thr Leu Thr Gly Lys
        115                 120                 125

Asn Val Leu Ile Val Glu Asp Ile Ile Asp Thr Gly Lys Thr Met Gln
    130                 135                 140

Thr Leu Leu Ser Leu Val Lys Gln Tyr Ser Pro Lys Met Val Lys Val
145                 150                 155                 160

Ala Ser Leu Leu Val Lys Arg Thr Ser Arg Ser Val Gly Tyr Arg Pro
                165                 170                 175

Asp Phe Val Gly Phe Glu Ile Pro Asp Lys Phe Val Val Gly Tyr Ala
            180                 185                 190

Leu Asp Tyr Asn Glu Tyr Phe Arg Asn Leu Asn His Val Cys Val Ile
        195                 200                 205

Ser Glu Thr Gly Lys Ala Lys Tyr Lys Ala
        210                 215
```

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
gcatgcgcgc ggccgcggag gctttttttt tttttttttt          40

<210> SEQ ID NO 16
<211> LENGTH: 27
<212> TYPE: DNA
<213> ORGANISM: Artificial Sequence
<220> FEATURE:
<223> OTHER INFORMATION: Synthetic

<400> SEQUENCE: 16
cggcaacgcg tgccatcatg gttcgac          27

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
cggcagcggc cgcatagatc taaagccagc          30

<210> SEQ ID NO 18
<211> LENGTH: 671
<212> TYPE: DNA
<213> ORGANISM: Mus musculus
<220> FEATURE:
<221> NAME/KEY: CDS
<222> LOCATION: (13)..(573)

<400> SEQUENCE: 18

```
acgcgtgcca tc atg gtt cga cca ttg aac tgc atc gtc gcc gtg tcc caa        51
              Met Val Arg Pro Leu Asn Cys Ile Val Ala Val Ser Gln
                1               5                  10 aat atg ggg att ggc aag aac gga gac cta ccc tgg cct ccg ctc agg        99
Asn Met Gly Ile Gly Lys Asn Gly Asp Leu Pro Trp Pro Pro Leu Arg
     15                  20                  25 aac gag ttc aag tac ttc caa aga atg acc aca acc tct tca gtg gaa      147
Asn Glu Phe Lys Tyr Phe Gln Arg Met Thr Thr Thr Ser Ser Val Glu
```

|   |   |   |   |   |   |   |   |   |   |   |   |   |   |   |   |
|---|---|---|---|---|---|---|---|---|---|---|---|---|---|---|---|
| | | 30 | | | | 35 | | | | 40 | | | | 45 | |
| ggt | aaa | cag | aat | ctg | gtg | att | atg | ggt | agg | aaa | acc | tgg | ttc | tcc | att | 195
| Gly | Lys | Gln | Asn | Leu | Val | Ile | Met | Gly | Arg | Lys | Thr | Trp | Phe | Ser | Ile |
| | | | | 50 | | | | | 55 | | | | | 60 | |
| cct | gag | aag | aat | cga | cct | tta | aag | gac | aga | att | aat | ata | gtt | ctc | agt | 243
| Pro | Glu | Lys | Asn | Arg | Pro | Leu | Lys | Asp | Arg | Ile | Asn | Ile | Val | Leu | Ser |
| | | | 65 | | | | | 70 | | | | | 75 | | |
| aga | gaa | ctc | aaa | gaa | cca | cca | cga | gga | gct | cat | ttt | ctt | gcc | aaa | agt | 291
| Arg | Glu | Leu | Lys | Glu | Pro | Pro | Arg | Gly | Ala | His | Phe | Leu | Ala | Lys | Ser |
| | | 80 | | | | | 85 | | | | | 90 | | | |
| ttg | gat | gat | gcc | tta | aga | ctt | att | gaa | caa | ccg | gaa | ttg | gca | agt | aaa | 339
| Leu | Asp | Asp | Ala | Leu | Arg | Leu | Ile | Glu | Gln | Pro | Glu | Leu | Ala | Ser | Lys |
| | 95 | | | | | 100 | | | | | 105 | | | | |
| gta | gac | atg | gtt | tgg | ata | gtc | gga | ggc | agt | tct | gtt | tac | cag | gaa | gcc | 387
| Val | Asp | Met | Val | Trp | Ile | Val | Gly | Gly | Ser | Ser | Val | Tyr | Gln | Glu | Ala |
| 110 | | | | | 115 | | | | | 120 | | | | | 125 |
| atg | aat | caa | cca | ggc | cac | ctt | aga | ctc | ttt | gtg | aca | agg | atc | atg | cag | 435
| Met | Asn | Gln | Pro | Gly | His | Leu | Arg | Leu | Phe | Val | Thr | Arg | Ile | Met | Gln |
| | | | | 130 | | | | | 135 | | | | | 140 | |
| gaa | ttt | gaa | agt | gac | acg | ttt | ttc | cca | gaa | att | gat | ttg | ggg | aaa | tat | 483
| Glu | Phe | Glu | Ser | Asp | Thr | Phe | Phe | Pro | Glu | Ile | Asp | Leu | Gly | Lys | Tyr |
| | | | 145 | | | | | 150 | | | | | 155 | | |
| aaa | ctt | ctc | cca | gaa | tac | cca | ggc | gtc | ctc | tct | gag | gtc | cag | gag | gaa | 531
| Lys | Leu | Leu | Pro | Glu | Tyr | Pro | Gly | Val | Leu | Ser | Glu | Val | Gln | Glu | Glu |
| | | 160 | | | | | 165 | | | | | 170 | | | |
| aaa | ggc | atc | aag | tat | aag | ttt | gaa | gtc | tac | gag | aag | aaa | gac | | | 573
| Lys | Gly | Ile | Lys | Tyr | Lys | Phe | Glu | Val | Tyr | Glu | Lys | Lys | Asp | | |
| | 175 | | | | | 180 | | | | | 185 | | | | | taacaggaag atgctttcaa gttctctgct cccctcctaa agctatgcat ttttataaga    633 ccatgggact tttgctggct ttagatctat gcggccgc    671

<210> SEQ ID NO 19
<211> LENGTH: 187
<212> TYPE: PRT
<213> ORGANISM: Mus musculus

<400> SEQUENCE: 19

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

```
Pro Glu Tyr Pro Gly Val Leu Ser Glu Val Gln Glu Glu Lys Gly Ile
            165                 170                 175

Lys Tyr Lys Phe Glu Val Tyr Glu Lys Lys Asp
            180                 185
```

<210> SEQ ID NO 20
<211> LENGTH: 34
<212> TYPE: DNA
<213> ORGANISM: Artificial Sequence
<220> FEATURE:
<223> OTHER INFORMATION: Synthetic

<400> SEQUENCE: 20
atatatctag accaccatgc ctggctcagc actg                                34

<210> SEQ ID NO 21
<211> LENGTH: 35
<212> TYPE: DNA
<213> ORGANISM: Artificial Sequence
<220> FEATURE:
<223> OTHER INFORMATION: Synthetic

<400> SEQUENCE: 21
attattgcgg ccgcttagct tttcattttg atcat                               35

<210> SEQ ID NO 22
<211> LENGTH: 134
<212> TYPE: DNA
<213> ORGANISM: Artificial Sequence
<220> FEATURE:
<223> OTHER INFORMATION: Synthetic

<400> SEQUENCE: 22
ggtctagagc caaataaagg aagtggaacc acttcaggta ctacccgtct tctatctggg    60
cacacgtgtt tcacgttgac aggtttgctt gggacgctag taaccatggg cttgctgact   120
taggcatcga attc                                                      134

<210> SEQ ID NO 23
<211> LENGTH: 134
<212> TYPE: DNA
<213> ORGANISM: Artificial Sequence
<220> FEATURE:
<223> OTHER INFORMATION: Synthetic

<400> SEQUENCE: 23
gaattcgatg cctaagtcag caagcccatg gttactagcg tcccaagcaa acctgtcaac    60
gtgaaacacg tgtgcccaga tagaagacgg gtagtacctg aagtggttcc acttccttta   120
tttggctcta gacc                                                      134

<210> SEQ ID NO 24
<211> LENGTH: 300
<212> TYPE: DNA
<213> ORGANISM: Artificial Sequence
<220> FEATURE:
<223> OTHER INFORMATION: Synthetic

<400> SEQUENCE: 24
taatacgact cactataggg cgaattggag ctccaccgcg gtggcggccg ctctagaact    60
agtggatccc ccgggctgca ggaattcgat ggtctagagc caaataaagg aagtggaacc   120
acttcaggta ctacccgtct tctatctggg cacacgtgtt tcacgttgac aggtttgctt   180

```
gggacgctag taaccatggg cttgctgact taggcatcga attcatcaag cttatcgata      240
ccgtcgacct cgagggggggg cccggtaccc agcttttgtt ccctttagtg agggttaatt      300
```

<210> SEQ ID NO 25
<211> LENGTH: 28
<212> TYPE: DNA
<213> ORGANISM: Artificial Sequence
<220> FEATURE:
<223> OTHER INFORMATION: Synthetic

<400> SEQUENCE: 25

```
ccacttcctt tatttgggag agggcttg                                          28
```

<210> SEQ ID NO 26
<211> LENGTH: 747
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(744)

<400> SEQUENCE: 26

```
atg gcc ata agt gga gtc cct gtg cta gga ttt ttc atc ata gct gtg         48
Met Ala Ile Ser Gly Val Pro Val Leu Gly Phe Phe Ile Ile Ala Val
1               5                   10                  15 ctg atg agc gct cag gaa tca tgg gct atc aaa gaa gaa cat gtg atc         96
Leu Met Ser Ala Gln Glu Ser Trp Ala Ile Lys Glu Glu His Val Ile
            20                  25                  30 atc cag gcc gag ttc tat ctg aat cct gac caa tca ggc gag ttt atg        144
Ile Gln Ala Glu Phe Tyr Leu Asn Pro Asp Gln Ser Gly Glu Phe Met
        35                  40                  45 ttt gac ttt gat ggt gat gag att ttc cat gtg gat atg gca aag aag        192
Phe Asp Phe Asp Gly Asp Glu Ile Phe His Val Asp Met Ala Lys Lys
    50                  55                  60 gag acg gtc tgg cgg ctt gaa gaa ttt gga cga ttt gcc agc ttt gag        240
Glu Thr Val Trp Arg Leu Glu Glu Phe Gly Arg Phe Ala Ser Phe Glu
65                  70                  75                  80 gct caa ggt gca ttg gcc aac ata gct gtg gac aaa gcc aac ttg gaa        288
Ala Gln Gly Ala Leu Ala Asn Ile Ala Val Asp Lys Ala Asn Leu Glu
                85                  90                  95 atc atg aca aag cgc tcc aac tat act ccg atc acc aat gta cct cca        336
Ile Met Thr Lys Arg Ser Asn Tyr Thr Pro Ile Thr Asn Val Pro Pro
            100                 105                 110 gag gta act gtg ctc acg aac agc cct gtg gaa ctg aga gag ccc aac        384
Glu Val Thr Val Leu Thr Asn Ser Pro Val Glu Leu Arg Glu Pro Asn
        115                 120                 125 gtc ctc atc tgt ttc ata gac aag ttc acc cca cca gtg gtc aat gtc        432
Val Leu Ile Cys Phe Ile Asp Lys Phe Thr Pro Pro Val Val Asn Val
    130                 135                 140 acg tgg ctt cga aat gga aaa cct gtc acc aca gga gtg tca gag aca        480
Thr Trp Leu Arg Asn Gly Lys Pro Val Thr Thr Gly Val Ser Glu Thr
145                 150                 155                 160 gtc ttc ctg ccc agg gaa gac cac ctt ttc cgc aag ttc cac tat ctc        528
Val Phe Leu Pro Arg Glu Asp His Leu Phe Arg Lys Phe His Tyr Leu
                165                 170                 175 ccc ttc ctg ccc tca act gag gac gtt tac gac tgc agg gtg gag cac        576
Pro Phe Leu Pro Ser Thr Glu Asp Val Tyr Asp Cys Arg Val Glu His
            180                 185                 190 tgg ggc ttg gat gag cct ctt ctc aag cac tgg gag ttt gat gct cca        624
Trp Gly Leu Asp Glu Pro Leu Leu Lys His Trp Glu Phe Asp Ala Pro
```

-continued

```
               195                 200                 205
agc cct ctc cca aat aaa gga agt gga acc act tca ggt act acc cgt       672
Ser Pro Leu Pro Asn Lys Gly Ser Gly Thr Thr Ser Gly Thr Thr Arg
    210                 215                 220 ctt cta tct ggg cac acg tgt ttc acg ttg aca ggt ttg ctt ggg acg       720
Leu Leu Ser Gly His Thr Cys Phe Thr Leu Thr Gly Leu Leu Gly Thr
225                 230                 235                 240 cta gta acc atg ggc ttg ctg act tag                                   747
Leu Val Thr Met Gly Leu Leu Thr
                245
```

<210> SEQ ID NO 27
<211> LENGTH: 248
<212> TYPE: PRT
<213> ORGANISM: Artificial Sequence
<220> FEATURE:
<223> OTHER INFORMATION: Synthetic Construct

<400> SEQUENCE: 27

```
Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
                20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
        50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Asn Lys Gly Ser Gly Thr Thr Ser Gly Thr Thr Arg
    210                 215                 220

Leu Leu Ser Gly His Thr Cys Phe Thr Leu Thr Gly Leu Leu Gly Thr
225                 230                 235                 240

Leu Val Thr Met Gly Leu Leu Thr
                245
```

<210> SEQ ID NO 28
<211> LENGTH: 28
<212> TYPE: DNA
<213> ORGANISM: Artificial Sequence
<220> FEATURE:
<223> OTHER INFORMATION: Synthetic

<400> SEQUENCE: 28
ccacttcctt tatttggtgc agattcag                                          28

<210> SEQ ID NO 29
<211> LENGTH: 786
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(783)

<400> SEQUENCE: 29

| | | | | | | | | | | | | | | | | |
|---|---|---|---|---|---|---|---|---|---|---|---|---|---|---|---|---|
| atg | gtg | tgt | ctg | aag | ctc | cct | gga | ggc | tcc | tgc | atg | aca | gcg | ctg | aca | 48 |
| Met | Val | Cys | Leu | Lys | Leu | Pro | Gly | Gly | Ser | Cys | Met | Thr | Ala | Leu | Thr | |
| 1 | | | | 5 | | | | | 10 | | | | | 15 | | |
| gtg | aca | ctg | atg | gtg | ctg | agc | tcc | cga | ctg | gct | ttg | gct | ggg | gac | acc | 96 |
| Val | Thr | Leu | Met | Val | Leu | Ser | Ser | Arg | Leu | Ala | Leu | Ala | Gly | Asp | Thr | |
| | | | 20 | | | | | 25 | | | | | 30 | | | |
| cga | cca | cgt | ttc | ttg | tgg | cag | ctt | aag | ttt | gaa | tgt | cat | ttc | ttc | aat | 144 |
| Arg | Pro | Arg | Phe | Leu | Trp | Gln | Leu | Lys | Phe | Glu | Cys | His | Phe | Phe | Asn | |
| | | 35 | | | | | 40 | | | | | 45 | | | | |
| ggg | acg | gag | cgg | gtg | cgg | ttg | ctg | gaa | aga | tgc | atc | tat | aac | caa | gag | 192 |
| Gly | Thr | Glu | Arg | Val | Arg | Leu | Leu | Glu | Arg | Cys | Ile | Tyr | Asn | Gln | Glu | |
| | 50 | | | | | 55 | | | | | 60 | | | | | |
| gag | tcc | gtg | cgc | ttc | gac | agc | gac | gtg | ggg | gag | tac | cgg | gcg | gtt | gag | 240 |
| Glu | Ser | Val | Arg | Phe | Asp | Ser | Asp | Val | Gly | Glu | Tyr | Arg | Ala | Val | Glu | |
| 65 | | | | | 70 | | | | | 75 | | | | | 80 | |
| gag | ctg | ggg | cgg | cct | gat | gcc | gag | tac | tgg | aac | agc | cag | aag | gac | ctc | 288 |
| Glu | Leu | Gly | Arg | Pro | Asp | Ala | Glu | Tyr | Trp | Asn | Ser | Gln | Lys | Asp | Leu | |
| | | | | 85 | | | | | 90 | | | | | 95 | | |
| ctg | gag | cag | aag | cgg | ggc | cag | gtg | gac | aat | tac | tgc | aga | cac | aac | tac | 336 |
| Leu | Glu | Gln | Lys | Arg | Gly | Gln | Val | Asp | Asn | Tyr | Cys | Arg | His | Asn | Tyr | |
| | | | 100 | | | | | 105 | | | | | 110 | | | |
| ggg | gtt | ggt | gag | agc | ttc | aca | gtg | cag | cgg | cga | gtt | gag | cct | aag | gtg | 384 |
| Gly | Val | Gly | Glu | Ser | Phe | Thr | Val | Gln | Arg | Arg | Val | Glu | Pro | Lys | Val | |
| | | 115 | | | | | 120 | | | | | 125 | | | | |
| act | gtg | tat | cct | tca | aag | acc | cag | ccc | ctg | cag | cac | cac | aac | ctc | ctg | 432 |
| Thr | Val | Tyr | Pro | Ser | Lys | Thr | Gln | Pro | Leu | Gln | His | His | Asn | Leu | Leu | |
| | 130 | | | | | 135 | | | | | 140 | | | | | |
| gtc | tgc | tct | gtg | agt | ggt | ttc | tat | cca | ggc | agc | att | gaa | gtc | agg | tgg | 480 |
| Val | Cys | Ser | Val | Ser | Gly | Phe | Tyr | Pro | Gly | Ser | Ile | Glu | Val | Arg | Trp | |
| 145 | | | | | 150 | | | | | 155 | | | | | 160 | |
| ttc | cgg | aac | ggc | cag | gaa | gag | aag | gct | ggg | gtg | gtg | tcc | acg | ggc | ctg | 528 |
| Phe | Arg | Asn | Gly | Gln | Glu | Glu | Lys | Ala | Gly | Val | Val | Ser | Thr | Gly | Leu | |
| | | | | 165 | | | | | 170 | | | | | 175 | | |
| atc | cag | aat | gga | gat | tgg | acc | ttc | cag | acc | ctg | gtg | atg | ctg | gaa | ata | 576 |
| Ile | Gln | Asn | Gly | Asp | Trp | Thr | Phe | Gln | Thr | Leu | Val | Met | Leu | Glu | Ile | |
| | | | 180 | | | | | 185 | | | | | 190 | | | |
| gtt | cct | cgg | agt | gga | gag | gtt | tac | acc | tgc | caa | gtg | gag | cac | cca | agt | 624 |
| Val | Pro | Arg | Ser | Gly | Glu | Val | Tyr | Thr | Cys | Gln | Val | Glu | His | Pro | Ser | |
| | | 195 | | | | | 200 | | | | | 205 | | | | |
| gtg | acg | agc | cct | ctc | aca | gtg | gaa | tgg | aga | gca | cgg | tct | gaa | tct | gca | 672 |
| Val | Thr | Ser | Pro | Leu | Thr | Val | Glu | Trp | Arg | Ala | Arg | Ser | Glu | Ser | Ala | |
| | 210 | | | | | 215 | | | | | 220 | | | | | |
| cca | aat | aaa | gga | agt | gga | acc | act | tca | ggt | act | acc | cgt | ctt | cta | tct | 720 |
| Pro | Asn | Lys | Gly | Ser | Gly | Thr | Thr | Ser | Gly | Thr | Thr | Arg | Leu | Leu | Ser | |
| 225 | | | | | 230 | | | | | 235 | | | | | 240 | |
| ggg | cac | acg | tgt | ttc | acg | ttg | aca | ggt | ttg | ctt | ggg | acg | cta | gta | acc | 768 |

```
Gly His Thr Cys Phe Thr Leu Thr Gly Leu Leu Gly Thr Leu Val Thr
                245                 250                 255 atg ggc ttg ctg act tag                                                 786
Met Gly Leu Leu Thr
            260

<210> SEQ ID NO 30
<211> LENGTH: 261
<212> TYPE: PRT
<213> ORGANISM: Artificial Sequence
<220> FEATURE:
<223> OTHER INFORMATION: Synthetic Construct

<400> SEQUENCE: 30

Met Val Cys Leu Lys Leu Pro Gly Gly Ser Cys Met Thr Ala Leu Thr
1               5                   10                  15

Val Thr Leu Met Val Leu Ser Ser Arg Leu Ala Leu Ala Gly Asp Thr
                20                  25                  30

Arg Pro Arg Phe Leu Trp Gln Leu Lys Phe Glu Cys His Phe Phe Asn
            35                  40                  45

Gly Thr Glu Arg Val Arg Leu Leu Glu Arg Cys Ile Tyr Asn Gln Glu
        50                  55                  60

Glu Ser Val Arg Phe Asp Ser Asp Val Gly Glu Tyr Arg Ala Val Glu
65                  70                  75                  80

Glu Leu Gly Arg Pro Asp Ala Glu Tyr Trp Asn Ser Gln Lys Asp Leu
                85                  90                  95

Leu Glu Gln Lys Arg Gly Gln Val Asp Asn Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Ile
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Pro Asn Lys Gly Ser Gly Thr Thr Ser Gly Thr Thr Arg Leu Leu Ser
225                 230                 235                 240

Gly His Thr Cys Phe Thr Leu Thr Gly Leu Leu Gly Thr Leu Val Thr
                245                 250                 255

Met Gly Leu Leu Thr
            260

<210> SEQ ID NO 31
<211> LENGTH: 189
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(186)
```

```
<400> SEQUENCE: 31 ttg gat cca cga tcg ttt cta ttg cgc aat cca aat gat aag tac gaa        48
Leu Asp Pro Arg Ser Phe Leu Leu Arg Asn Pro Asn Asp Lys Tyr Glu
1               5                   10                  15 cca ttt tgg gaa gat act aca gag aac gtg gtg tgt gcc ctg ggc ctg        96
Pro Phe Trp Glu Asp Thr Thr Glu Asn Val Val Cys Ala Leu Gly Leu
            20                  25                  30 act gtg ggt ctg gtg ggc atc att att ggg acc atc ttc atc atc aag       144
Thr Val Gly Leu Val Gly Ile Ile Ile Gly Thr Ile Phe Ile Ile Lys
        35                  40                  45 gga gtg cgc aaa agc aat gca gca gaa cgc agg ggg cct ctg taa           189
Gly Val Arg Lys Ser Asn Ala Ala Glu Arg Arg Gly Pro Leu
    50                  55                  60

<210> SEQ ID NO 32
<211> LENGTH: 62
<212> TYPE: PRT
<213> ORGANISM: Artificial Sequence
<220> FEATURE:
<223> OTHER INFORMATION: Synthetic Construct

<400> SEQUENCE: 32

Leu Asp Pro Arg Ser Phe Leu Leu Arg Asn Pro Asn Asp Lys Tyr Glu
1               5                   10                  15

Pro Phe Trp Glu Asp Thr Thr Glu Asn Val Val Cys Ala Leu Gly Leu
            20                  25                  30

Thr Val Gly Leu Val Gly Ile Ile Ile Gly Thr Ile Phe Ile Ile Lys
        35                  40                  45

Gly Val Arg Lys Ser Asn Ala Ala Glu Arg Arg Gly Pro Leu
    50                  55                  60

<210> SEQ ID NO 33
<211> LENGTH: 192
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(189)

<400> SEQUENCE: 33 ttg gat cca cga tcg ttt cta ttg cgc aat cca aat gat aag tac gaa        48
Leu Asp Pro Arg Ser Phe Leu Leu Arg Asn Pro Asn Asp Lys Tyr Glu
1               5                   10                  15 cca ttt tgg gaa gat cag agc aag atg ctg agt gga gtc ggg ggc ttc        96
Pro Phe Trp Glu Asp Gln Ser Lys Met Leu Ser Gly Val Gly Gly Phe
            20                  25                  30 gtg ctg ggc ctg ctc ttc ctt ggg gcc ggg ctg ttc atc tac ttc agg       144
Val Leu Gly Leu Leu Phe Leu Gly Ala Gly Leu Phe Ile Tyr Phe Arg
        35                  40                  45 aat cag aaa gga cac tct gga ctt cag cca aca gga ttc ctg agc tga      192
Asn Gln Lys Gly His Ser Gly Leu Gln Pro Thr Gly Phe Leu Ser
    50                  55                  60

<210> SEQ ID NO 34
<211> LENGTH: 63
<212> TYPE: PRT
<213> ORGANISM: Artificial Sequence
<220> FEATURE:
<223> OTHER INFORMATION: Synthetic Construct

<400> SEQUENCE: 34
```

```
Leu Asp Pro Arg Ser Phe Leu Leu Arg Asn Pro Asn Asp Lys Tyr Glu
1               5                   10                  15

Pro Phe Trp Glu Asp Gln Ser Lys Met Leu Ser Gly Val Gly Gly Phe
            20                  25                  30

Val Leu Gly Leu Leu Phe Leu Gly Ala Gly Leu Phe Ile Tyr Phe Arg
            35                  40                  45

Asn Gln Lys Gly His Ser Gly Leu Gln Pro Thr Gly Phe Leu Ser
    50                  55                  60

<210> SEQ ID NO 35
<211> LENGTH: 39
<212> TYPE: DNA
<213> ORGANISM: Artificial Sequence
<220> FEATURE:
<223> OTHER INFORMATION: Synthetic

<400> SEQUENCE: 35
cgatcgtgga tccaagttta ggttcgtatc tgtttcaaa                     39

<210> SEQ ID NO 36
<211> LENGTH: 34
<212> TYPE: DNA
<213> ORGANISM: Artificial Sequence
<220> FEATURE:
<223> OTHER INFORMATION: Synthetic

<400> SEQUENCE: 36
cgatcgagga tccaagatgg tggcagacag gacc                          34

<210> SEQ ID NO 37
<211> LENGTH: 32
<212> TYPE: DNA
<213> ORGANISM: Artificial Sequence
<220> FEATURE:
<223> OTHER INFORMATION: Synthetic

<400> SEQUENCE: 37
acgcgtccac catggccata agtggagtcc ct                            32

<210> SEQ ID NO 38
<211> LENGTH: 28
<212> TYPE: DNA
<213> ORGANISM: Artificial Sequence
<220> FEATURE:
<223> OTHER INFORMATION: Synthetic

<400> SEQUENCE: 38
ggatccaact ctgtagtctc tgggagag                                 28

<210> SEQ ID NO 39
<211> LENGTH: 32
<212> TYPE: DNA
<213> ORGANISM: Artificial Sequence
<220> FEATURE:
<223> OTHER INFORMATION: Synthetic

<400> SEQUENCE: 39
acgcgtccac catggtgtgt ctgaagctcc tg                            32

<210> SEQ ID NO 40
<211> LENGTH: 29
<212> TYPE: DNA
<213> ORGANISM: Artificial Sequence
<220> FEATURE:
<223> OTHER INFORMATION: Synthetic
```

```
<400> SEQUENCE: 40
ggatccaact tgctctgtgc agattcaga                                    29

<210> SEQ ID NO 41
<211> LENGTH: 292
<212> TYPE: DNA
<213> ORGANISM: Homo sapiens

<400> SEQUENCE: 41
gaattctttt ttgcgtgtgg cagttttaag ttattagttt ttaaaatcag tactttttaa   60
tggaaacaac ttgaccaaaa atttgtcaca gaattttgag acccattaaa aaagttaaat  120
gagaaacctg tgtgttcctt tggtcaacac cgagacattt aggtgaaaga catctaattc  180
tggttttacg aatctggaaa cttcttgaaa atgtaattct tgagttaaca cttctgggtg  240
gagaataggg ttgttttccc cccacataat tggaagggga aggaatatcg at         292

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
tcgatggcgc gccttaatta                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
agcttaatta aggcgcgcca                                              20

<210> SEQ ID NO 44
<211> LENGTH: 1147
<212> TYPE: DNA
<213> ORGANISM: Artificial Sequence
<220> FEATURE:
<223> OTHER INFORMATION: Synthetic

<400> SEQUENCE: 44
gcggccgcgt cgaccaaggg ccccagcgtg ttccccctgg cccctgctc ccgcagcacc    60 agcggcggca ccgccgccct gggctgcctg gtgaaggact acttccccga gcccgtgacc  120
gtgagctgga acagcggcgc cctgaccagc ggcgtccaca ccttccccgc cgtgctgcag  180
tccagcggcc tgtactccct gagcagcgtg gtgaccgtgc ccagcagcag cctgggcacc  240
cagacctaca cctgcaacgt gaaccacaag cccagcaaca ccaaggtgga caagcgcgtg  300
gagctgaaga ccccccctggg cgacaccacc cacacctgcc ccgctgcccc cgagcccaag  360
agctgcgaca cccctccccc ctgccccgc tgccccgagc caagagctg cgacacccct     420 ccccctgcc ccgctgcccc cgagcccaag agctgcgaca cccctccccc ctgccccgc    480 tgccccgccc ccgagctgct gggcggcccc agcgtgttcc tgttccccc caagcccaag   540 gacacccctga tgatctcccg cacccccgag gtgacctgcg tggtggtgga cgtgagccac  600
gaggaccccg aggtgcagtt caagtggtac gtggacggcg tggaggtgca taacgccaag  660
```

-continued

```
accaagcccc gcgaggagca gtacaacagc accttccgcg tggtgagcgt gctgaccgtg    720
ctgcaccagg actggctgaa cggcaaggag tacaagtgca aggtgagcaa caaggccctg    780
cccgccccca tcgagaagac catctccaag accaagggcc agccccgcga gccccaggtg    840
tacaccctgc cccccagccg cgaggagatg accaagaacc aggtgagcct gacctgcctg    900
gtgaagggct tctacccag cgacatcgcc gtggagtggg agagcagcgg ccagcccgag    960
aacaactaca acaccacccc ccccatgctg gacagcgacg gcagcttctt cctgtacagc   1020
aagctgaccg tggacaagag ccgctggcag cagggcaaca tcttctcctg cagcgtgatg   1080
catgaggccc tgcacaaccg cttcacccag aagagcctga gcctgagccc cggcaagtga   1140
tagatct                                                             1147
```

<210> SEQ ID NO 45
<211> LENGTH: 377
<212> TYPE: PRT
<213> ORGANISM: Homo sapiens

<400> SEQUENCE: 45

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

```
Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 46
<211> LENGTH: 999
<212> TYPE: DNA
<213> ORGANISM: Artificial Sequence
<220> FEATURE:
<223> OTHER INFORMATION: Synthetic

<400> SEQUENCE: 46
gcggccgcgc gtcgaccaag ggccccagcg tgttcccect ggccccctgc agccgcagca      60
ccagcgagag caccgccgcc ctgggctgcc tggtgaagga ctacttcccc gagcccgtga     120
ccgtgagctg gaacagcggc gccctgacca gcggcgtgca caccttcccc gccgtgctgc     180
agagcagcgg cctgtactcc ctgagcagcg tggtgaccgt gccagcagc agcctgggca     240 ccaagaccta cacctgcaac gtggaccaca agcccagcaa caccaaggtg gacaagcgcg     300
tggagagcaa gtacggcccc ccctgcccca gctgccccgc ccccgagttc ctgggcggcc     360
ccagcgtgtt cctgttcccc cccaagccca aggacaccct gatgatcagc cgcaccccg      420 aggtgacctg cgtggtggtg gacgtgagcc aggaggaccc cgaggtgcag ttcaactggt     480
acgtggacgg cgtggaggtg cataacgcca agaccaagcc ccgcgaggag cagttcaaca     540
gcacctaccg cgtggtgagc gtgctgaccg tgctgcacca ggactggctg aacggcaagg     600
agtacaagtg caaggtgtcc aacaagggcc tgcccagcag catcgagaag accatcagca     660
aggccaaggg ccagccccgc gagccccagg tgtacaccct gccccccagc caggaggaga     720
tgaccaagaa ccaggtgagc ctgacctgcc tggtgaaggg cttctacccc agcgacatcg     780
ccgtggagtg ggagagcaac ggccagcccg agaacaacta caagaccacc ccccccgtgc     840
tggacagcga cggcagcttc ttcctgtaca gccgcctgac cgtggacaag agccgctggc     900
aggagggcaa cgtgttctcc tgctccgtga tgcatgaggc cctgcacaac cactacaccc     960
agaagagcct gagcctgagc ctgggcaagt gatagatct                           999

<210> SEQ ID NO 47
<211> LENGTH: 327
<212> TYPE: PRT
<213> ORGANISM: Homo sapiens

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Ser Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 48
<211> LENGTH: 337
<212> TYPE: DNA
<213> ORGANISM: Artificial Sequence
<220> FEATURE:
<223> OTHER INFORMATION: Synthetic

<400> SEQUENCE: 48
gcggccgcac tgtggctgca ccatctgtct tcatcttccc gccatctgat gagcagctta    60
agtccggaac cgccagcgtg gtgtgcctgc tgaacaactt ctaccccgc gaggccaagg    120 tgcagtggaa ggtggacaac gccctccaga gcggcaactc ccaggagagc gtgaccgagc    180
aggacagcaa ggacagcacc tacagcctga gcagcaccct gaccctgagc aaggccgact    240
acgagaagca caaggtgtac gcctgcgagg tgacccatca gggcctgagc agcccgtga    300 ccaagagctt caaccggggc gagtgctagt gagatct                              337

<210> SEQ ID NO 49
```

<211> LENGTH: 106
<212> TYPE: PRT
<213> ORGANISM: Homo sapiens

<400> SEQUENCE: 49

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 50
<211> LENGTH: 346
<212> TYPE: DNA
<213> ORGANISM: Artificial Sequence
<220> FEATURE:
<223> OTHER INFORMATION: Synthetic

<400> SEQUENCE: 50
gcggccgcac cgtcctaggt cagcccaagg cggcgcccag cgtgaccctg ttcccccca        60 gcagcgagga gctgcaggcc aacaaggcca ccctggtgtg cctgatcagc gacttctacc      120
ccggggccgt gaccgtggcc tggaaggccg acagcagccc cgtgaaggcc ggcgtggaga      180 ccacccccc cagcaagcag agcaacaaca agtacgccgc cagcagctac ctgagcctga      240
cccccgagca gtggaagagc caccgcagct acagctgcca ggtcacccac gagggcagca      300
ccgtggagaa gaccgtggcc cccaccgagt gcagctagtg agatct                    346

<210> SEQ ID NO 51
<211> LENGTH: 109
<212> TYPE: PRT
<213> ORGANISM: Homo sapiens

<400> SEQUENCE: 51

Thr Val Leu Gly Gln Pro Lys Ala Ala Pro Ser Val Thr Leu Phe Pro
1               5                   10                  15

Pro Ser Ser Glu Glu Leu Gln Ala Asn Lys Ala Thr Leu Val Cys Leu
            20                  25                  30

Ile Ser Asp Phe Tyr Pro Gly Ala Val Thr Val Ala Trp Lys Ala Asp
        35                  40                  45

Ser Ser Pro Val Lys Ala Gly Val Glu Thr Thr Pro Ser Lys Gln
    50                  55                  60

Ser Asn Asn Lys Tyr Ala Ala Ser Ser Tyr Leu Ser Leu Thr Pro Glu
65                  70                  75                  80

Gln Trp Lys Ser His Arg Ser Tyr Ser Cys Gln Val Thr His Glu Gly
                85                  90                  95

Ser Thr Val Glu Lys Thr Val Ala Pro Thr Glu Cys Ser
            100                 105

```
<210> SEQ ID NO 52
<211> LENGTH: 38
<212> TYPE: DNA
<213> ORGANISM: Artificial Sequence
<220> FEATURE:
<223> OTHER INFORMATION: Synthetic

<400> SEQUENCE: 52
tctagaattc acgcgtccac catggactgg acctggag                              38

<210> SEQ ID NO 53
<211> LENGTH: 41
<212> TYPE: DNA
<213> ORGANISM: Artificial Sequence
<220> FEATURE:
<223> OTHER INFORMATION: Synthetic

<400> SEQUENCE: 53
tctagaattc acgcgtccac catggacaca ctttgctaca c                          41

<210> SEQ ID NO 54
<211> LENGTH: 42
<212> TYPE: DNA
<213> ORGANISM: Artificial Sequence
<220> FEATURE:
<223> OTHER INFORMATION: Synthetic

<400> SEQUENCE: 54
tctagaattc acgcgtccac catggagttt gggctgagct gg                         42

<210> SEQ ID NO 55
<211> LENGTH: 44
<212> TYPE: DNA
<213> ORGANISM: Artificial Sequence
<220> FEATURE:
<223> OTHER INFORMATION: Synthetic

<400> SEQUENCE: 55
tctagaattc acgcgtccac catgaaacac ctgtggttct tcct                       44

<210> SEQ ID NO 56
<211> LENGTH: 41
<212> TYPE: DNA
<213> ORGANISM: Artificial Sequence
<220> FEATURE:
<223> OTHER INFORMATION: Synthetic

<400> SEQUENCE: 56
tctagaattc acgcgtccac catggggtca accgccatcc t                          41

<210> SEQ ID NO 57
<211> LENGTH: 44
<212> TYPE: DNA
<213> ORGANISM: Artificial Sequence
<220> FEATURE:
<223> OTHER INFORMATION: Synthetic

<400> SEQUENCE: 57
tctagaattc acgcgtccac catgtctgtc tccttcctca tctt                       44

<210> SEQ ID NO 58
<211> LENGTH: 24
<212> TYPE: DNA
<213> ORGANISM: Artificial Sequence
<220> FEATURE:
<223> OTHER INFORMATION: Synthetic
```

<400> SEQUENCE: 58
gcctgagttc cacgacaccg tcac                                              24

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
ggggaaaagg gttggggcgg atgc                                              24

<210> SEQ ID NO 60
<211> LENGTH: 39
<212> TYPE: DNA
<213> ORGANISM: Artificial Sequence
<220> FEATURE:
<223> OTHER INFORMATION: Synthetic

<400> SEQUENCE: 60
gaggggccct tggtcgacgc tgaggagacg gtgaccagg                              39

<210> SEQ ID NO 61
<211> LENGTH: 40
<212> TYPE: DNA
<213> ORGANISM: Artificial Sequence
<220> FEATURE:
<223> OTHER INFORMATION: Synthetic

<400> SEQUENCE: 61
gaggggccct tggtcgacgc tgaagagacg gtgaccattg                             40

<210> SEQ ID NO 62
<211> LENGTH: 39
<212> TYPE: DNA
<213> ORGANISM: Artificial Sequence
<220> FEATURE:
<223> OTHER INFORMATION: Synthetic

<400> SEQUENCE: 62
gaggggccct tggtcgacgc tgaggagacg gtgaccgtg                              39

<210> SEQ ID NO 63
<211> LENGTH: 45
<212> TYPE: DNA
<213> ORGANISM: Artificial Sequence
<220> FEATURE:
<223> OTHER INFORMATION: Synthetic

<400> SEQUENCE: 63
tctagaattc acgcgtccac catggacatg agggtccccg ctcag                       45

<210> SEQ ID NO 64
<211> LENGTH: 40
<212> TYPE: DNA
<213> ORGANISM: Artificial Sequence
<220> FEATURE:
<223> OTHER INFORMATION: Synthetic

<400> SEQUENCE: 64
tctagaattc acgcgtccac catgaggctc cctgctcagc                             40

<210> SEQ ID NO 65
<211> LENGTH: 42

```
<210> SEQ ID NO 65
<211> LENGTH: 42
<212> TYPE: DNA
<213> ORGANISM: Artificial Sequence
<220> FEATURE:
<223> OTHER INFORMATION: Synthetic

<400> SEQUENCE: 65
tctagaattc acgcgtccac catggaagcc ccagcgcagc tt                42

<210> SEQ ID NO 66
<211> LENGTH: 41
<212> TYPE: DNA
<213> ORGANISM: Artificial Sequence
<220> FEATURE:
<223> OTHER INFORMATION: Synthetic

<400> SEQUENCE: 66
tctagaattc acgcgtccac catggtgttg cagacccagg t                 41

<210> SEQ ID NO 67
<211> LENGTH: 41
<212> TYPE: DNA
<213> ORGANISM: Artificial Sequence
<220> FEATURE:
<223> OTHER INFORMATION: Synthetic

<400> SEQUENCE: 67
tctagaattc acgcgtccac catggggtcc caggttcacc t                 41

<210> SEQ ID NO 68
<211> LENGTH: 43
<212> TYPE: DNA
<213> ORGANISM: Artificial Sequence
<220> FEATURE:
<223> OTHER INFORMATION: Synthetic

<400> SEQUENCE: 68
tctagaattc acgcgtccac catgttgcca tcacaactca ttg               43

<210> SEQ ID NO 69
<211> LENGTH: 41
<212> TYPE: DNA
<213> ORGANISM: Artificial Sequence
<220> FEATURE:
<223> OTHER INFORMATION: Synthetic

<400> SEQUENCE: 69
tctagaattc acgcgtccac catggtgtcc ccgttgcaat t                 41

<210> SEQ ID NO 70
<211> LENGTH: 34
<212> TYPE: DNA
<213> ORGANISM: Artificial Sequence
<220> FEATURE:
<223> OTHER INFORMATION: Synthetic

<400> SEQUENCE: 70
ggttccggac ttaagctgct catcagatgg cggg                         34

<210> SEQ ID NO 71
<211> LENGTH: 44
<212> TYPE: DNA
<213> ORGANISM: Artificial Sequence
<220> FEATURE:
<223> OTHER INFORMATION: Synthetic

<400> SEQUENCE: 71
```

-continued tctagaattc acgcgtccac catggcctgc tctcctctcc tcct    44

<210> SEQ ID NO 72
<211> LENGTH: 44
<212> TYPE: DNA
<213> ORGANISM: Artificial Sequence
<220> FEATURE:
<223> OTHER INFORMATION: Synthetic

<400> SEQUENCE: 72
tctagaattc acgcgtccac catggcctgg gctctgctgc tcct    44

<210> SEQ ID NO 73
<211> LENGTH: 45
<212> TYPE: DNA
<213> ORGANISM: Artificial Sequence
<220> FEATURE:
<223> OTHER INFORMATION: Synthetic

<400> SEQUENCE: 73
tctagaattc acgcgtccac catggcctgg atccttctcc tcctc    45

<210> SEQ ID NO 74
<211> LENGTH: 45
<212> TYPE: DNA
<213> ORGANISM: Artificial Sequence
<220> FEATURE:
<223> OTHER INFORMATION: Synthetic

<400> SEQUENCE: 74
tctagaattc acgcgtccac catggcctgg accctctct ggctc    45

<210> SEQ ID NO 75
<211> LENGTH: 41
<212> TYPE: DNA
<213> ORGANISM: Artificial Sequence
<220> FEATURE:
<223> OTHER INFORMATION: Synthetic

<400> SEQUENCE: 75
tctagaattc acgcgtccac catggcctgg gccccactac t    41

<210> SEQ ID NO 76
<211> LENGTH: 44
<212> TYPE: DNA
<213> ORGANISM: Artificial Sequence
<220> FEATURE:
<223> OTHER INFORMATION: Synthetic

<400> SEQUENCE: 76
tctagaattc acgcgtccac catggcctgg atgatgcttc tcct    44

<210> SEQ ID NO 77
<211> LENGTH: 29
<212> TYPE: DNA
<213> ORGANISM: Artificial Sequence
<220> FEATURE:
<223> OTHER INFORMATION: Synthetic

<400> SEQUENCE: 77
ggcgccgcct tgggctgacc taggacggt    29

VACCINES FOR TREATMENT OF LYMPHOMA AND LEUKEMIA

This is a Divisional of application Ser. No. 08/761,277, filed Dec. 6, 1996, now U.S. Pat. No. 5,972,334.

This is a Continuation-In-Part of application Ser. No. 08/644,664 filed May 1, 1996, now U.S. Pat. No. 5,776,746.

FIELD OF THE INVENTION

The present invention generally relates to improved methods for the amplification and expression of recombinant genes in cells. The amplified cells provide large quantities of recombinant proteins suitable for immunotherapy for treatment of lymphomas and leukemias.

BACKGROUND OF THE INVENTION

As an increasing number of genes are isolated and developed for the expression of a wide array of useful polypeptide drugs, there is an increasing need to enhance the efficiencies and economies of the process. It is advantageous to obtain such polypeptides from mammalian cells since such polypeptides or proteins are generally correctly folded, appropriately modified and completely functional, often in marked contrast to those proteins as expressed in bacterial cells.

When large amounts of product are required, it is necessary to identify cell clones in which the vector sequences are maintained (i.e., retained) during cell proliferation. Such stable vector maintenance can be achieved either as a consequence of integration of the vector into the DNA of the host cell or by use of a viral replicon such as bovine papillomavirus (BPV).

The use of viral vectors such as BPV-based vectors for the generation of stable cell lines expressing large amounts of a recombinant protein has been successful in some cases; however, the use of viral vectors is limited by the fact that the viral vectors are restricted in the cell types in which they can replicate. Furthermore expression levels and episomal maintenance of the viral vector can be influenced by the DNA sequences inserted into the vector.

Where the vector has been integrated into the genomic DNA of the host cell to improve stability, the copy number of the vector DNA, and concomitantly the amount of product which could be expressed, can be increased by selecting for cell lines in which the vector sequences have been amplified after integration into the DNA of the host cell.

A known method for carrying out such a selection procedure is to transform a host cell with a vector comprising a DNA sequence which encodes an enzyme which is inhibited by a known drug. The vector may also comprise a DNA sequence which encodes a desired protein. Alternatively the host cell may be co-transformed with a second vector which comprises the DNA sequence which encodes the desired protein.

The transformed or co-transformed host cells are then cultured in increasing concentrations of the known drug hereby selecting drug-resistant cells. It has been found that one common mechanism leading to the appearance of mutant cells which can survive in the increased concentrations of the otherwise toxic drug is the over-production of the enzyme which is inhibited by the drug. This most commonly results from increased levels of its particular mRNA, which in turn is frequently caused by amplification of vector DNA and hence gene copies.

It has also been found that when drug resistance is caused by an increase in copy number of the vector DNA encoding the inhibitable enzyme, there is a concomitant increase in the copy number of the vector DNA encoding the desired protein in the DNA of the host cell. There is thus an increased level of production of the desired protein.

The most commonly used system for such co-amplification uses dihydrofolate reductase (DHFR) as the inhibitable enzyme. This enzyme can be inhibited by the drug methotrexate (MTX). To achieve co-amplification, a host cell which lacks an active gene which encodes DHFR is either transformed with a vector which comprises DNA sequences encoding DHFR and a desired protein or co-transformed with a vector comprising a DNA sequence encoding DHFR and a vector comprising a DNA sequence encoding the desired protein. The transformed or co-transformed host cells are cultured in media containing increasing levels of MTX, and those cell lines which survive are selected.

The co-amplification systems which are presently available suffer from a number of disadvantages. For instance, it is generally necessary to use a host cell which lacks an active gene encoding the enzyme which can be inhibited. This tends to limit the number of cell lines which can be used with any particular co-amplification system.

For instance, there are at present, only two cell lines known which lack the gene encoding DHFR and both of these cell lines are derivatives of the CHO-KI cell line. These DHFR⁻ CHO cell lines cannot be used to express certain protein products at high levels because CHO cells lack specialized postranslational modification pathways. For example, the production of functional human protein C requires that the cell possess the vitamin K-dependent γ-carboxylation pathway; CHO cells cannot properly modify the human protein C protein [Walls et al., (1989) Gene 81:139].

Attempts to use DHFR genes as dominant selectable markers in other cell lines (i.e., cell lines synthesizing wild type levels of DHFR) has not proved satisfactory. For instance, a MTX-resistant mutant DHFR or a DHFR gene under the control of a very strong promoter can act as a dominant selectable marker in certain cell types but such high concentrations of MTX are required that it has not been possible to achieve high copy numbers by selection for gene amplification using current methodologies.

Another approach to allow the use of DHFR as a dominant selectable marker in DHFR⁺ cell lines is the use of both the DHFR gene and a gene encoding a selectable marker, such as the hygromycin phosphotransferase (hyg) gene, in addition to the gene of interest [Walls, et al. (1989), supra]. This approach is used to circumvent the problem of amplification of the endogenous dhfr gene during selection with MTX. The cells are transfected with DNA encoding the three genes and the cells are first selected for their ability to grow in hygromycin. The cells are then selected for the ability to grow in increasing concentrations of MTX. While this approach allows for the co-amplification of genes in dhfr⁺ cell lines, present protocols show that the dhfr gene is amplified to a higher degree than the gene of interest with successive rounds of amplification (i.e., stepwise increases in MTX concentration). For example, in several amplified clones the dhfr gee was present at approximately 100 copies while the gene of interest was present at only 20 copies.

Clearly, the art needs improved methods which would consistently provide for the coincidental amplification of the amplifiable marker and the gene of interest in a variety of cell lines. Furthermore, the art needs a means of amplifying DNA sequences of interest which is efficient, reproducible and which is not limited to the use of specialized enzyme deficient host cell lines or to a limited number of cell lines.

Improved methods which consistently provide for the coincidental amplification of the amplifiable marker and the gene of interest in a variety of cell lines and which are efficient and reproducible would allow the production of custom tumor-specific vaccines on a scale commensurate with patient demand. Current methods for producing custom tumor vaccines for the treatment of B-cell lymphoma are insufficient to meet current and anticipated future demand.

SUMMARY OF THE INVENTION

The present invention provides methods for the production of cell lines containing amplified copies of recombinant DNA sequences. Because the amplified cell lines contain several different recombinant DNA sequences (e.g., the amplification vector, one or more expression vectors and optionally a selection vector) which are coordinately amplified, the cell lines are said to have co-amplified the input or exogenous DNA sequences. The methods of the present invention permit the efficient isolation of the desired amplified cell lines with a considerable savings in time relative to existing amplification protocols. The gene amplification methods of the present invention permit the production of custom vaccines, including multivalent vaccines, which are useful for the treatment of immune cell tumors (e.g., lymphomas and leukemias).

In one embodiment, the present invention provides a multivalent vaccine comprising at least two recombinant variable regions of immunoglobulin molecules derived from B-cell lymphoma cells, wherein said cells express at least two different immunoglobulin molecules, said immunoglobulin molecules differing by at least one idiotope. The invention is not limited by the context in which the recombinant variable regions are utilized; the variable regions may be present within an entire recombinant immunoglobulin (Ig) molecule, they may be present on Fab, Fab' or F(ab')$_2$ fragments (which may be generated by cleavage of the recombinant Ig molecule or they may be produced using molecular biological means) or they may be present on single chain antibody (Fv) molecules. In a preferred embodiment, the multivalent vaccine comprises at least two recombinant immunoglobulin molecules comprising said recombinant variable regions derived from said lymphoma cells.

In one embodiment, the immunoglobulin molecules comprising recombinant variable regions derived from a patient's lymphoma cells are covalently linked to an immune-enhancing cytokine. The linkage of the cytokine to the Ig molecule may be achieved by a variety of means known to the art including conventional coupling techniques (e.g., coupling with dehydrating agents such as dicyclohexylcarbodiimide (DCCI), ECDI and the like), the use of linkers capable of coupling through sulfhydryl groups, amino groups or carboxyl groups (available from Pierce Chemical Co., Rockford, Ill.), by reductive amination. In addition, the covalent linkage may be achieved by molecular biological means (e.g., the production of a fusion protein using an expression vector comprising a nucleotide sequence encoding the recombinant Ig operably linked to a nucleotide sequence encoding the desired cytokine).

The invention is not limited by the immune-enhancing cytokine employed. In a preferred embodiment, the cytokine is selected from the group consisting of granulocyte-macrophage colony stimulating factor, interleukin-2 and interleukin-4.

In one embodiment, the multivalent vaccines of the present invention comprise at least one pharmaceutically acceptable excipient. The invention is not limited by the nature of the excipient employed. The pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

In a preferred embodiment, the multivalent vaccine further comprises an adjuvant. When the vaccine is to be administered to a human subject, adjuvants approved for use in humans are employed (e.g., SAF-1, alum, etc.). The recombinant Ig proteins (including fragments of Ig proteins) which comprise the multivalent vaccine may be conjugated to a carrier protein such as KLH.

The present invention also provides a method of producing a vaccine for treatment of B-cell lymphoma comprising: a) providing: i) malignant cells isolated from a patient having a B-cell lymphoma; ii) an amplification vector comprising a recombinant oligonucleotide having a sequence encoding a first inhibitable enzyme operably linked to a heterologous promoter; iii) a eukaryotic parent cell line; b) isolating from the malignant cells nucleotide sequences encoding at least one $V_H$ region and at least one $V_L$ region, the $V_H$ and $V_L$ regions derived from immunoglobulin molecules expressed by the malignant cells; c) inserting the nucleotide sequences encoding the $V_H$ and $V_L$ regions into at least one expression vector; d) introducing the expression vector(s) and the amplification vector into the parent cell to generate one or more transformed cells; e) growing the transformed cell(s) in a first aqueous solution containing an inhibitor capable of inhibiting the inhibitable enzyme wherein the concentration of the inhibitor present in the first aqueous solution is sufficient to prevent growth of the parent cell line; and f) identifying a transformed cell capable of growth in the first aqueous solution, wherein the transformed cell(s) capable of growth expresses the $V_H$ and $V_L$ regions. In a preferred embodiment, the transformed cell capable of growth in the first aqueous solution contains an amplified number of copies of the expression vector(s) and an amplified number of copies of the amplification vector.

In another preferred embodiment, the nucleotide sequences encoding the $V_H$ and $C_L$ regions comprise at least two $V_H$ and at least two $C_L$ regions (in this manner, a multivalent vaccine is produced).

The method of the present invention is not limited by the nature of the means employed to introduce the vectors into the parent cell line. The art is well aware of numerous methods which allow the introduction of exogenous DNA sequences into mammalian cells, including but not limited to electroporation, microinjection, lipofection, protoplast fusion, liposome fusion and the like. In a preferred embodiment, the vectors are introduced into the parent cell line by electroporation.

The present invention is not limited by the nature of the cell line chosen as the parent cell line; a variety of mammalian cell lines may be employed including CHO cell lines and variants thereof, mouse L cells and BW5147 cells and variants thereof. The chosen cell line grow in either an attachment-dependent or attachment-independent manner. In a preferred embodiment, the parent cell line is a T lymphoid cell line; a particularly preferred T lymphoid cell line is the BW5147.G.1.4 cell line.

In another embodiment, the method of the present invention employs a parent cell line which contains an endogenous gene encoding a second inhibitable enzyme (e.g., the genome of the parent cell line contains an endogenous gene comprising a coding region encoding a second inhibitable enzyme which is operably linked to the promoter naturally linked to this coding region (i.e., the endogenous promoter for this gene). A contrast is made between the input or exogenous recombinant sequences encoding the first inhibitable enzyme and an endogenous gene encoding an inhibitable enzyme. The endogenous gene sequences will be expressed under the control of the endogenous promoter. Typically, the amplification vector will comprise a sequence encoding an inhibitable enzyme operably linked to a heterologous (i.e., not the endogenous) promoter. The sequences encoding the first and the second inhibitable enzyme may encode the same or a different enzyme. Furthermore, when the same enzyme is encoded by the two sequences (i.e., the recombinant and the endogenous sequences), these sequences may be derived from the same or a different source (i.e., the recombinant sequence may encode an enzyme isolated from a mouse cell and may introduced into a mouse cell line which contains an endogenous gene encoding the same enzyme; alternatively, the recombinant sequence may encode an enzyme derived from a different species than that of the parent cell line (e.g., the recombinant sequence may encode a rat DHFR and may be introduced into a parent mouse cell line which expresses the mouse DHFR). The amplifiable gene (or marker) and the selectable marker may be present on the same vector; alternatively, they may be present on two separate vectors.

In one embodiment the second inhibitable enzyme expressed by the parent cell line is selected from the group consisting of dihydrofolate reductase, glutamine synthetase, adenosine deaminase, asparagine synthetase.

In another embodiment, the method of the present invention the concentration of inhibitor present in the first aqueous solution (e.g., tissue culture medium) used to allow identification of the transformed cell(s) containing amplified copies of the amplification vector and amplified copies of the expression vector(s) is four-fold to six-fold the concentration required to prevent the growth of the parent cell line. It is well understood by those skilled in the art that only those sequences present on the amplification vector and expression vector(s) which are required for the expression of the inhibitable enzyme and the protein(s) of interest, respectively, need to be amplified. However, it is also well understood that any vector backbone sequences linked to the sequences required for expression of the inhibitable enzyme or protein(s) of interest may also be amplified (and typically are) during the co-amplification process.

In still another embodiment, the method of the present invention further comprises providing a selection vector encoding a selectable gene product (i.e., a selectable marker) which is introduced into said parent cell line together with said expression vector and said amplification vector (alternatively, the selectable marker may be present on the same vector which contains the amplifiable marker). The invention is not limited by the nature of the selectable gene product employed. The selectable gene product employed may be a dominant selectable marker including but not limited to hygromycin G phosphotransferase (e.g., the hyg gene product), xanthine-guanine phosphoribosyltransferase (e.g., the gpt gene product) and aminoglycoside 3' phosphotransferase (e.g., the neo gene product). Alternatively, the selectable marker employed may require the use of a parent cell line which lacks the enzymatic activity encoded by the selectable marker such as hypoxanthine guanine phosphoribosyltransferase, thymidine kinase or carbamoyl-phosphate synthetase-aspartate transcarbamoylase-dihydroorotatase. In a particularly preferred embodiment, the selection vector encodes an active hypoxanthine guanine phosphoribosyltransferase. When the selection vector encodes an active hypoxanthine guanine phosphoribosyltransferase, the second aqueous solution which requires the expression of this selectable gene product comprises hypoxanthine and azaserine.

In another embodiment, the method of the present invention further comprises following the introduction of the vectors (i.e., the amplification, expression and selection vectors), the additional step of growing the transformed cell in a second aqueous solution which requires the expression of the selectable gene product prior to growing the transformed cell in a first aqueous solution containing an inhibitor capable of inhibiting said inhibitable enzyme.

The method of the present invention is not limited by the nature of the inhibitable enzyme encoded by the amplification vector; the art is well of aware of numerous amplifiable markers. In a preferred embodiment, the amplification vector encodes an active enzyme selected from the group consisting of dihydrofolate reductase, glutamine synthetase, adenosine deaminase, asparagine synthetase.

In another preferred embodiment, the inhibitor used to select for a transformed cell expressing the inhibitable enzyme encoded by the amplification vector is selected from the group consisting of methotrexate, 2'-deoxycoformycin, methionine sulphoximine, albizziin and β-aspartyl hydroxamate.

The present invention further provides a method of treating B-cell lymphoma, comprising: a) providing: i) a subject having a B-cell lymphoma; ii) a multivalent vaccine comprising at least two recombinant variable regions of immunoglobulin molecules derived from the subjects's B-cell lymphoma cells, wherein the cells express at least two different immunoglobulin molecules, the immunoglobulin molecules differing by at least one idiotope; b) administering said multivalent vaccine to the subject. In a preferred embodiment, the vaccine comprises at least two recombinant immunoglobulin molecules comprising the recombinant variable regions derived from the lymphoma cells. In a preferred embodiment, the method employs a multivalent vaccine which further comprises an adjuvant. When the vaccine is to be administered to a human subject, adjuvants approved for use in humans are employed. In a preferred embodiment the adjuvant is Syntex adjuvant formulation 1. The recombinant Ig proteins (including fragments of Ig proteins) which comprise the multivalent vaccine may be conjugated to a carrier protein such as KLH.

The present invention provides a method of treating B-cell lymphoma, comprising: a) providing: i) a subject having a B-cell lymphoma; ii) a multivalent vaccine comprising at least two recombinant variable regions of immunoglobulin molecules derived from the subjects's B-cell lymphoma cells, wherein the cells express at least two different immunoglobulin molecules, the immunoglobulin molecules differing by at least one idiotope; and iii) dendritic cells isolated from the subject; b) incubating the dendritic cells in vitro with the multivalent vaccine to produce autologous antigen-pulsed dendritic cells; c) administering intravenously the pulsed dendritic cells to the subject; and d) following the administration of the pulsed dendritic cells, administering the multivalent vaccine to the subject. In a preferred embodiment, the vaccine comprises at least two recombinant immunoglobulin molecules comprising the recombinant variable regions.

The present invention further provides a method of treating B-cell lymphoma, comprising: a) providing: i) a subject having a B-cell lymphoma; ii) a vaccine produced according to the methods of the present invention; and b) administering the vaccine to the subject.

Still further, the present invention provides a method of treating a subject having an immune cell tumor, comprising: a) providing: i) immune cell tumor cells isolated from a subject, the tumor cells expressing an idiotype protein on the cell membrane; ii) an amplification vector comprising a first recombinant oligonucleotide having a sequence encoding a first inhibitable enzyme operably linked to a heterologous promoter; iii) a eukaryotic parent cell line; b) isolating nucleotide sequences encoding at least one idiotype protein expressed on the surface of the tumor cells; c) inserting the nucleotide sequences encoding the idiotype protein(s) into at least one vector to produce at least one expression vector capable of expressing the idiotype protein(s); d) introducing the expression vector(s) into the parent cell to generate one or more transformed cells; e) growing the transformed cell in a first aqueous solution containing an inhibitor capable of inhibiting the inhibitable enzyme wherein the concentration of the inhibitor present in the first aqueous solution is sufficient to prevent growth of the parent cell line; f) identifying a transformed cell capable of growth in the first aqueous solution, wherein the transformed cell capable of growth contains an amplified number of copies of the expression vector and an amplified number of copies of the amplification vector and wherein the transformed cell produces the idiotype protein(s) encoded by the expression vector(s); g) isolating the idiotype protein(s) produced by the transformed cell; and h) administering the isolated idiotype protein(s) to the subject.

The method of the present invention is not limited by the nature of the tumor cells. In one embodiment, the tumor cells are T lymphoid cells and the idiotype protein is a T cell receptor or fragment thereof. In another embodiment, the tumor cells are B lymphoid cells and the idiotype protein is an immunoglobulin or fragment thereof.

DEFINITIONS

Figure 1:
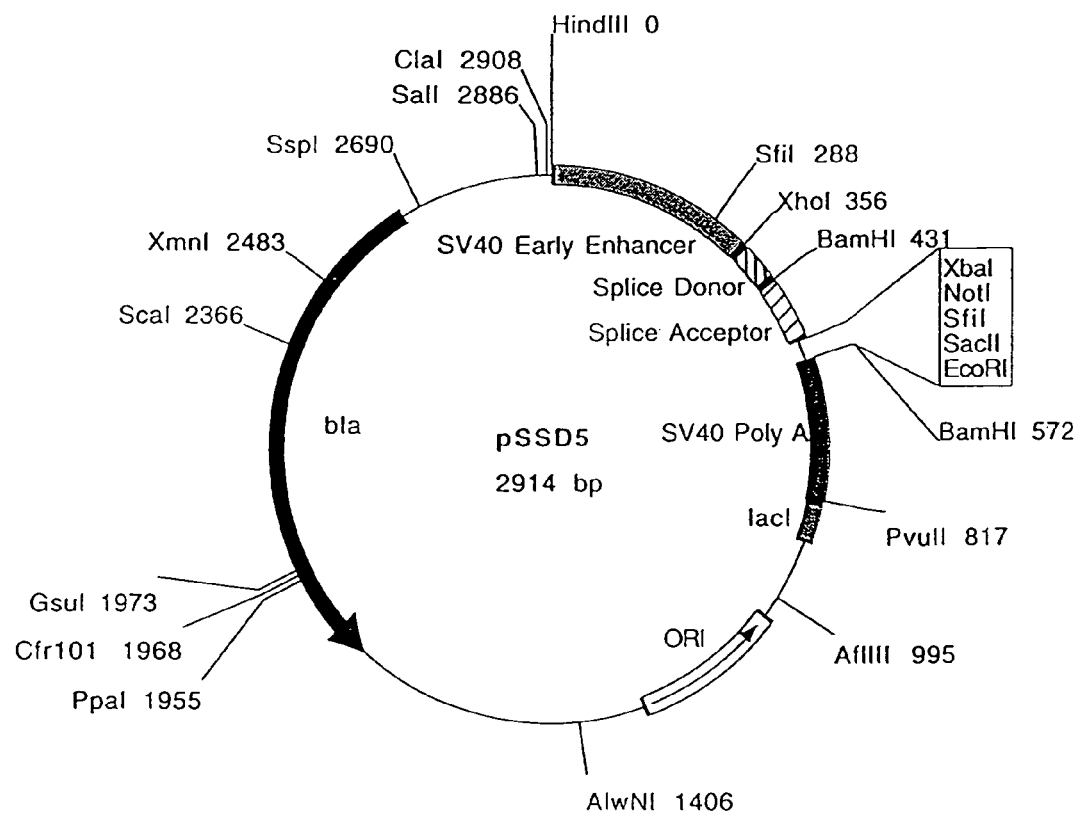
FIG. 1 shows the map of the expression vector pSSD5. Selected restriction enzyme sites are indicated.

To facilitate understanding of the invention, a number of terms are defined below.

The term "recombinant DNA molecule" as used herein refers to a DNA molecule which is comprised of segments of DNA joined together by means of molecular biological techniques.

The terms "in operable combination" or "operably linked" as used herein refers to the linkage of nucleic acid sequences in such a manner that a nucleic acid molecule capable of directing the synthesis of a desired protein molecule is produced. When a promoter sequence is operably linked to sequences encoding a protein, the promoter directs the expression of mRNA which can be translated to produce a functional form of the encoded protein. The term also refers to the linkage of amino acid sequences in such a manner that a functional protein is produced.

DNA molecules are said to have "5' ends" and "3' ends" because mononucleosides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene" means a DNA sequence comprising the coding region of a gene or, in other words, the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The term "recombinant oligonucleotide having a sequence encoding a protein operably linked to a heterologous promoter" or grammatical equivalents indicates that the coding region encoding the protein (e.g., an enzyme) has been joined to a promoter which is not the promoter naturally associated with the coding region in the genome of an organism (i.e., it is linked to an exogenous promoter). The promoter which is naturally associated or linked to a coding region in the genome is referred to as the "endogenous promoter" for that coding region.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element" as used herein refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

Transcriptional control signals in eucaryotes comprise "promoter" and "enhancer" elements. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., Trends Biochem. Sci., 11:287 (1986) and Maniatis, et al., supra (1987)]. For example, the SV40 early gene enhancer is very active in a wide variety of cell types from many mammalian species and has been widely used for the expression of proteins in mammalian cells [Dijkema, et al., EMBO J. 4:761 (1985)]. Two other examples of promoter/enhancer elements active in a broad range of mammalian cell types are those from the human elongation factor 1α gene [Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad. Sci. USA 79:6777 (1982)] and the human cytomegalovirus [Boshart et al., Cell 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site [Sambrook et al., Molecular Cloning: A Laboratory Manual, 2nd ed., Cold Spring Harbor Laboratory Press, New York (1989) pp. 16.7-16.8]. A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation [Sambrook, supra, at 16.6-16.7]. This 237 bp fragment is contained within a 671 bp BamHI/PstI restriction fragment.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with $TK^-$ cell lines, the carbamoyl-phosphate synthetase-aspartate transcarbamoylase-dihydroorotase (CAD) gene which is used in conjunction with CAD-deficient cells and the mammalian hypoxanthine-guanine phosphoribosyl transferase (hprt) gene which is used in conjunction with $HPRT^-$ cell lines. A review of the use of selectable markers in mammalian cell lines is provided in Sambrook et al., supra at pp. 16.9-16.15. It is noted that some selectable markers can be amplified and therefore can be used as amplifiable markers (e.g., the CAD gene).

The term "amplification" or "gene amplification" as used herein refers to a process by which specific DNA sequences are disproportionately replicated such that the amplified gene becomes present in a higher copy number than was initially present in the genome. Gene amplification occurs naturally during development in particular genes such as the amplification of ribosomal genes in amphibian oocytes. Gene amplification may be induced by treating cultured cells with drugs. An example of drug-induced amplification is the methotrexate-induced amplification of the endogenous dhfr gene in mammalian cells [Schmike et al. (1978) Science 202:1051]. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

The term "co-amplification" as used herein refers to the introduction into a single cell of an amplifiable marker in conjunction with other gene sequences (comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

The term "amplifiable marker," "amplifiable gene" or "amplification vector" is used herein to refer to a gene or a vector encoding a gene which permits the amplification of that gene under appropriate growth conditions. Vectors encoding the dihydrofolate reductase (dhfr) gene can be introduced into appropriate cell lines (typically a dhfr$^-$ cell) and grown in the presence of increasing concentrations of the DHFR inhibitor methotrexate to select for cells which have amplified the dhfr gene. The adenosine deaminase (ada) gene has been used in analogous fashion to allow the amplification of ada gene sequences in cells selected for growth in the presence of ADA inhibitors such as 2'-deoxycoformycin. Examples of other genes which can be used as amplifiable markers in mammalian cells include the CAD gene (inhibitor: N-phosphonoacetyl-L-aspartic acid), the ornithine decarboxylase gene (inhibitor: difluoromethylornithine in medium lacking putrescine), and the asparagine synthetase gene (inhibitors: albizziin or β-aspartyl hydroxamate in asparagine-free medium) [see Kaufman, Methods in Enzymol., 185:537 (1990) for a review].

The term "gene of interest" as used herein refers to the gene inserted into the polylinker of an expression vector whose expression in the cell is desired for the purpose of performing further studies on the transfected cell. The gene of interest may encode any protein whose expression is desired in the transfected cell at high levels. The gene of interest is not limited to the examples provided herein; the gene of interest may include cell surface proteins, secreted proteins, ion channels, cytoplasmic proteins, nuclear proteins (e.g., regulatory proteins), mitochondrial proteins, etc.

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The vertebrate hematopoietic system comprises cells of the lymphoid and myeloid lineages. The myeloid lineage (or myeloid-erythroid lineage) gives rise to erythrocytes, basophils, neutrophils, macrophages, eosinophils and platelets. The lymphoid lineage gives rise to B lymphocytes, including plasma cells, and T lymphocytes.

The term "lymphoid" when used in reference to a cell line or a cell, means that the cell line or cell is derived from the lymphoid lineage and includes cells of both the B and the T lymphocyte lineages.

The terms "T lymphocyte" and "T cell" as used herein encompass any cell within the T lymphocyte lineage from T cell precursors (including Thy1 positive cells which have not rearranged the T cell receptor genes) to mature T cells (i.e., single positive for either CD4 or CD8, surface TCR positive cells).

The terms "B lymphocyte" and "B cell" encompasses any cell within the B cell lineage from B cell precursors, such as pre-B cells (B220$^+$ cells which have begun to rearrange Ig heavy chain genes), to mature B cells and plasma cells. "Myeloma" cells or cell lines are malignant plasma cells or cell lines (and are thus in the B cell lineage, not the T cell lineage).

The terms "parent cell line" or "parental cell line" refers to a cell line prior to the addition of exogenous nucleic acid.

The term "transformed cells" refers to cells which contain exogenous DNA (i.e., heterologous DNA introduced into the cells such as the introduction of an expression vector). Terms "transformed cell" and "transfected cell" are used herein interchangeably.

The term "aqueous solution" when used in reference to a solution used to grow a cell line refers to a solution containing compounds required to support the growth of the cells and may contain salts, buffering agents, serum or synthetic serum replacements. An aqueous solution capable of supporting the growth of a cell line is also referred to as "tissue culture medium" (e.g., EMEM, DMEM, RMPI 1470, etc.).

An "aqueous solution which requires the expression of a selectable gene product" is a solution or tissue culture medium which forces a cell line to express a function or active form of the selectable gene product in order for the cells to survive in this medium (e.g., the cell must express a functional HPRT when grown in medium containing hypoxanthine and azaserine). "Aqueous solutions which contain an inhibitor capable of inhibiting an inhibitable enzyme" expressed by a cell refers to medium containing an inhibitor (e.g., methotrexate) which is capable of inhibiting an inhibitable enzyme (e.g., DHFR). The presence of the inhibitor in the medium requires the cell to express a functional or active form of the enzyme which is inhibited by the inhibitor in order to survive.

The "concentration of an inhibitor sufficient to prevent the growth of the parent cell line" refers to that concentration of inhibitor which must be present in the medium to achieve the killing of greater than 98% of the cells within 3 to 5 days after plating the parent cells in medium containing the inhibitor.

The term "amplified number of copies of a vector" refers to a cell line which has incorporated an exogenous or recombinant vector and has increased the number of copies of the vector present in the cell by virtue of the process of gene amplification.

The term "amplified gene" refers to a gene present in multiple copies in a cell line by virtue of gene amplification.

A cell which contains an "endogenous gene encoding an inhibitable enzyme" refers to cell which naturally (as opposed to by virtue of recombinant DNA manipulations) contains in its genomic DNA a gene encoding an inhibitable enzyme; the coding region of this gene will be operably linked to and under the control of its endogenous promoter.

The term "active enzyme" refers to an enzyme which is functional (i.e., capable of carrying out the enzymatic function).

Immunoglobulin molecules consist of heavy (H) and light (L) chains, which comprise highly specific variable regions at their amino termini. The variable (V) regions of the H ($V_H$) and L ($V_L$) chains combine to form the unique antigen recognition or antigen combining site of the immunoglobulin (Ig) protein. The variable regions of an Ig molecule contain determinants (i.e., molecular shapes) that can be recognized as antigens or idiotypes.

The term "idiotype" refers to the set of antigenic or epitopic determinants (i.e., idiotopes) of an immunoglobulin V domain (i.e., the antigen combining site formed by the association of the complementarity determining regions or $V_H$ and $V_L$ regions).

The term "idiotope" refers to a single idiotypic epitope located along a portion of the V region of an immunoglobulin molecule.

The term "anti-idiotypic antibody" or grammatical equivalents refers to an antibody directed against a set of idiotopes on the V region of an Ig protein.

A "multivalent vaccine" when used in reference to a vaccine comprising an idiotypic protein or fragment thereof (e.g., immunoglobulin molecules or variable regions thereof, T cell receptor proteins or variable regions thereof) refers to a vaccine which contains at least two idiotypic proteins which differ by at least one idiotope. For example, a vaccine which contains two or more immunoglobulin molecules derived from a B-cell lymphoma where the immunoglobulin molecules differ from one another by at least one idiotope (e.g., these immunoglobulins are somatic variants of one another) is a multivalent vaccine.

As used herein "recombinant variable regions of immunoglobulin molecules" refers to variable regions of Ig molecules which are produced by molecular biological means. As shown herein, the variable domain of the heavy and light chains may be molecularly cloned from lymphoma cells and expressed in a host cell (e.g., by insertion into an expression vector followed by transfer of the expression vector into a host cell); variable domains expressed in this manner are recombinant variable regions of immunoglobulin molecules. The recombinant variable regions of immunoglobulin molecules may be expressed as an immunoglobulin molecule comprising the recombinant variable regions operably linked to the appropriate constant region (i.e., $C_H$ or $C_L$) (the constant region may comprise the constant region naturally associated with the recombinant variable region, as a Fab, $F(ab')_2$ or Fab' fragment comprising the variable domain of the heavy and light chains, the constant region of the light chain and a portion of the constant region of the heavy chain (the Fab, $F(ab')_2$ or Fab' fragments may be created by digestion of a recombinant immunoglobulin molecule or alternatively, they may be produced by molecular biological means), or alternatively, as a single chain antibody or Fv protein.

"Single-chain antibodies" or "Fv" consist of an antibody light chain variable domain or region ("$V_L$") and heavy chain variable region ("$V_H$") connected by a short peptide linker. The peptide linker allows the structure to assume a conformation which is capable of binding to antigen [Bird et al., (1988) *Science* 242:423 and Huston et al. (1988) *Proc. Natl. Acad. Sci. USA* 85:5879].

A "recombinant variable region derived from a lymphoma cell" refers to a variable region which is molecularly cloned from RNA isolated from a lymphoma cell. The recombinant variable domain may be expressed as an entire immunoglobulin molecule or may be expressed as a fragment of an immunoglobulin molecule, including Fv molecules.

An "immune-enhancing cytokine" is a cytokine that is capable of enhancing the immune response when the cytokine is generated in situ or is administered to a mammalian host. Immune-enhancing cytokine include, but are not limited to, granulocyte-macrophage colony stimulating factor (G-CSF), interleukin-2 (IL-2), interleukin-3 (IL-3), interleukin-4 (IL-4) and interleukin-12 (IL-12).

An "adjuvant" is a compound which enhances or stimulates the immune response when administered with an antigen(s).

"Malignant cells isolated from a patient having a B-cell lymphoma" refers to the malignant or pathogenic B-cells found within the solid tumors characteristic of lymphoma (e.g., lymph nodes and spleen containing the tumor cells).

DESCRIPTION OF THE INVENTION

The invention provides vectors and improved methods for the expression and co-amplification of genes encoding recombinant proteins in cultured cells. The description is divided into the following sections: I) Overview of Co-Amplification Methods; II) Expression Vectors; III) Amplification Vectors; IV) Selection Vectors; V) Cell Lines and Cell Culture; VI) Co-Transfection of Cell Lines; VII) Selection and Co-Amplification; VIII) Co-Amplification Without Prior Selection; IX) High-Level Expression of Interleukin 10 in Amplified Cell Lines; X) High-Level Expression of Human Class II MHC Antigens and T Cell Receptor Proteins in Amplified Cell Lines; and XI) Production of Custom Multivalent Vaccines For the Treatment of Lymphoma and Leukemia.

I. Overview of Co-Amplification Methods

The present invention provides improved methods for the co-amplification of selectable and non-selectable genes in eukaryotic cell lines. The present invention allows, for the first time, the co-amplification of recombinant gene sequences in T lymphoid cell lines (e.g., the BW5147.G.1.4 cell line).

The ability to amplify gene sequences in lymphoid cell lines (T or B lymphoid lines) is desirable for a number of reasons. These include the ability to of these cells to secrete recombinant immunoglobulins and the ability to grow these suspension cell lines at high biomass in fermentators. To date amplification of input gene sequences has been reported only in B lymphoid cell lines (e.g., myeloma cell lines). Further, the ability to amplify genes in myeloma cell lines using the dhfr gene as the amplifiable marker have been problematic due to the endogenous DHFR activity in the myeloma cells. Successful amplification is reported to require the use of a MTX-resistant dhfr gene and the use of very high levels of MTX [Dorai and Moore (1987) J. Immunol. 139:4232]. In contrast, the present invention does not require the use of a MTX-resistant dhfr gene and permits the amplification of genes in T lymphoid cell lines.

A co-amplification scheme employing the glutamine synthetase (GS) gene has been described [U.S. Pat. No. 5,122, 464, the disclosure of which is incorporated by reference herein and Bebbington, et al. (1992) Bio/Technology 10:169]. This co-amplification scheme was developed in part to circumvent the need to use very high levels of MTX and a MTX-resistant dhfr gene to achieve co-amplification of genes in myeloma cells. The use of GS in co-amplification schemes has several drawbacks. First, the propensity of the endogenous GS locus in each cell line to be used must be examined to preclude the use of cell lines in which the endogenous GS locus will amplify at a frequency which makes the GS gene usable. Of four myeloma or hybridoma cell lines, examined, two of the four (50%) were found to be unsuitable host cells for the use of GS as a selectable marker (Bebbington, et al., supra). One of these two unsuitable cell lines, SP2/0, was found to amplify the endogenous GS locus.

A second drawback to the use of GS as a selectable and amplifiable marker is the amount of time required for the isolation of cell lines producing high levels of the non-selected gene product. A single round of amplification and recloning was reported to require 3 months using a myeloma cell line subjected to GS selection (Bebbington, et al., supra). Other selectable markers used in co-amplification protocols have been reported to require even longer periods of time; selection of amplified myeloma cell lines using DHFR as the selectable marker takes up to 6 months [Dorai and Moore (1987) J. Immunol. 139:4232].

The present invention provides methods which allow the isolation of the desired amplified cell lines in a shorter period of time than permitted using existing co-amplification protocols. Multiple rounds of amplification can be achieved using the present invention in a period of about 3 months. The savings in time is realized, in part, by the use of cell lines which have rapid doubling times as the host cell line. In addition to shortening the period required for the generation of the desired amplified cell line, the present methods generate with high frequency amplified cell lines which have co-amplified the non-selectable gene(s) of interest as well as the amplifiable gene (e.g., the dhfr gene).

In general the present invention involves the following steps:

1. Introduction of linearized plasmids comprising an expression vector(s) encoding a protein of interest, an amplification vector encoding an amplifiable marker (e.g., the dhfr gene) and, optionally, a selection vector encoding a selectable marker (e.g., HPRT) into a host cell line. The host cell line will have a doubling time of 12 hours or less; a particularly preferred host cell line is the BW5147.G.1.4 cell line. The host cell prior to the introduction of the linearized vectors is referred to as the parental cell line. A preferred means of introducing the vector DNA into the host cell line is electroporation. The ratio of the amplification vector, non-selectable expression vector(s) and/or selection vector is important. A ratio of 1 (selectable vector): 2 (amplification vector): 20-25 [expression vector(s)] is employed. If a selectable marker is not employed a ratio of 1 (amplification vector): 10-15 [expression vector(s)] is used. The use of this ratio in conjunction with the electroporation of linearized vector DNA produces random concatemers of the transfected DNA vectors which contain a low percentage of the amplifiable gene. While not limiting the invention to any particular mechanism, it is believed that these random concatemers containing a low percentage of the amplifiable gene are less likely to generate an amplification unit composed primarily of the amplifiable marker. It is desirable to produce an amplification unit which contains primarily the expression vector(s) as this results in an amplified cell line which is expressing large quantities of the protein(s) of interest.

In contrast to existing transfection methods (including electroporation protocols), the methods of the present invention employ large quantities of DNA comprising the gene(s) of interest (i.e., the expression vector) [for a discussion of current electroporation methods see Ausubel et al., Current Protocols in Molecular Biology (1995) John Wiley & Sons, Inc., at 9.3.1 to 9.3.6]. Using the methods of the present invention, a total of about 500 to 750 μg of DNA comprising the expression vector(s), the amplification vector and if employed, the selection vector in a total volume of 0.5 ml are introduced into approximately $2 \times 10^7$ cells in 0.5 of the electroporation buffer (final density of DNA is therefore 1 to 1.5 mg/ml). The use of large quantities of the expression vectors increases the frequency with which clones of cells expressing the gene products encoded by the exogenous DNA are isolated. Using the methods of the present invention about 20 to 25% of the selectants (or primary amplificants if no selection vector is employed) express the genes of interest at relatively high levels. In contrast, using conventional amounts of DNA (about 20 to 40 μg when introducing a single expression vector into the cells), only 1 to 5% of the selectants isolated express the gene of interest at relatively high levels.

2. When a selection vector is employed, the transfected cells are allowed to recover by growth in their normal growth medium for a short period (about 36 to 48 hours) and then they are placed in medium which requires the cells to express the selectable marker in order to survive (selective medium). The use of the selective medium facilitates the identification of cells which have taken up the transfected DNA. Colonies of cells which grow in the selective medium (selectants) are expanded and examined for the ability to express the protein of interest. Selectant clones which express the protein(s) of interest at high levels are then subjected to the amplification process.

3. Selectant clones expressing the protein(s) of interest at high levels are examined to determine their level of sensitivity to the inhibitor which inhibits the enzyme encoded by the amplifiable vector. The sensitivity of the parental cell line to the inhibitor is also determined. Selectants which survive growth in medium containing up to a 6-fold higher concentration (typically 4- to 6-fold higher) of the inhibitor than that required to kill the parental cell line are selected for further manipulation (the first round amplificants). [Any primary transfectant which has clearly taken up a transfected amplification vector (e.g., one encoding DHFR) is suitable for continuation with the amplification protocols of the present invention. The presence of the transfected amplification vector is indicated by the ability of the primary transfectant to grow in medium containing the inhibitor at a level which is above the level required to kill the parental cell line.] The first round amplificants are examined for the expression of the protein(s) of interest. Cells which express low levels of the protein of interest are discarded (as this indicates a lack of co-ordinate amplification of the amplifiable gene and the gene(s) of interest). Selectants which are capable of growing in medium containing greater than 6-fold the concentration of inhibitor which prevents the growth of the parental cell line are discarded. It has been found that selectants which are resistant to extremely high levels of the inhibitor typically do not yield amplified cell lines which express high quantities of the protein of interest. While not limiting the present invention to any particular mechanism, it is thought that resistance to extremely high levels of inhibitor at the first round of amplification is indicative of a cell line in which the amplifiable gene sequences readily separate away from the majority of the other input DNA sequences (e.g., the expression vector) resulting the amplification of an amplified unit comprising primarily the amplifiable gene sequences.

4. The first round amplificants which are capable of growing in medium containing 4-fold to 6-fold higher concentrations of the inhibitor than that required to kill the parental cell line are grown in medium containing this level of inhibitor for 2 to 3 weeks. The cells are then grown in medium containing about 4- to 6-fold more of the inhibitor (i.e., 16- to 36-fold the concentration which kills the parental cells) to generate the second round amplificants. The level of expression of the protein(s) of interest are examined in the second round amplificants; any clones which do not show an increase in expression of the protein(s) of interest which corresponds with the increased resistance to the inhibitor are discarded.

5. The amplified cell lines are subjected to subsequent rounds of amplification by increasing the level of inhibitor in the medium 4- to 6-fold for each additional round of amplification. At each round of amplification, the expression of the protein(s) of interest is examined. Typically any discordance between the level of resistance to the inhibitor and the level of expression of the protein(s) if interest is seen on the second round of amplification. Using the methods of the present invention more than 60% of the first round amplificants will co-amplify the gene(s) of interest and the amplifiable gene in the second round of amplification. All clones which co-amplified the gene(s) of interest and the amplifiable gene in the second round of amplification have been found to continue to coordinately amplify these gene sequences in all subsequent rounds of amplification until a maximum expression level was reached.

The following provides additional details regarding the various steps and components employed in the co-amplification protocols of the present invention.

II. Expression Vectors

The expression vectors of the invention comprise a number of genetic elements: A) a plasmid backbone; B) regulatory elements which permit the efficient expression of genes in eukaryotic cells—these include enhancer/promoter elements, poly A signals and splice junctions; C) polylinkers which allow for the easy insertion of a gene (a selectable marker gene, an amplifiable marker gene or a gene of interest) into the expression vector; and D) constructs showing the possible combination of the genetic elements. These genetic elements may be present on the expression vector in a number of configurations and combinations.

A. Plasmid Backbone

The expression vector contains plasmid sequences which allow for the propagation and selection of the vector in procaryotic cells; these plasmid sequences are referred to as the plasmid backbone of the vector. While not intending to limit the invention to a particular plasmid, the following plasmids are preferred. The pUC series of plasmids and their derivatives which contain a bacterial origin of replication (the pMB1 replicon) and the β-lactamase or ampicillin resistance gene. The pUC plasmids, such as pUC18 (ATCC 37253) and pUC19 (ATCC 37254), are particularly preferred as they are expressed at high copy number (500-700) in bacterial hosts. pBR322 and its derivatives which contain the pMB1 replicon and genes which confer ampicillin and tetracycline resistance. pBR322 is expressed at 15-20 copies per bacterial cell. pUC and pBR322 plasmids are commercially available from a number of sources (for example, Gibco BRL, Gaithersburg, Md.).

B. Regulatory Elements i) Enhancer/Promoters

The transcription of each cDNA is directed by genetic elements which allow for high levels of transcription in the host cell. Each cDNA is under the transcriptional control of a promoter and/or enhancer. Promoters and enhancers are short arrays of DNA which direct the transcription of a linked gene. While not intending to limit the invention to the use of any particular promoters and/or enhancer elements, the following are preferred promoter/enhancer elements as they direct high levels of expression of operably linked genes in a wide variety of cell types. The SV40 and SRα enhancer/promoters are particularly preferred when the vector is to be transfected into a host cell which expresses the SV40 T antigen as these enhancer/promoter sequences contain the SV40 origin of replication.

a) The SV40 enhancer/promoter is very active in a wide variety of cell types from many mammalian species [Dijkema, R. et al., EMBO J., 4:761 (1985)].

b) The SRα enhancer/promoter comprises the R-U5 sequences from the LTR of the human T-cell leukemia virus-1 (HTLV-1) and sequences from the SV40 enhancer/promoter [Takebe, Y. et al., Mol. Cell. Biol., 8:466 (1988)]. The HTLV-1 sequences are placed immediately downstream of the SV40 early promoter. These HTLV-1 sequences are located downstream of the transcriptional start site and are present as 5' nontranslated regions on the RNA transcript. The addition of the HTLV-1 sequences increases expression from the SV40 enhancer/promoter.

c) The human cytomegalovirus (CMV) major immediate early gene (IE) enhancer/promoter is active in a broad range of cell types [Boshart et al., Cell 41:521 (1985)]. The 293 cell line (ATCC CRL 1573) [J. Gen. Virol., 36:59 (1977), Virology 77:319 (1977) and Virology 86:10 (1978)], an adenovirus transformed human embryonic kidney cell line, is particularly advantageous as a host cell line for vectors containing the CMV enhancer/promoter as the adenovirus IE gene products increase the level of transcription from the CMV enhancer/promoter.

d) The enhancer/promoter from the LTR of the Moloney leukemia virus is a strong promoter and is active in a broad range of cell types [Laimins et al., Proc. Natl. Acad. Sci. USA 79:6453 (1984)].

e) The enhancer/promoter from the human elongation factor 1α gene is abundantly transcribed in a very broad range of cell types [Uetsuki et al., J. Biol. Chem., 264:5791 (1989) and Mizushima and Nagata, Nuc. Acids. Res. 18:5322 (1990)].

ii) Poly A Elements

The cDNA coding region is followed by a polyadenylation (poly A) element. The preferred poly A elements of the present invention are strong signals that result in efficient termination of transcription and polyadenylation of the RNA transcript. A preferred heterologous poly A element is the SV40 poly A signal (See SEQ ID NO:3). Another preferred heterologous poly A element is the poly A signal from the human elongation factor 1α (hEF1α) gene. (See SEQ ID NO:41). The invention is not limited by the poly A element utilized. The inserted cDNA may utilize its own endogenous poly A element provided that the endogenous element is capable of efficient termination and polyadenylation.

iii) Splice Junctions

The expression vectors also contain a splice junction sequence. Splicing signals mediate the removal of introns from the primary RNA transcript and consist of a splice donor and acceptor site. The presence of splicing signals on an expression vector often results in higher levels of expression of the recombinant transcript. A preferred splice junction is the splice junction from the 16S RNA of SV40. Another preferred splice junction is the splice junction from the hEF1α gene. The invention is not limited by the use of a particular splice junction. The splice donor and acceptor site from any intron-containing gene may be utilized.

C. Polylinkers

The expression vectors contain a polylinker which allows for the easy insertion of DNA segments into the vector. A polylinker is a short synthetic DNA fragment which contains the recognition site for numerous restriction endonucleases. Any desired set of restriction sites may be utilized in a polylinker. Two preferred polylinker sequences are the SD5 and SD7 polylinker sequences. The SD5 polylinker is formed by the SD5A (SEQ ID NO:1) and SD5B (SEQ ID NO:2) oligonucleotides and contains the recognition sites for XbaI, NotI, SfiI, SacII and EcoRI. The SD7 polylinker is formed by the SD7A (SEQ ID NO:4) and SD7B (SEQ ID NO:5) oligonucleotides and contains the following restriction sites: XbaI, EcoRI, MluI, StuI, SacII, SfiI, NotI, BssHII and SphI. The polylinker sequence is located downstream of the enhancer/promoter and splice junction sequences and upstream of the poly A sequence. Insertion of a cDNA or other coding region (i.e., a gene of interest) into the polylinker allows for the transcription of the inserted coding region from the enhancer/promoter and the polyadenylation of the resulting RNA transcript.

D. Constructs

The above elements may be arranged in numerous combinations and configurations to create the expression vectors of the invention. The genetic elements are manipulated using standard techniques of molecular biology known to those skilled in the art [Sambrook, J. et al., *Molecular Cloning: A Laboratory Manual*, 2nd ed., Cold Spring Harbor Laboratory Press, New York (1989)]. Once a suitable recombinant DNA vector has been constructed, the vector is introduced into the desired host cell. DNA molecules are transfected into procaryotic hosts using standard protocols. Briefly the host cells are made competent by treatment with calcium chloride solutions (competent bacteria cells are commercially available and are easily made in the laboratory). This treatment permits the uptake of DNA by the bacterial cell. Another means of introducing DNA into bacterial cells is electroporation in which an electrical pulse is used to permit the uptake of DNA by bacterial cells.

Following the introduction of DNA into a host cell, selective pressure may be applied to isolate those cells which have taken up the DNA. Procaryotic vectors (plasmids) will contain an antibiotic-resistance gene, such as ampicillin, kanamycin or tetracycline resistance genes. The preferred pUC plasmids contain the ampicillin resistance gene. Growth in the presence of the appropriate antibiotic indicates the presence of the vector DNA.

For analysis to confirm correct sequences in the plasmids constructed, the ligation mixture may be used to transform suitable strains of *E. coli*. Examples of commonly used *E. coli* strains include the HB101 strain (Gibco BRL), TG1 and TG2 (derivatives of the JM101 strain), DH10B strain (Gibco BRL) or K12 strain 294 (ATCC No. 31446). Plasmids from the transformants are prepared, analyzed by digestion with restriction endonucleases and/or sequenced by the method of Messing et al., Nuc. Acids Res., 9:309 (1981).

Plasmid DNA is purified from bacterial lysates by chromatography on Qiagen Plasmid Kit columns (Qiagen, Chatsworth, Calif.) according to the manufacturer's directions for large scale preparation.

Small scale preparation (i.e., minipreps) of plasmid DNA is performed by alkaline lysis [Birnboim, H. C. and Doly, J., Nuc. Acids. Res., 7:1513 (1979)]. Briefly, bacteria harboring a plasmid is grown in the presence of the appropriate antibiotic (for pUC-based plasmids ampicillin is used at 60 μg/ml) overnight at 37° C. with shaking. 1.5 ml of the overnight culture is transferred to a 1.5 ml microcentrifuge tube. The bacteria are pelleted by centrifugation at 12,000 g for 30 seconds in a microcentrifuge. The supernatant is removed by aspiration. The bacterial pellet is resuspended in 100 μl of ice-cold Solution I (50 mM glucose, 25 mM Tris-HCl, pH 8.0 and 10 mM EDTA, pH 8.0). Two hundred μl of Solution II (0.2 N NaOH and 1% SDS) is added and the tube is inverted to mix the contents. 150 μl of ice-cold Solution III (3M sodium acetate adjusted to pH 4.8 with glacial acetic acid) is added and the tube is vortexed to mix the contents. The tube is then placed on ice for 3 to 5 minutes. The tube is then centrifuged at 12,000 g for 5 minutes in a microcentrifuge and the supernatant is transferred to a fresh tube. The plasmid DNA is precipitated using 2 volumes of ethanol at room temperature and incubating 2 minutes at room temperature (approximately 25° C.). The DNA is pelleted by centrifugation at 12,000 g for 5 minutes in a microcentrifuge. The supernatant is removed by aspiration and the DNA pellet is resuspended in a suitable buffer such as TE buffer (10 mM Tris-HCl, pH 7.6, 1 mM EDTA, pH 8.0).

Expression vector DNA purified by either chromatography on Qiagen columns or by the alkaline lysis miniprep method is suitable for use in transfection experiments.

III. Amplification Vectors

A vector encoding a structural gene which permits the selection of cells containing multiple or "amplified" copies of the vector encoding the structural gene is referred to as an amplification vector. The amplifiable gene is capable of responding either to an inhibitor or lack of an essential metabolite by amplification to increase the expression product (i.e., the expression of the protein encoded by the amplifiable gene). The amplifiable gene may be characterized as being able to complement an auxotrophic host. For example, the gene encoding DHFR may be used as the amplifiable marker in conjunction with cells lacking the ability to express a functional DHFR enzyme. However, it is not necessary to use an auxotrophic host cell. In a preferred embodiment the host cell is not auxotrophic with respect to the amplifiable marker.

The invention is not limited by the use of a particular amplifiable gene. Various genes may be employed, such as the gene expressing DHFR, the CAD gene, genes expressing metallothioneins, the gene expressing asparagine synthetase, the gene expressing glutamine synthetase and genes expressing surface membrane proteins which offer drug resistance. By blocking a metabolic process in the cells with enzyme inhibitors, such as methotrexate, for DHFR or cytotoxic agents such as metals, with the metallothionein genes, or by maintaining a low or zero concentration of an essential metabolite, the cellular response will be amplification of the particular gene and flanking sequences [Kaufman and Sharp (1982) J. Mol. Biol. 159:601]. Because the process of gene amplification results in the amplification of the amplifiable marker and surrounding DNA sequences, it is possible to co-amplify gene sequences other than those encoding the amplifiable marker [Latt, et al. (1985) Mol. Cell. Biol. 5:1750]. The amplification of sequences encoding the gene of interest is accomplished by co-introducing sequences encoding the gene of interest and the amplifiable marker into the same host cell.

The gene encoding the protein of interest may be physically linked to the amplifiable marker by placing both coding regions with appropriate regulatory signals on a single vector. However it is not necessary that both coding regions be physically located on the same vector. Because small vector molecules are easier to manipulate and give higher yields when grown in bacterial hosts, it is preferred that the gene of interest and the amplifiable marker gene be located on two separate plasmid vectors. Whether the amplifiable marker and the gene of interest are encoded on the same or separate vector plasmids, the vector molecules are linearized by digestion with a restriction enzyme prior to introduction of the vector DNAs into the host cell. The restriction enzyme utilized is selected for its ability to cut within the plasmid backbone of the vector but not cut within the regulatory signals or the coding region of the amplifiable marker or gene of interest.

The amplification vector is constructed by placing the desired structural gene encoding the amplifiable marker into an expression vector such that the regulatory elements present on the expression vector direct the expression of the product of the amplifiable gene. The invention is illustrated by the use of a structural gene encoding DHFR as the amplifiable marker. The DHFR coding sequences are placed in the polylinker region of the expression vector pSSD7 such that the DHFR coding region is under the transcriptional control of the SV40 enhancer/promoter. The invention is not limited by the selection of any particular vector for the construction of the amplification vector. Any suitable expression vector may be utilized. Particularly preferred expression vectors include pSSD5, pSSD7, pSRαSD5, pSRαSD7, pMSD5 and pMSD7. These expression vectors utilize regulatory signals which permit high level expression of inserted genes in a wide variety of cell types.

IV. Selection Vectors

An expression vector encoding a selectable marker gene is referred to as a selection vector. The selectable marker may be a dominant selectable marker. Examples of dominant selectable markers include the neo gene, the hyg gene and the gpt gene. The selectable marker may require the use of a host cell which lacks the ability to express the product encoded by the selectable marker. Examples of such non-dominant markers include the tk gene, the CAD gene and the hprt gene.

The invention is not limited to the use of a particular selectable marker or to the use of any selectable marker (besides the amplifiable marker) at all. In a preferred embodiment, the host cell used is a HPRT-deficient cell line and the amplifiable marker used is DHFR.

When an HPRT-deficient cell line is utilized and this cell line produces a functional DHFR enzyme, a selectable marker encoding the HPRT enzyme may be utilized. The host cell is co-transfected with plasmids containing a selectable marker (HPRT), an amplifiable marker (DHFR) and one or more proteins of interest. The transfected cells are then first selected for the ability to grow in HxAz medium (hypoxanthine and azaserine) which requires the expression of HPRT by the cell. Cells which have the ability to grow in HxAz medium have incorporated at least the selection vector encoding HPRT. Because the vector DNAs are linearized and then introduced into the host cell by electroporation (discussed below), cells which have taken up the HPRT vector are also likely to have taken up the vectors encoding DHFR and the protein of interest. This is because the linearized vectors form long concatemers or tandem arrays which integrate with a very high frequency into the host chromosomal DNA as a single unit [Toneguzzo, et al. (1988) Nucl. Acid Res. 16:5515].

The ability to select for transfected cells expressing HPRT facilitates the use of DHFR as the amplifiable marker in a cell line which is not DHFR-deficient. The use of the selectable marker allows the circumvention of the problem of amplification of the host cell's endogenous DHFR gene [Walls, J. D. et al., (1989), supra]. However, as discussed below, the present invention can be practiced without using a selectable marker in addition to the amplification vector when cell lines which are not DHFR-deficient are employed.

The invention may be practiced such that no selectable marker is used. When the amplifiable marker is a dominant amplifiable marker such as the glutamine synthetase gene or where the host cell line lacks the ability to express the amplifiable marker (such as a DHFR⁻ cell line) no selectable marker need be employed.

V. Cell Lines and Cell Culture

A variety of mammalian cell lines may be employed for the expression of recombinant proteins according to the methods of the resent invention. Exemplary cell lines include CHO cell lines [e.g., CHO-KI cells (ATCC CCl 61; ATCC CRL 9618) and derivations thereof such as DHFR⁻ CHO-KI cell lines (e.g., CHO/dhFr–; ATCC CRL 9096), mouse L cells and BW5147 cells and variants thereof such as BW5147.3 (ATCC TIB 47) and BW5147.G.1.4 cells (ATCC TIB 48). The cell line employed may grow attached to a tissue culture vessel (i.e, attachment-dependent) or may grow in suspension (i.e., attachment-independent).

BW5147.G.1.4 cells are particularly preferred for the practice of the present invention. BW5147.G.1.4 cells have a very rapid doubling time [i.e., a doubling time of about 12 hours when grown in RPMI 1640 medium containing 10% Fetal Clone I (Hyclone)]. The doubling time or generation time refers to the amount of time required for a cell line to increase the number of cells present in the culture by a factor of two. In contrast, the CHO-KI cell line (from which the presently available dhfr– CHO-KI cell lines were derived) have a doubling time of about 21 hours when the cells were grown in either DMEM containing 10% Fetal Clone II (Hyclone) or Ham's F-12 medium containing 10% Fetal Clone II.

A rapid doubling time is advantageous as the more rapidly a cell line doubles, the more rapidly amplified variants of the cell line will appear and produce colonies when grown in medium which requires the expression of the amplifiable marker. Small differences (i.e., 1-2 hours) in the doubling times between cell lines can translate into large difference in the amount of time required to select for a cell line having useful levels of amplification which result in a high level of expression of the non-selectable gene product. The speed with which a high expressing cell line can be isolated may be critical in certain situations. For example, the production of proteins to be used in clinical applications (e.g., the production of tumor-related proteins to be used to immunize a cancer patient) requires that the protein of interest be expressed in useable quantities as quickly as possible so that maximum benefit to the patient is realized.

In addition, BW5147.G.1.4 cells permit the amplification of the non-selectable gene (which encodes the protein of interest) at a very high frequency. Using the methods of the present invention, about 80% of BW5147.G.1.4 cells which survive growth in the selective medium (e.g., HxAz medium) will amplify the input DNA which contains the amplifiable marker and the DNA encoding the protein of interest (as measure by the ability of the cells to survive in medium containing MTX and the production of increased amounts of the protein of interest). That is 80% of the cells which survive growth in the selective medium will survive growth in medium which requires the expression of the amplifiable marker. When cells are subjected to growth in medium containing a compound(s) which requires expression of the amplifiable marker (e.g., growth in the presence of MTX requires the expression of DHFR), the cells which survive are said to have been subjected to a round of amplification. Following the initial or first round of amplification, the cells are placed in medium containing an increased concentration of the compounds which require expression of the amplifiable marker and the cells which survive growth in this increased concentration are said to have survived a second round of amplification. Another round of selection in medium containing yet a further increase in the concentration of the compounds which require expression of the amplifiable marker is referred to as the third round of amplification.

Of those transfected BW5147.G.1.4 clones which amplify in the first round of amplification (as measured by both the ability to grow in increased concentrations of MTX and an increased production of the protein of interest), about ⅔ also coordinately amplify the amplifiable gene as well as the gene encoding the protein of interest in the second round of amplification. All clones which coordinately amplified the amplifiable marker and the gene encoding the protein of interest in the second round of amplification have been found to coordinately amplify both genes in all subsequent rounds of amplification.

An additional advantage of using BW5147.G.1.4 cells is the fact that these cells are very hardy. A cell line is said to be hardy when it is found to be able to grow well under a variety of culture conditions and when it can withstand a certain amount of mal-treatment (i.e., the ability to be revived after being allowed to remain in medium which has exhausted the buffering capacity or which has exhausted certain nutrients). Hardiness denotes that the cell line is easy to work with and it grows robustly. Those skilled in the art of tissue culture know readily that certain cell lines are more hardy than others; BW5147.G.1.4 cells are particularly hardy cells.

BW5147.G.1.4 cells may be maintained by growth in DMEM containing 10% FBS or RPMI 1640 medium containing 10% Fetal Clone I. CHO-KI cells (ATCC CCl 61, ATCC CRL 9618) may be maintained in DMEM containing 10% Fetal Clone II (Hyclone), Ham's F12 medium containing 10% Fetal Clone II or Ham's F12 medium containing 10% FBS and CHO/dhFr– cells (CRL 9096) may be maintained in Iscove's modified Dulbecco's medium containing 0.1 mM hypoxanthine, 0.01 mM thymidine and 10% FBS. These cell lines are grown in a humidified atmosphere containing 5% $CO_2$ at a temperature of 37° C.

The invention is not limited by the choice of a particular host cell line. Any cell line can be employed in the methods of the present invention. Cell lines which have a rapid rate of growth or a low doubling time (i.e., a doubling time of 15 hours or less) and which is capable of amplifying the amplifiable marker at a reasonable rate without amplification of the endogenous locus at a similar or higher rate are preferred. Cell lines which have the ability to amplify the amplifiable marker at a rate which is greater than the rate at which the endogenous locus is amplified are identified by finding that the ability of the cell to grow in increasing concentrations of the inhibitor (i.e., the compound which requires the cell to express the amplifiable marker in order to survive) correlates with an increase in the copy number of the amplifiable marker (this may be measured directly by demonstrating an increase in the copy number of the amplifiable marker by Southern blotting or indirectly by demonstrating an increase in the amount of mRNA produced from the amplifiable marker by Northern blotting).

VI. Co-Transfection of Cell Lines

Prior to introduction of vector DNA into a given cell line, the vector DNA is linearized using a restriction enzyme which cuts once within the vector sequences and which does not cut within the control or coding regions necessary for the expression of the encoded protein. Linearization of the DNA is advantageous as it promotes the integration of the vector DNA into the chromosomal DNA of the host cell line (free ends of DNA are recombinogenic). Furthermore, vector DNA must break in order to integrate into the genomic DNA of the host cell; linearization allows control over where this break occurs thereby preventing the loss of functional vector sequences by directing this break to a non-essential region of the vector. Additionally, linear DNA molecules tend to integrate into the genomic DNA of the host cell as a random head to tail concatemer (it is noted that circular DNA also tends to integrate as a head to tail concatemer; however, as discussed above, the circular DNA must break prior to integration). This obviates the need to construct a single large vector containing the selectable gene, amplifiable gene and the gene(s) of interest. Several smaller vectors may be co-transfected instead thereby essentially eliminating the likelihood that the vector will suffer a break in an essential region.

To generate a stable cell line expressing large quantities of a desired protein(s), the following vectors are introduced as linear DNA: 1) a selectable vector such as pMSD5-HPRT; 2) an amplifiable vector such as pSSD7-DHFR and 3) one or more vectors encoding a gene of interest. This also results in a much higher ration of copies of the expressed gene(s) of interest to amplifiable marker genes in the concatemer. The ratio of the selectable vector, amplifiable vector and the vector(s) encoding a protein(s) of interest is 1:2:20-50. Multiple vectors encoding separate proteins of interest are utilized when it is desirable to express multiple proteins in a single cell. This will be the case where the protein of interest is a multi-chain protein. For example, immunoglobulins are formed by the association of two heavy chains and two light chains; the heavy and light chains are encoded by separate genes. Expression of a functional immunoglobulin requires that the transfected cell express both the heavy and light chain genes. Up to six non-selectable/amplifiable plasmids (i.e., encoding a gene of interest) may be used to transfect a given cell line.

Large quantities of the expression vector(s) are introduced into the cells along with the amplification and selection vectors. Typically 10 to 15 µg of the selectable vector (e.g., pMSD5-HPRT), 20 to 30 µg of the amplification vector (e.g., pSSD7-DHFR) and a total of 400 to 500 µg total of the expression vectors. For example, when two expression vectors are to be used, 200 to 250 µg of each of the two expression vectors (i.e., plasmid encoding a gene of interest) are used in addition to the selection and amplification vectors. The maximum amount of DNA which can be electroporated under the conditions used herein is about 500 to 750 µg DNA (i.e., the total amount or the sum of all vector DNAs). If 6 separate expression vectors are to be introduced into a cell in addition to the selection and amplification vectors, the following amounts of DNA are employed: 7.5 µg of the selection vector, 15 µg of the amplification vector and ~121 µg of each of the six expression vectors [the total amount of DNA is therefore ~750 µg per electroporation using $2 \times 10^7$ cells/ml in 0.5 ml of 1×HBS(EP)].

The vectors to be co-transfected into the cells are linearized using appropriate restriction enzymes (i.e., enzymes which cut only within the plasmid backbone) in the same reaction tube. Following digestion with the appropriate restriction enzymes, the DNA is precipitated using ethanol and resuspended in 0.5 ml of 1×HBS (EP) (20 mM HEPES, pH 7.0; 0.75 mM $Na_2HPO_4/NaH_2PO_4$, pH 7.0; 137 mM NaCl; 5 mM KCl and 1 gm/liter dextrose).

The linearized vector DNAs are preferentially introduced into the host cell by electroporation. Alternatively, the linearized vector DNAs may be introduced into the host cell by microinjection using techniques known to the art. The use of electroporation is preferred over other methods of introducing DNA into cells for a number of reasons: 1) efficiency of transfection. A number of attractive cell lines (e.g., virtually any lymphoid cell line) are refractory to transformation via any other method (such as DEAE-dextran mediated transfection or calcium phosphate-DNA co-precipitation). Electroporation of these lines allows the ready isolation of as many independent transformants as might be reasonably required. 2) Electroporation preserves the integrity of the transfected DNA. DNA introduced by other methods (DEAE-dextran or $CaPO_4$) has been shown to acquire observable mutations at observable frequencies, posing a concern for therapeutically used proteins derived from these sorts of transfections [See for example, M. P. Calos et al. (1983) Proc. Natl. Acad. Sci. USA 80:3015; Kopchick and Stacey (1984) Mol. Cell. Biol. 4:240; Wake et al. (1984) Mol. Cell. Biol. 4:387; and Lebkowski et al. (1984) Mol. Cell. Biol. 4:1951]. Lebkowski et al., supra reported a mutation frequency in DNA chemically introduced that was four orders of magnitude above the endogenous mutational frequency. In contrast, DNA introduced into cells via electroporation was found to have a mutation frequency equal to the background mutational frequency of the cell [Drinkwater and Klinedinst (1986) Proc. Natl. Acad. Sci. USA 83:3402]. 3) Cotransformation of several unlinked DNA molecules is readily achieved using electroporation. As demonstrated herein, a minimum of four unlinked DNAs can be cotransfected into cells by electroporation and a high frequency of the cells expressing the selectable marker will also express all of the other genes. 4) Electroporation is simple to perform. While microinjection of DNA avoids the increased mutation frequency observed using chemical introduction of DNA, microinjection of somatic cells is technically challenging and requires the use of expensive equipment. In contrast electroporation can be performed using fairly inexpensive equipment which may be prepared in house or purchased commercially.

Lymphoid cell lines have been very difficult to transfect with $CaPO_4$-mediated co-precipitation, although it has been achieved [Rice and Baltimore (1982) Proc. Natl. Acad. Sci. USA 79:7862 and Oi et al. (1983) Proc. Natl. Acad. Sci. USA 80:825]. In contrast, transfection of numerous lymphoid cell lines has been achieved by electroporation with acceptably high transformation frequencies [Potter et al. (1984) Proc. Natl. Acad. Sci. USA 81: 7161; Boggs et al. (1986) Exp. Hematol. 14:988; Toneguzzo et al. (1986) Mol. Cell. Biol. 6:703 and Toneguzzo and Keating (1986) Proc. Natl. Acad. Sci. USA 83:3496]. Oi et al., supra report a transformation frequency for BW5147 cells using $CaPO_4$-mediated co-precipitation and a gpt-expressing plasmid of 1 per $10^7$ cells. Toneguzzo et al., supra report a transformation frequency for BW5147 cells using electroporation and a gpt-expressing plasmid of 3.6 per $10^4$ cells (a frequency greater than 3000-fold higher than that achieved using $CaPO_4$-mediated co-precipitation).

The host cells, typically BW5147.G.1.4 cells, are washed twice in ice-cold 1×HBS(EP) and resuspended at $2 \times 10^7$ cells/ml in 0.5 ml of 1×HBS(EP). The cells are then placed in a 1 ml cuvette (#67.746, Sarstedt, Inc., Princeton, N.J.) which contains the linearized DNAs. The cuvette is placed on ice. The electroporation is performed at 225 volts using an ISCO Model 493 power supply (ISCO). The electroporation apparatus is constructed exactly as described in Chu, G. et al., Nucl. Acids Res. 15:1311 (1987). The electroporation device is set on constant voltage (225V) at the 2× setting (i.e., both capacitors are used). Alternatively, a commercially available electroporation device may be employed [e.g., Gene Pulser™ (BioRad, Hercules, Calif.) with the Capacitance Extender set at 960 µFD]. Following electroporation, the cells are allowed to recover by incubation on ice for 5 to 15 minutes, typically 10 minutes.

VII. Selection and Co-Amplification

The electroporated cells are then transferred to a T75 flask (Falcon) containing 30 mls of RPMI 1640 medium (Irvine Scientific) supplemented with 10% fetal calf serum (FCS; HyClone) and 50 µg/ml gentamicin (Sigma). The cells are then incubated at 37° C. in a humidified atmosphere containing 5% $CO_2$ for 36 to 48 hours. The cells are then transferred to 48 well plates (Costar) at $1 \times 10^4$ to $1 \times 10^5$ cells per well in selective medium. The use of selective medium facilitates the identification of cells which have taken up the transfected DNA. Cells which grow either in an attachment-dependent manner or an attachment-independent manner are plated in multiwell plates during growth in selective medium.

A variety of selectable markers may be used including both dominant selectable markers and markers which require the use of a cell line lacking a given enzyme. For example, cell lines lacking the enzyme HPRT can be used in conjunction with a vector expressing the hprt gene. The transfected cells are then grown in the presence of hypoxanthine and azaserine (HxAz medium). Examples of dominant selectable markers which do not require the use of enzyme-deficient cell lines include the neo gene, the hyg gene and the gpt gene.

When pMSD5-HPRT is used as the selectable marker, the selective medium comprises RPMI 1640 medium containing 10% FCS, 100 µM hypoxanthine (Hx) (Sigma) and 2 µg/ml azaserine (Az) (Sigma). After approximately 11 days, positive wells (i.e., wells containing cells capable of growth in the selective medium) are visible and the colonies are removed to 24 well plates. The positive colonies are picked from the 48 well plates from about day 11 to about 3 weeks following the addition of selective medium.

Positive colonies removed from the 48 well plates are placed into 24 well plates (Costar) in RPMI 1640 medium containing 10% dialyzed FCS (HyClone) and 100 µM Hx. The use of dialyzed serum at this point increases the speed and frequency of co-amplification of the input DNA in the transfectants. Hypoxanthine is retained in the culture medium for a few passages until the azaserine is diluted to non-toxic concentrations.

The transfected cells which survived growth in selective medium are then checked to see if they are expressing the genes of interest. This may be done by any suitable assay including cell surface staining, a bioassay for activity, ELISA or immunoprecipitation followed by polyacrylamide gel electrophoresis. For example if the gene(s) of interest encode a cell surface molecule, the transfected cells are analyzed by staining with an antibody specific for the vector-encoded cell surface molecule. The presence of the antibody on the surface of the transfected cell is detected by fluorescence microscopy (the specific antibody is either directly conjugated to a fluorochrome or a fluorescienated secondary antibody is utilized). The best expressing clones are then checked to determine their level of sensitivity to MTX. Typically 6 to 18, more preferably 12, clones are checked.

The parental (i.e., non-transfected) BW5147.G.1.4 cells barely grow in the presence of 10 nM MTX. By visual inspection 3 to 5 days after plating, greater than about 98 percent of the parental BW5147.G.1.4 cells are killed when $1 \times 10^4$ cells are placed in 2 ml of medium containing 20 nM MTX in the well of a 24 well plate (this level of MTX is referred to as the growth cut off for the parental BW5147.G.1.4 cell line). At 30 nM MTX, colonies of BW5147.G.1.4 cells are seen at a frequency of less than $10^{-7}$.

The transfected and selected cells ("selectants") are plated in a range of MTX concentrations ranging from 10 to 100 nM; the cells are plated at a density of 1 to $5 \times 10^4$ cells per well in a 24 well plate (Costar); the selectants are plated at the same density of cells as was used to determine the level of MTX at which >about 98% of the parental cells were killed. This is done because MTX irreversibly binds to DHFR so that the number of cells present in a given volume effects the concentration of MTX required to kill the cells; that is if a higher density of cell is used, a higher concentration of MTX will be required to kill about 98% of the cells [For example when the parental cells are plated at a density of $1 \times 10^4$ cells/2 ml medium in the well of a 24 well plate 20 nM MTX is sufficient to kill >98% cells in a 3 to 5 day assay. If the density is increased two-fold ($1 \times 10^4$ cells in ml medium), 25 nM MTX is required for >98% killing. If $5 \times 10^4$ cells are placed in 2 ml of medium in the well of a 24 well plate, 30 nM MTX is required to achieve >98% killing.]

Clones of selectants typically show growth cut offs of 30 to 60 nM MTX (that is greater than about 98% of the selectants are killed when placed in medium containing 30 to 60 nM MTX when the plates are visually inspected 3 to 5 days after plating in medium containing this level of MTX). Cells from each selectant of interest which shows MTX resistance above the parental BW5147.G.1.4 cells (e.g., above 20 to 30 nM MTX) are plated at $10^4$ cells per well of a 48 well plate (Costar) in 0.5 ml of RPMI 1640 containing 10% dialyzed FCS and MTX (hereinafter medium-MTX). Several concentrations of MTX are used: 20 nM, 40 nM and 60 nM above each clones' upper level of MTX resistance (i.e., if the upper level of MTX resistance is 30 nM then the following concentrations may be used: 50 nM, 70 nM and 90 nM); these levels of MTX are typically 4-fold to 6-fold the level of MTX required to kill greater than about 98% of the parental cells. Any selectants which are capable of growth in medium containing greater than 90 nM MTX are discarded; it has been observed that selectants which are capable of growing in such high levels of MTX tend to preferentially amplify the amplification vector at the expense of the expression vector(s).

After 7 to 10 days, the wells are fed with 0.5 ml medium-MTX. Initial amplificants are picked between 2 to 6 weeks (typically 3 to 5 weeks) after plating in medium-MTX. The clones are then analyzed again for expression of the gene(s) of interest using the appropriate assay (i.e., staining with antibodies for cell surface expression, ELISA, bioassays for activity, immunoprecipitation and PAGE, etc.).

Typically a HPRT$^+$ clone is plated at a concentration of 50 to 80 nM MTX (this represent the first round of amplification). The clone is grown for 2 to 3 weeks and then the level of MTX is increased to 200 nM to 480 nM (a 4 fold increase; this represents the second round of amplification). After another 2 to 4 weeks, the level of MTX is increased to 1 to 2 µM MTX (another 4 to 6 fold increase; this represents the third round of amplification). Any clones which show an increased resistance to MTX without a corresponding increase in expression of the gene(s) of interest is discarded. Typically any discordance is seen on the second round of amplification; such clones prove to be unstable and are undesirable.

The methods of the present invention allow, for the first time, the co-amplification of transfected DNA sequences in BW5147 cells. In addition, the methods of the present invention provide improved methods for the co-amplification of DNA sequences in cell lines. Of the selectants that are expressing the gene(s) of interest, most (i.e., greater than 80%), if not all, will co-amplify the amplifiable marker (e.g, the dhfr gene which confers resistance to MTX) and the gene(s) of interest in the first round of amplification. More than 60% of the first round amplificants will co-amplify the gene(s) of interest in the second round in addition to dhfr gene sequences. To date, using the methods of the present invention, no clones have been obtained that amplify the gene(s) of interest in the second round of amplification that then fail to continue to coordinately amplify in all subsequent rounds until a maximum expression level is reached. Thus, the methods of the present invention result in a much higher frequency of coordinate co-amplification of gene sequences than has been reported for other methods of co-amplification such as that reported by Walls et al. (1989) Gene 81:139 or by Kaufman et al. (1985) Mol. Cell. Biol. 5:1750 when single clones were examined. In addition to providing a means for achieving a very high frequency of coordinate co-amplification of gene sequences, the methods of the present invention also provide methods which produce the desired amplificants with a considerable time savings relative to existing methods. The method of the present invention avoids the time-consuming step of searching through pools of primary transformants which have been subjected to a round of amplification to find those few clones within the pool which are expressing the protein of interest at high levels.

The following modifications to the above-described amplification protocol have been found to decrease the amount of time required for the first round of amplification by 2 to 3 weeks. First, the original transfectants are selected by growth in RPMI 1640 medium containing 100 μM Hx, 2 μg/ml Az and 10% dialyzed FCS. Second, the original transfectants are fed at about 10 days following electroporation with 0.5 ml per well (in a 48 well plate) of RPMI 1640 medium containing 10% dialyzed FCS, 100 μM Hx and 10 nm MTX; this yields a final concentration in each well of the 48 well plate of 5 nM MTX. The net effect of the growth of the transfected cells in medium containing dialyzed FCS and 5 nM MTX is to give the cells which have undergone amplification events a selective advantage.

VIII. Co-Amplification without Prior Selection

The amplified cell lines of the present invention may be generated using only an amplification vector in addition to the expression vector(s) (i.e., the use of a selection vector is not required). Cell lines which do not lack a functional gene product corresponding to the enzyme encoded by the amplification vector and which can be successfully employed without the use of a selectable marker in addition to the amplifiable marker are those cell lines in which the background level of amplification of the endogenous gene (e.g., the endogenous dhfr gene when DHFR is used as the amplifiable marker) is low enough that amplification of the input amplifiable gene (i.e., the amplification vector) occurs preferentially.

When it desired that no selection step be employed, the above protocols are modified as follows. The amplification vector and expression vector(s) are linearized and electroporated into the parental cell line using a ratio of 1:10-15 (amplification vector:expression vector). Again large amounts of DNA are introduced, preferably by electroporation, into the cells. Typically, 20 μg of the amplification vector is used and 200 to 250 μg each of two expression vectors (or 400 to 500 μg of a single expression vector). Following electroporation, the transfected cells are allowed to recover for 36 to 48 hours as described above. The transformed cells are then transferred to 48 well plates at a density of no more than $1 \times 10^6$ cells per well in medium containing 4-fold to 6-fold the concentration of inhibitor required to prevent the growth of the parental cells. Using the BW5147.G.1.4 cell line, the expected frequency of generating a primary transformant which contains enough copies of the input amplifiable gene to allow the isolation of a first round amplicant capable of growth in medium containing 4- to 6-fold the level of inhibitor required to prevent growth of the parental BW5147.G.1.4 cells is approximately 1 in $10^8$ to 1 in $10^{10}$ cells. Accordingly, at least $5 \times 10^8$ to $1 \times 10^{10}$ cells must be plated in medium containing elevated levels of the inhibitor to permit the isolation of several first round amplificants. Cells capable of growing in 4- to 6-fold the level of inhibitor required to prevent growth of the parental cells are examined for the ability to express the protein(s) of interest; those clones expressing high levels of the protein of interest are subjected to subsequent rounds of amplification as described above. Any clones which do not display a coordinate increase in the level of expression of the protein(s) of interest and the level of resistance to the inhibitor at any amplification step are discarded.

The ability to generate amplified cell lines without the need to employ a selection vector reduces the amount of time required to produced the desired amplified cell line. However, the use of a selection vector and the initial selection step is advantageous particularly when working with cell lines which have a high background frequency of amplification of the endogenous locus corresponding to the amplifiable gene present on the amplification vector. Even when working with a cell line which does not a have a high background level of amplification of the endogenous gene, the use of a selection vector and an initial selection step is advantageous because it allows one to work with only the primary selectants expressing the highest levels of the gene(s) of interest. This reduces the amount of time and effort required to generate amplified cell lines expressing very high levels of the protein(s) of interest.

IX. High-Level Expression of Interleukin 10 in Amplified Cell Lines

Using the methods of the present invention, cell lines were isolated which express large quantities of interleukin 10 (IL-10). IL-10 is a cytokine produced by $TH_2$ cells (type 2 helper T cells), macrophages/monocytes, and some B cells. IL-10 acts to inhibit the synthesis of cytokines by activated $TH_1$ cells, activated macrophages and natural killer cells [Mosmann (1993) Ann. Rev. Immunol. 11: 165 and Mosmann (1994) Advances in Immunol. 56: 1]. Studies have shown that IL-10 expression is positively correlated with graft outcome in transplantation [Bromberg (1995) Curr. Op. Immunol. 7:639]. Accordingly, there is interest in using IL-10 therapeutically. Therapeutic use of IL-10, of course, requires the ability to produce large quantities of IL-10.

Presently, there are two commercial sources of murine IL-10. Genzyme Diagnostics (Cambridge, Mass.) sells 5 mg of IL-10 produced in *E. coli* produced for $295.00 (cat#2488-01, ~2500 units). Biosource International (Camarillo, Calif.) sells 5 mg of IL-10 produced in *E. coli* for $245.00 (cat# PMC-0104, ~2500 units). The methods of the present invention were used to isolate cell line which produces about 75,000 units per milliliter of culture supernatant. Using the lower commercial price for IL-10, these cells produce about $7,350,000.00 worth of IL-10 per liter in a static culture. These amplified cell lines yield about 150 mg of IL-10 protein per liter in static culture; thus, the unpurified culture supernatant from these amplified cell lines provides a much more pure source of IL-10 than do presently available commercial preparations.

X. High-Level Expression of Human Class II MHC Antigens and T Cell Receptor Proteins in Amplified Cell Lines The human class II MHC antigens, HLA-DR, and their corresponding mouse analogs, the Ia antigens, are cell surface membrane glycoproteins which mediate the recognition of non-self molecules (i.e., antigens) by T lymphocytes. Class II molecules display fragments of foreign antigens on the surface of antigen presenting cells which include macrophages, dendritic cells, B lymphocytes and activated T lymphocytes. When MHC-restricted, antigen-specific T lymphocytes interact with antigen presenting cells bearing class II molecules bound to antigen, an immune response is generated.

Class II antigens comprise two chains, an α chain and a β chain. Both chains must be expressed in the same cell in order for the class II molecule to be transported to the surface of the cell. The β chain is highly polymorphic and this polymorphism results in heritable differences in immune responsiveness. In certain class II MHC molecules (e.g., mouse IA, human DQ and DP), the α chain is also highly polymorphic. Given the central role that class II molecules play in the immune response, including rejection of transplanted tissue and heritable susceptibility to autoimmune disease, studies of the interaction of class II molecules with foreign antigen and with T lymphocytes have been undertaken. These studies of the physical-chemical interaction of class II molecules with antigen require the availability of large quantities of purified soluble class II molecules. In addition, the use of class II molecules complexed with specific peptides has been suggested for the treatment of autoimmune disease [Sharma, et al. (1991) Proc. Natl. Acad. Sci. USA 88:11465].

In order to provide such reagents, chimeric human DR molecules were expressed at high levels on the surface of amplified cell lines using the selection amplification method of the invention. The DR molecules are cleaved from the cell surface to produce soluble DR molecules by treatment with an enzyme capable of cleaving either a phosphatidylinositol linkage or a thrombin site which is present on the chimeric DR molecule.

A similar approach allows the production of large quantities of soluble T cell receptor (TCR) molecules or immunoglobulin (Ig) molecules. Like, class II molecules, TCR and Ig molecules comprise heterodimers (i.e., two different chains associate to form the TCR or Ig molecule displayed on the cell surface; it is noted that both cell surface and soluble forms of Ig molecules exist in nature and for patient immunization one would produce soluble Ig). The methods of the present invention permit the production of large quantities of soluble forms of class II MHC molecules and TCR to be produced in a rapid manner. This allowing for the production of customized tumor cell vaccines comprising soluble TCR for the treatment of lymphoma and leukemia patients as well as the production of soluble class II MHC molecules for the treatment of autoimmune disease.

XI. Production of Custom Multivalent Vaccines for the Treatment of Lymphoma and Leukemia The existing approach toward vaccination (i.e., active immunotherapy) of B-cell lymphoma and leukemia involves the production of a custom vaccine comprising autologous immunoglobulin idiotype which corresponds to the most abundant antibody molecule expressed on the surface of the B-cell tumor. An analogous approach for the treatment of T-cell lymphomas and leukemias would involve the production of a custom vaccine comprising autologous T cell receptor (TCR) idiotype which corresponds to the most abundant TCR molecule expressed on the surface of the T-cell tumor.

It is known in B-cells that the variable regions of rearranged immunoglobulin (Ig) genes accumulate point mutations following antigenic stimulation (Ig). This process, known as somatic mutation or somatic hypermutation, is responsible for affinity maturation of humoral immune responses [Tonegawa (1983) Nature 302:575, Teillaud et al. (1983) Science 222:721, Griffiths et al. (1984) Nature 312: 272 and Clarke et al. (1985) J. Exp. Med. 161:687]. During affinity maturation, antibodies of higher affinity emerge as the immune response proceeds (i.e., progression from primary to secondary to tertiary responses). A comparison of the antibody produced during the immune response reveals that mutations accumulate from the late stage of primary responses onward; these mutations cluster in the second complementarity determining region (CDR2) region of the Ig molecule (i.e., within the hypervariable regions within the antigen-binding site). Somatic mutation does not occur in T cells.

Somatic variants are known to exist within the population of cells comprising certain B-cell tumors (e.g., low grade or follicular B-cell lymphomas); thus, while these tumors are clonal at the level of Ig gene rearrangements (including nucleotide sequence at the V-D-J junctions) they are in fact quasi-clonal with respect to the nucleotide or amino acid sequence of their heavy chain V regions [Cleary M L et al. (1986), Cell 44:97 and Levy S et al. (1988) J. Exp. Med. 168:475]. It is thought that following the transformation event(s) which gives rise to the B-cell tumor, somatic mutation persists. Analysis of B-cell lymphomas reveals that about 1 to 5% of the cells within the tumor contain somatic mutations.

The fact that somatic variants exist within a B-cell tumor has implications for immunotherapy of these tumors. For example, treatment of B-cell lymphoma with anti-idiotype antibodies was shown to produce an initial partial response in patients; however, idiotype variant tumor cells (idiotype negative) emerged at the original tumor site [Cleary M L et al. (1986), supra; Bahler D W and Levy R (1992) Proc. Natl. Acad. Sci. USA 89:6770; Zelenetz A D et al. (1992) J. Exp. Med. 176:1137; and Zhu D et al. (1994) Brit. J. Haematol. 86:505]. It is thought that these idiotype variant tumor cells were already present before treatment with the monoclonal anti-idiotype antibody and that they were allowed to proliferate after the selective removal of the idiotype positive tumor cells. These clinical trials showed the drawback of targeting a single epitope on the tumor cell.

In order to improve the immunotherapy of B-cell tumors, active immunization with autologous tumor derived Ig or Ig subfragments has been employed. It is hoped that the use of the Ig or Ig subfragments as an immunogen would produce a T cell response and antibodies directed against a number of different epitopes found within the tumor-specific Ig. In this type of treatment the Ig (or idiotype fragment of the Ig) of the patient's tumor cell is expressed. While this approach has the advantage that multiple epitopes are targeted, it still suffers from the fact that a single Ig (or subfragment) is used as the immunogen and therefore the possibility exists that tumor cells expressing somatic variants of the predominant Ig will escape and proliferate. To produce the tumor Ig-idiotype protein used for immunization with existing methodologies, lymphoma cells removed by surgical biopsy are fused with the heterohybridoma cell line K6H6/B5 which has lost the ability to secrete endogenous Ig. Hybrid cells which secrete Ig corresponding to the immunophenotype of the tumor sample are expanded and the secreted Ig is purified for use as a vaccine [Kwak et al. (1992), supra]. This technique is referred to as "rescue fusion." The Ig produced by rescue fusion represents a single Ig derived from the patient's tumor; this Ig is presumably the predominant Ig expressed by the tumor. Thus, vaccines produced by rescue fusion are monovalent and do not represent the full complexity of Ig expressed by tumors which contain somatic variants.

Clinical trials using tumor Ig-idiotype protein produced by rescue fusion to vaccinate B-cell lymphoma patients are in progress. These trials are showing impressive clinical improvements for these tumors which remain essentially incurable with conventional therapy (i.e., chemotherapy). This custom vaccine therapy is used following a course of conventional chemotherapy (employed to reduce the tumor burden). The clinical improvements are seen when comparing patients treated solely with conventional chemotherapy with patients who received custom vaccines following chemotherapy. Among the patients who have been treated with custom vaccines and followed for a lengthy period of time (about 8 years), one has recently relapsed. Although not confirmed at this time, it is possible that this relapse is due to the outgrowth of tumor cells bearing somatic variants of the tumor Ig-idiotype protein used in the vaccine.

In addition to the failure to provide a multivalent vaccine representative of all Ig variants present in the patients tumor, the rescue fusion technique has other draw backs. This technique requires a large number of tumor cells which are obtained by surgical biopsy of enlarged lymph nodes in the patient. Some B-cell lymphoma patients do not present with enlarged lymph nodes suitable for surgical biopsy and therefore cannot be treated using vaccines produced by the rescue fusion technique. Furthermore, the production of each custom heterohybridoma cell line secreting the patients Ig takes between 2 to 8 months (average of 4 months) and is labor intensive; in laboratories having extensive experience with the rescue fusion technique, the rate of vaccine production is about 25 custom vaccines per technician per-year. This rate of producing custom vaccines is not sufficient to meet the existing and growing patient demand.

Ideally, the method for producing custom tumor specific vaccines could be performed on a small number of cells (i.e., from a fine needle biopsy), would produce a multivalent vaccine representative of the full complexity of the patient's tumor, would be fast (average of 2-3 months) and would be less labor intensive than existing methods such that a single technician could produce at least a hundred custom vaccines per year.

The methods described herein (Examples 9 and 10) provide a means to produce custom vaccines, including multivalent vaccines, from small numbers of cells quickly and efficiently. The ability to use a small sample size permits the production of custom vaccines for patients lacking enlarged lymph nodes suitable for surgical biopsy. In addition to expanding the pool of patients who can be treated with custom vaccines, the ability to use fine needle biopsy material obviates the need for surgery for all lymphoma patients (at least with respect to the collection of cells for the production of custom vaccines).

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade); AMP (adenosine 5'-monophosphate); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); g (gravity); OD (optical density); HEPES (N-[2-Hydroxyethyl] piperazine-N-[2-ethanesulfonic acid]); HBS (HEPES buffered saline); SDS (sodium dodecylsulfate); Tris-HCl (tris [Hydroxymethyl]aminomethane-hydrochloride); Klenow (DNA polymerase I large (Klenow) fragment); rpm (revolutions per minute); EGTA (ethylene glycol-bis(β-aminoethyl ether)N,N,N',N'-tetraacetic acid); EDTA (ethylenediaminetetracetic acid); bla (β-lactamase or ampicillin-resistance gene); ORI (plasmid origin of replication); lacI (lac repressor); Amicon (Amicon Corp., Beverly, Mass.); ATCC (American Type Culture Collection, Rockville, Md.); Becton Dickinson (Becton Dickinson Immunocytometry Division, San Jose Calif.); Costar (Costar, Cambridge, Mass.); Falcon (division of Becton Dickinson Labware, Lincoln Park, N.J.); FMC (FMC Bioproducts, Rockland, Me.); Gibco/BRL (Gibco/BRL, Grand Island, N.Y.); HyClone (HyClone, Logan, Utah); Sigma (Sigma Chemical Co., St. Louis, Mo.); NEB (New England Biolabs, Inc., Beverly, Mass.); Operon (Operon Technologies, Alameda, Calif.); Perkin-Elmer (Perkin-Elmer, Norwalk, Conn.); Pharmacia (Pharmacia Biotech, Pisacataway, N.J.); Promega (Promega Corp., Madison, Wis.); Sarstedt (Sarstedt, Newton, N.C.); Stratagene (Stratagene, LaJolla, Calif.); U.S. Biochemicals (United States Biochemical, Cleveland, Ohio); and Vector (Vector Laboratories, Burlingame, Calif.).

EXAMPLE 1

Construction of Expression Vectors

In order to construct the expression vectors of the invention a number of intermediate vectors were first constructed.

Construction of pSSD5 And pSSD7 pSSD5 and pSSD7 contain the following elements from SV40: the enhancer/promoter region, the 16S splice donor and acceptor and the poly A site. Vectors containing the SV40 enhancer/promoter sequences will replicate extrachromosomally in cell lines which express the SV40 large T antigen as the SV40 enhancer/promoter sequences contain the SV40 origin of replication.

A polylinker containing the recognition sequences for several restriction enzymes is located between the splice acceptor and poly A sequences. The polylinker allows for the easy insertion of a gene of interest. The gene of interest will be under the transcriptional control of the SV40 enhancer/promotor. pSSD5 and pSSD7 differ only in the sequences of the polylinker (sequences listed below). The polylinker of pSSD5 contains the following restriction sites: XbaI, NotI, SfiI, SacII and EcoRI. The polylinker of pSSD7 contains the following restriction sites: XbaI, EcoRI, MluI, StuI, SacII, SfiI, NotI, BssHII and SphI.

pSSD5 was constructed by digestion of the plasmid pL1 [Okayama and Berg, Mol. Cell. Biol., 3:280 (1983)] with PstI and HindIII. All restriction enzymes were obtained from New England Biolabs and were used according to the manufacturer's directions. The plasmid pcDV1 [Okayama and Berg, supra] was digested with HindIII and BamHI. Both digests were electrophoresed on a 0.8% low melting temperature agarose gel (SeaPlaque, FMC). A 535 bp DNA fragment from the pL1 digest containing the SV40 enhancer/promoter and 16S splice junctions was cut out of the gel. A 2.57 kb DNA fragment from the pcDV1 digest containing the SV40 polyadenylation signals and the pBR322 backbone was cut out of the gel. The two gel slices were combined in a microcentrifuge tube and the agarose was removed by digestion with β-Agarase I (NEB) followed by isopropanol precipitation according to the manufacturer's directions. The DNA pellets were dried and resuspended in 20 μl of TE.

Two synthetic oligonucleotides (Operon), SD5A [5'-TCTAGAGCGGCCGCG GAGGCCGAATTCG-3' (SEQ ID NO:1)] and SD5B [5'-GATCCGAATTCGGCCT CCGCG-GCCGCTCTAGATGCA-3' (SEQ ID NO:2)] were added in equal molar amounts to the resuspended DNA fragments. Ligation buffer (10× concentrate, NEB) was added to a 1× concentration, 80 units of T4 DNA ligase was added and the ligation was placed at 14° C. overnight. Competent *E. coli* cells were transformed with the ligation mixture and a plasmid was isolated that consisted of the DNA fragments from pL1 and pcDV1 with a novel polylinker connecting the fragments. The resulting plasmid was named pSSD.

The ~670 bp BamHI/PstI fragment containing the SV40 poly A sequences (SV40 map units 2533 to 3204; SEQ ID NO:3) was removed from SV40 DNA and cloned into pUC19 digested with BamHI and PstI. The resulting plasmid was then digested with BclI (corresponds to SV40 map unit 2770). The ends were treated with the Klenow enzyme (NEB) and dNTPs to create blunt ends. Unphosphorylated PvuII linkers (NEB) were ligated to the blunted ends and the plasmid was circularized to create pUCSSD. The SV40 poly A sequences can be removed from pUCSSD as a BamHI/PvuII fragment.

pSSD5 was constructed by ligating together the following three fragments: 1) the 1873 bp SspI/PvuII fragment from pUC19; this provides the plasmid backbone; 2) the 562 bp fragment containing the SV40 enhancer/promoter and 16S splice junction and the polylinker from pSSD; this fragment was obtained by digestion of pSSD with SspI and partial digestion with BamHI followed by isolation on low melting agarose and recovery as described above; and 3) the 245 bp BamHI/PvuII fragment from pUCSSD (this fragment contains the SV40 poly A sequences). The three fragments were mixed together and ligated using T4 DNA ligase (NEB) to create pSSD5. The map of pSSD5 is shown in FIG. 1.

Figure 2:
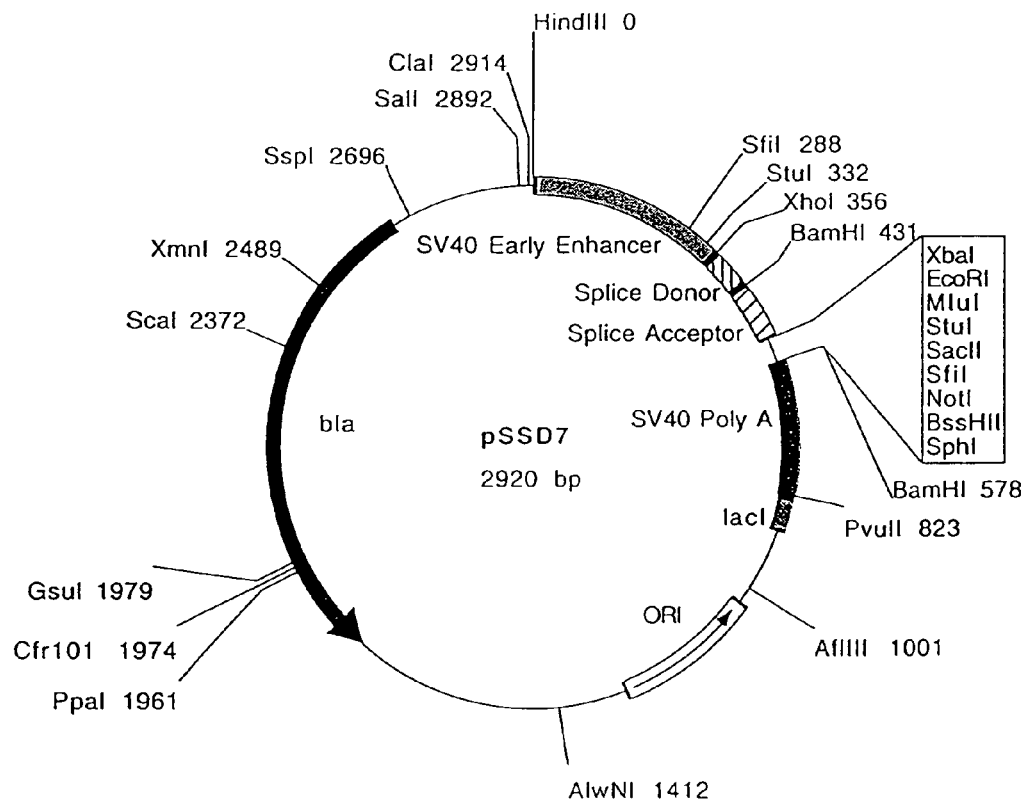
FIG. 2 shows the map of the expression vector pSSD7. Selected restriction enzyme sites are indicated.

To create pSSD7, pSSD5 was digested with XbaI and EcoRI. The synthetic oligonucleotide pair SD7A and SD7B (Operon) was ligated into the cut pSSD5 thereby generating the SD7 polylinker. The sequence of SD7A is 5'-CTAGAATTC ACGCGTAGGCCTCCGCGGCCGCGCG-CATGC-3' (SEQ ID NO:4). The sequence of SD7B is 5'-AATTGCATGCGCGCGGCCGCGGAGGC-CTACGCGTGA ATT-3' (SEQ ID NO:5). The map of pSSD7 is shown in FIG. 2.

Construction of pSRαSD5 and pSRαSD7 pSRαSD5 and pSRαSD7 contain the SRα enhancer/promoter followed by the 16S splice junction of SV40 and either the polylinker formed by the oligonucleotide pair SD5A/SD5B or SD7A/SD7B. The polylinker is followed by the SV40 poly A sequences. A gene of interest can be inserted into the polylinker and the expression of the inserted gene will be under the control of the human SRα enhancer/promoter. The SRα enhancer/promoters a hybrid enhancer/promoter comprising human T cell leukemia virus 15' untranslated sequences and the SV40 enhancer [Takebe et al., Mol. Cell. Biol., 8:466 (1988)]. The SRα enhancer/promoter is reported to increase expression from the SV40 enhancer/promoter by ten-fold in host cells. This enhancer/promoter is active in a broad range of cell types. Vectors containing the SRα enhancer/promoter will replicate in cells expressing SV40 large T antigen as the SV40 origin of replication is present within the SRα enhancer/promoter sequences.

Figure 3:
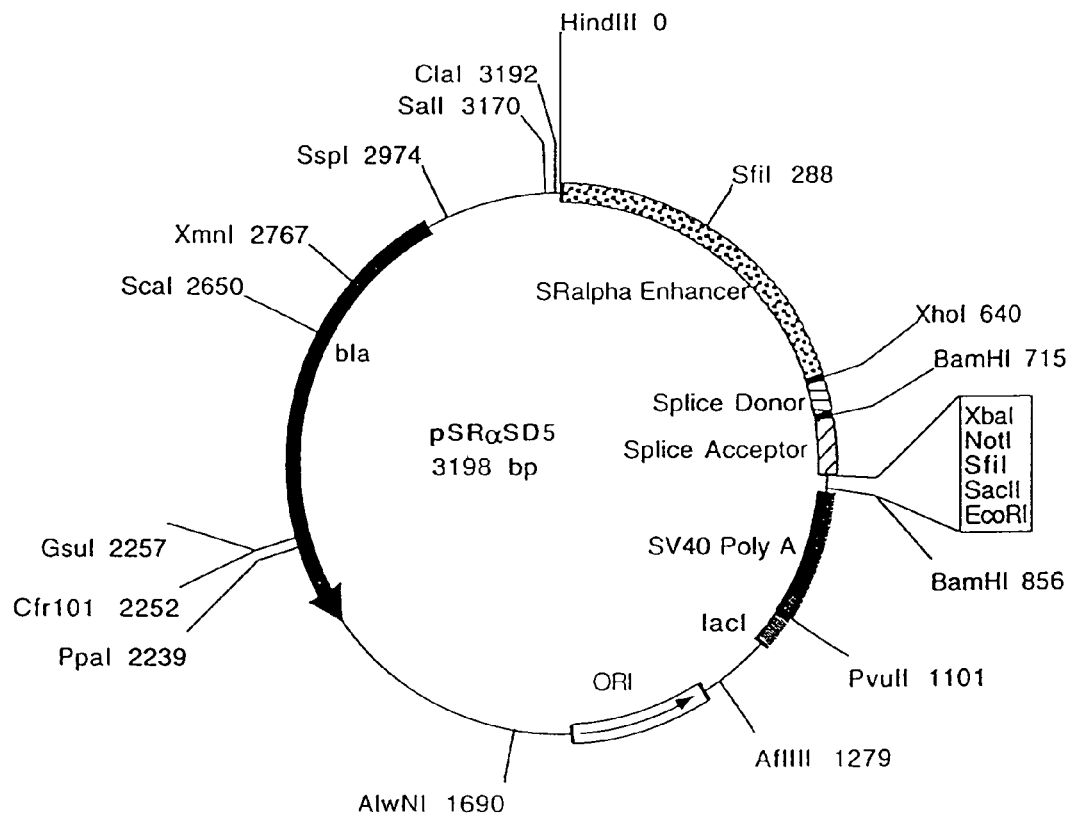
FIG. 3 shows the map of the expression vector pSRαSD5. Selected restriction enzyme sites are indicated.
Figure 4:
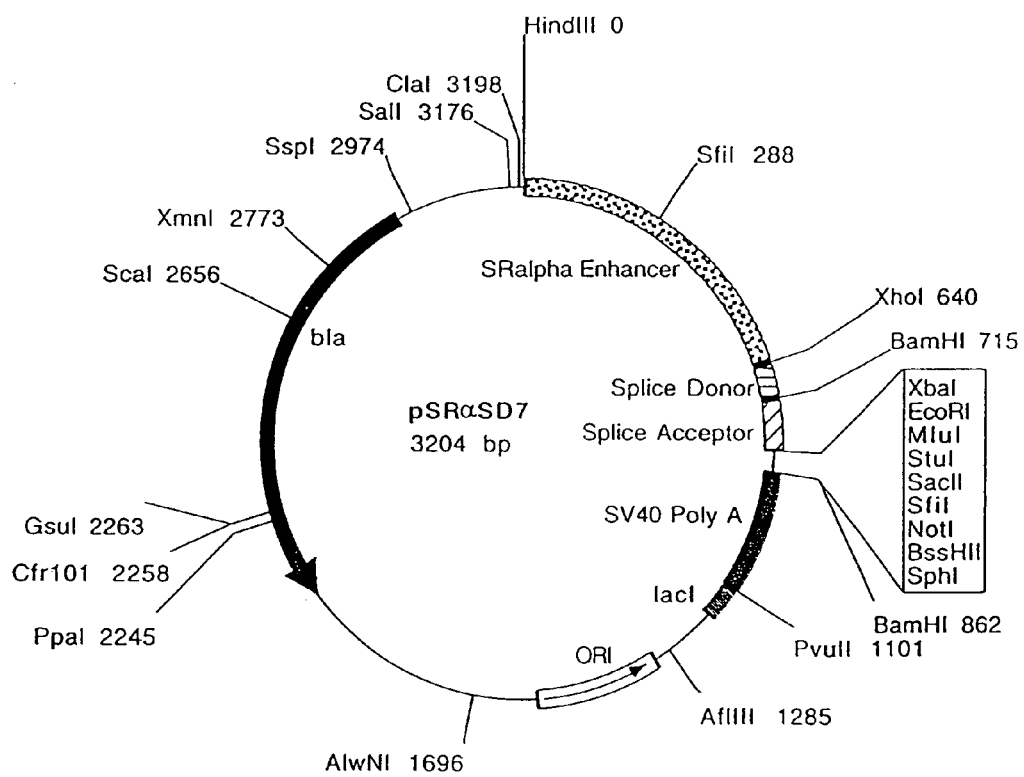
FIG. 4 shows the map of the expression vector pSRαSD7. Selected restriction enzyme sites are indicated.

The SRα enhancer/promoter was removed from pcDL-SRα296 by digestion with HindIII and XhoI. The ~640 bp HindIII/XhoI fragment (SEQ ID NO:6) was recovered from a low melting agarose gel as described above. This ~640 bp fragment was inserted into either pSSD5 or pSSD7 digested with HindIII and XhoI (removes the SV40 enhancer/promoter from pSSD5 or pSSD7). The map of pSRαSD5 is shown in FIG. 3. The map of pSRαSD7 is shown in FIG. 4.

Construction of pMSD5 and pMSD7 pMSD5 and pMSD7 contain the long terminal repeat (LTR) from the Moloney murine leukemia virus followed by the 16S splice junction of SV40 and either the polylinker formed by the oligonucleotide pair SD5A/SD5B or SD7A/SD7B. The polylinker is followed by the SV40 poly A sequences. A gene can be inserted into the polylinker and the expression of the inserted gene will be under the control of the Moloney LTR.

Figure 5:
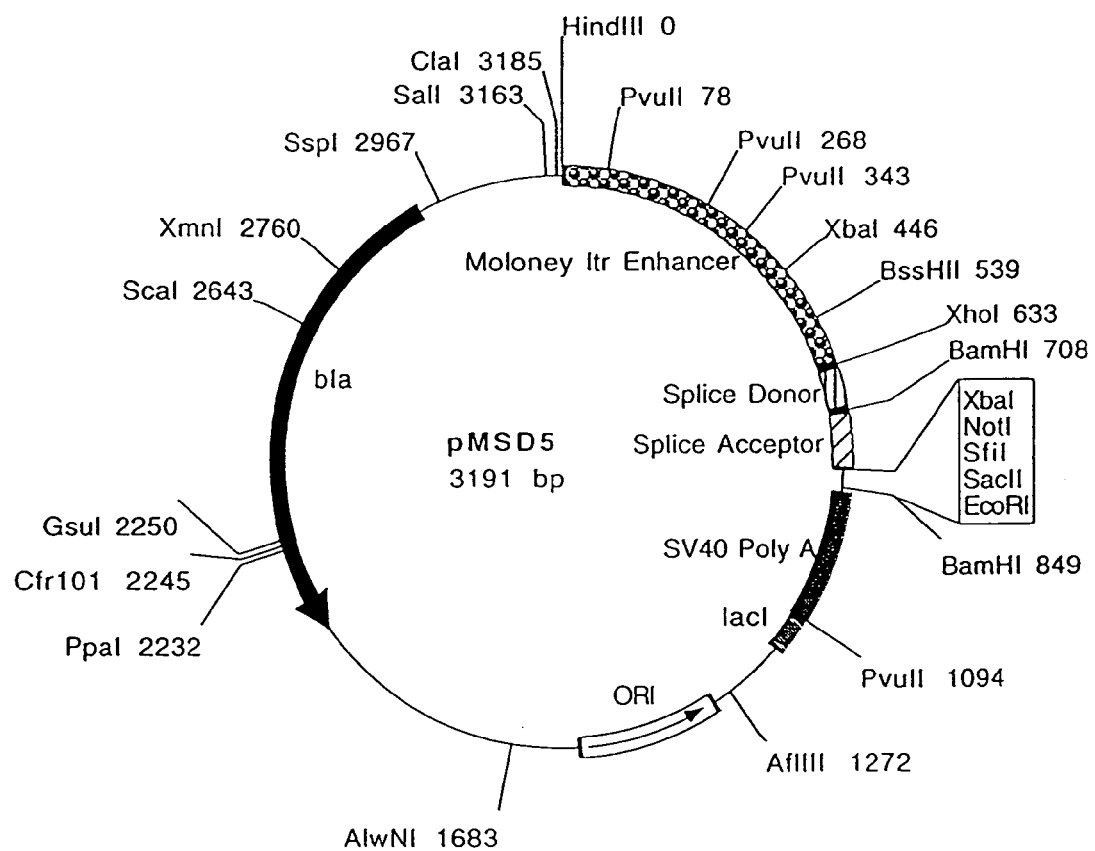
FIG. 5 shows the map of the expression vector pMSD5. Selected restriction enzyme sites are indicated.

The Moloney LTR was removed from a plasmid containing Moloney murine leukemia viral DNA [Shinnick et al., Nature 293:543 (1981)] by digestion of the plasmid with ClaI (corresponds to Moloney map unit 7674). The ends were made blunt by incubation with Klenow and dNTPs. Unphosphorylated HindIII linkers (NEB) were ligated onto the blunt ends. This treatment destroyed the ClaI site and replaced it with a HindIII site. The plasmid was then digested with SmaI (corresponds to Moloney map unit 8292) and unphosphorylated XhoI linkers were ligated onto the ends. The resulting plasmid now contains a XhoI site replacing the SmaI site at Moloney map unit 8292 and a HindIII site replacing the ClaI site at Moloney map unit 7674. The plasmid was then digested with XhoI and HindIII. The resulting XhoI/HindIII fragment containing the Moloney LTR (SEQ ID NO:7) was inserted into pSSD5 digested with XhoI and HindIII (this removes the SV40 enhancer/promoter and 16S splice junction from pSSD5) to yield pMSD5. The map of pMSD5 is shown in FIG. 5.

Figure 6:
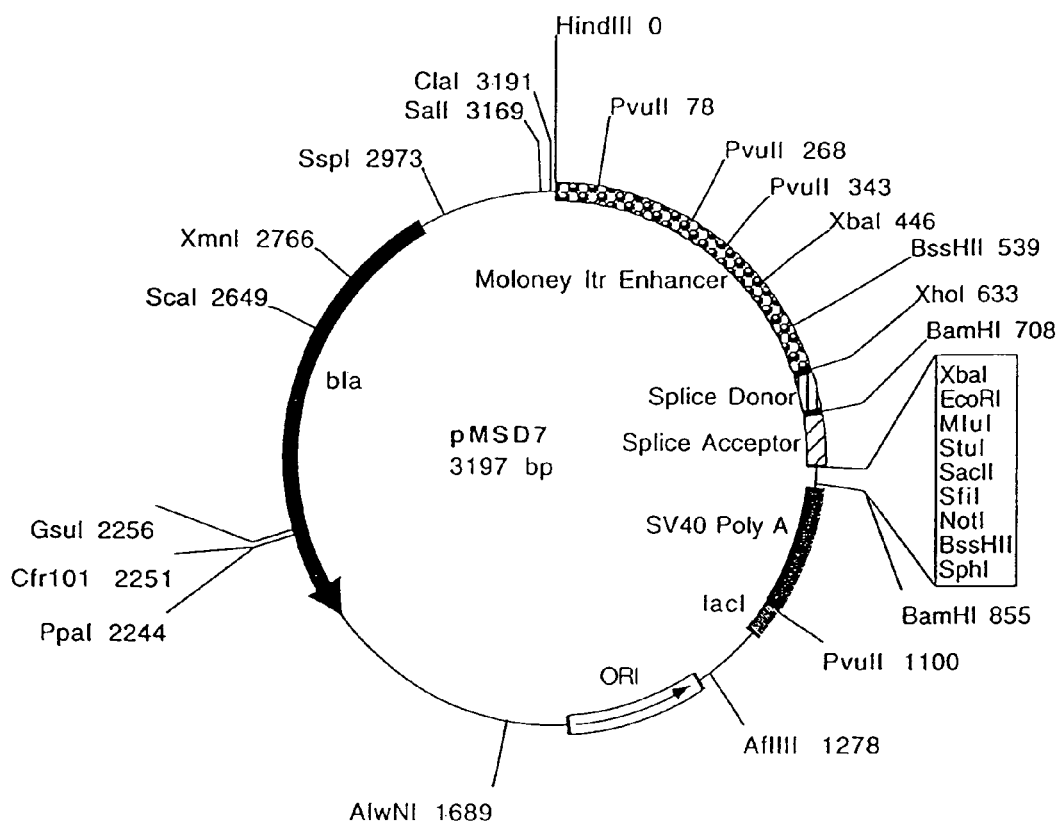
FIG. 6 shows the map of the expression vector pMSD7. Selected restriction enzyme sites are indicated.

To create pMSD7, the Moloney LTR on the XhoI/HindIII fragment was inserted into pSSD7 digested with XhoI and HindIII. The map of pMSD7 is shown in FIG. 6.

Construction of Vectors Containing the Human Elongation Factor 1α Enhancer/Promoter The human elongation factor 1α enhancer/promoter is abundantly transcribed in a very broad range of cell types. Vectors containing two versions of this active enhancer/promoter were constructed: 1) a long version containing ~1.45 kb of sequences located upstream of the initiation codon and continuing through the first intron to provide a splice junction and 2) a short version containing 475 bp of sequences upstream of the initiation codon. The short version of the promoter is termed the "A" version and the long version is termed the "B" version.

A. Construction of pHEF1αASD5 and pHEF1αASD7 pHEF1αASD5 and pHEF1αASD7 contain the short version of the human elongation factor 1α enhancer/promoter [Uetsuki et al., J. Biol. Chem., 264:5791 (1989) and Mizushima and Nagata, Nuc. Acids. Res., 18:5322 (1990)]. The human elongation factor 1α enhancer/promoter is abundantly transcribed in a very broad range of cell types including L929, HeLa, CHU-2 and COS cells.

The human elongation factor 1α enhancer/promoter (nucleotides 125 to 600 of the human elongation factor 1α gene; SEQ ID NO:8) was isolated from human genomic DNA as follows. Genomic DNA was isolated from the MOU cell line (GM 08605, NIGMS Human Genetic Mutant Cell Repository, Camden, N.J.) using standard techniques [Sambrook et al., supra at pp. 9.16-9.23]. The MOU cell line is an Epstein-Barr virus transformed human B cell line.

Two synthetic oligonucleotide primers (Operon) were used to prime the polymerase chain reaction (PCR) for the isolation of an ~475 bp fragment containing the human elongation factor 1α enhancer/promoter (SEQ ID NO:8). U.S. Pat. Nos. 4,683,195, 4,683,202 and 4,965,188 cover PCR methodology and are incorporated herein by reference.

Figure 7:
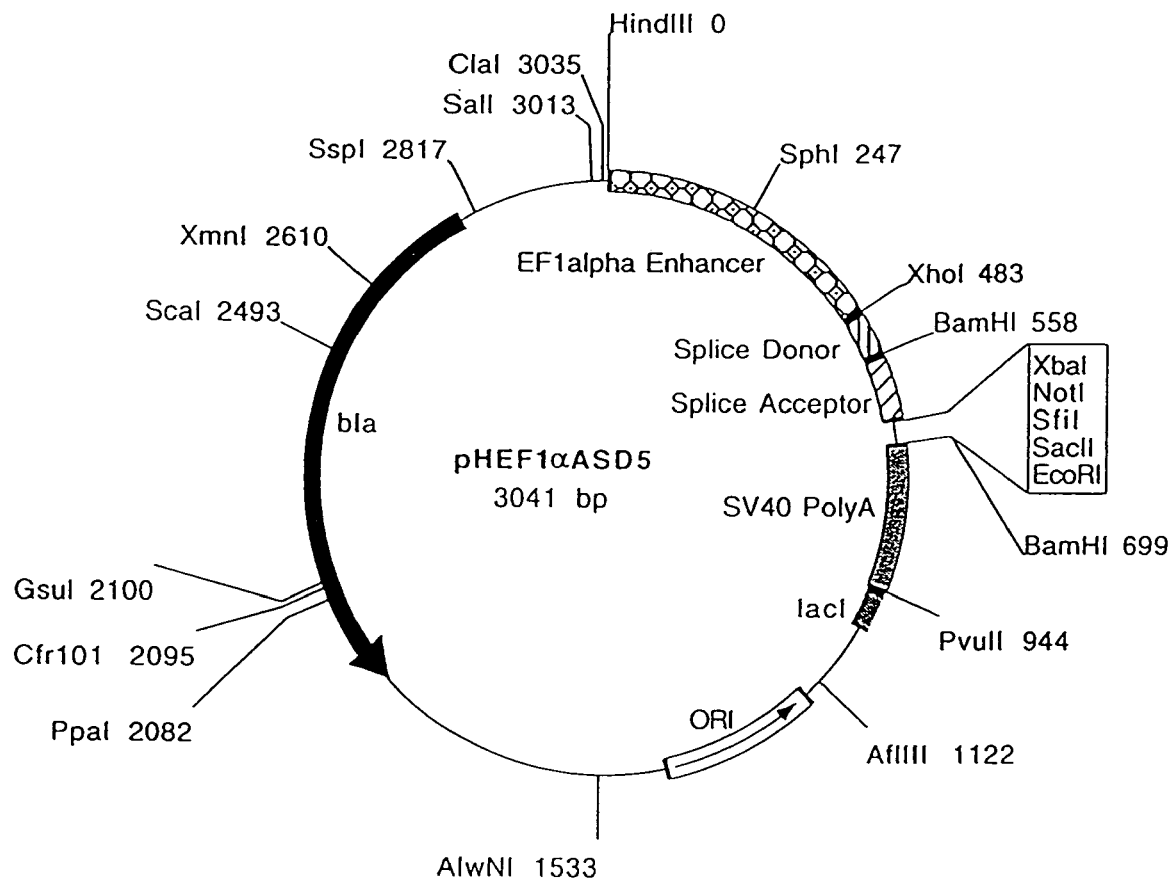
FIG. 7 shows the map of the expression vector pHEF1αASD5. Selected restriction enzyme sites are indicated.
Figure 8:
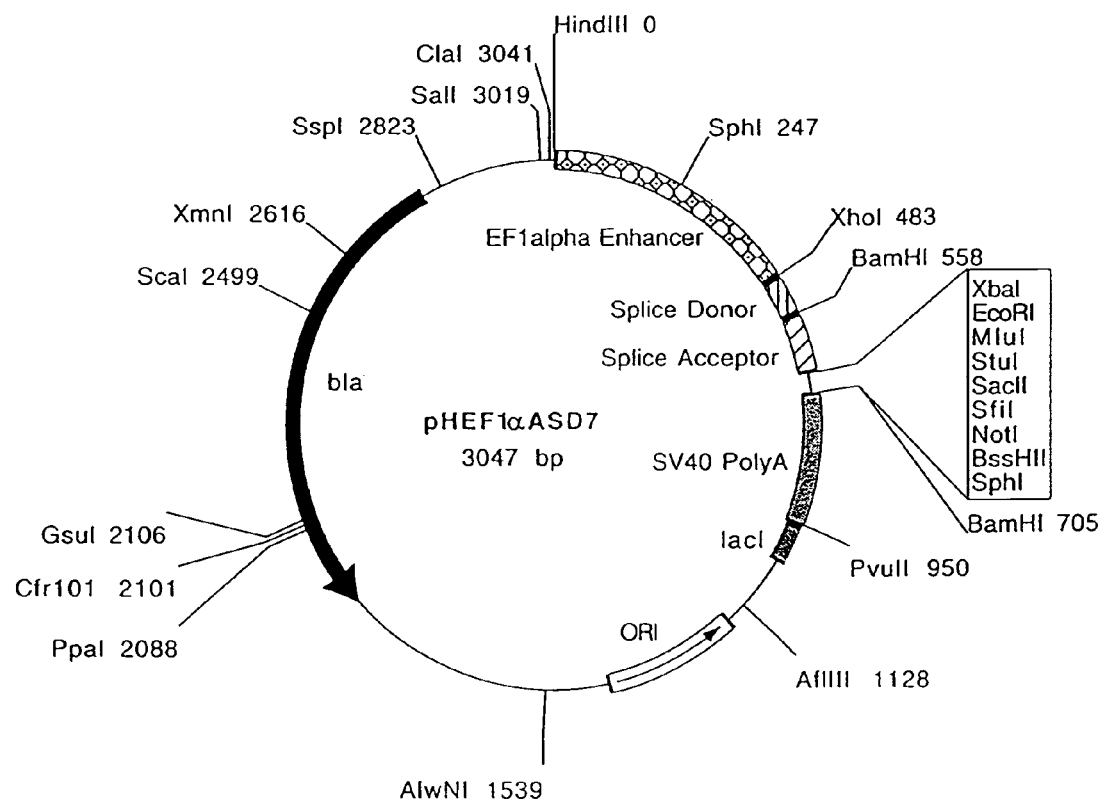
FIG. 8 shows the map of the expression vector pHEF1αASD7. Selected restriction enzyme sites are indicated.

The 5' primer, designated HEF1αL5, contains the following sequence: 5'-AAGCTTTGGAGCTAAGCCAGCAAT-3' (SEQ ID NO:9). The 3' primer, designated HEF1αL3A, contains the following sequence: 5'-CTCGAGGCGGCAA ACCCGTTGCG-3' (SEQ ID NO:10). PCR conditions were as reported in Saiki et al., Science 239:487 (1988). Briefly, 10 μg MOU genomic DNA and 1 μM final concentration of each primer were used in a 400 µl PCR reaction. Reaction conditions were 94° C. for 1 minute, 60° C. for 1 minute, 72° C. for 1.5 minutes, 30 cycles. Taq DNA polymerase was obtained from Perkin-Elmer. The primer pair generates a 475 bp fragment having a HindIII site at the 5' end and a XhoI site at the 3' end. The PCR reaction products were electrophoresed on a low melting agarose gel and the 475 bp fragment was recovered as described above. The recovered fragment was digested with HindIII and XhoI and inserted into either pSSD5 or pSSD7 digested with HindIII and XhoI to yield pHEF1αASD5 and pHEF1αASD7, respectively. The maps of pHEF1αASD5 and pHEF1αASD7 are shown in FIGS. 7 and 8, respectively.

Figure 9:
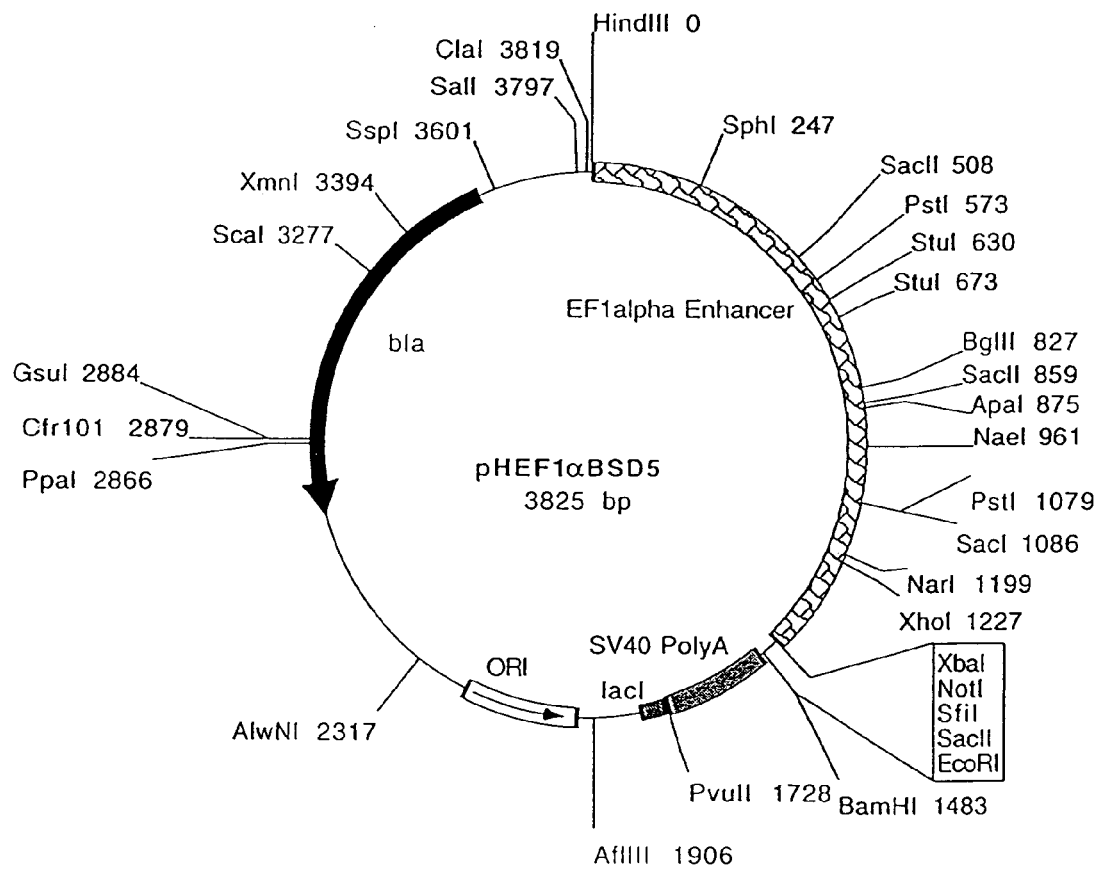
FIG. 9 shows the map of the expression vector pHEF1αBSD5. Selected restriction enzyme sites are indicated.
Figure 10:
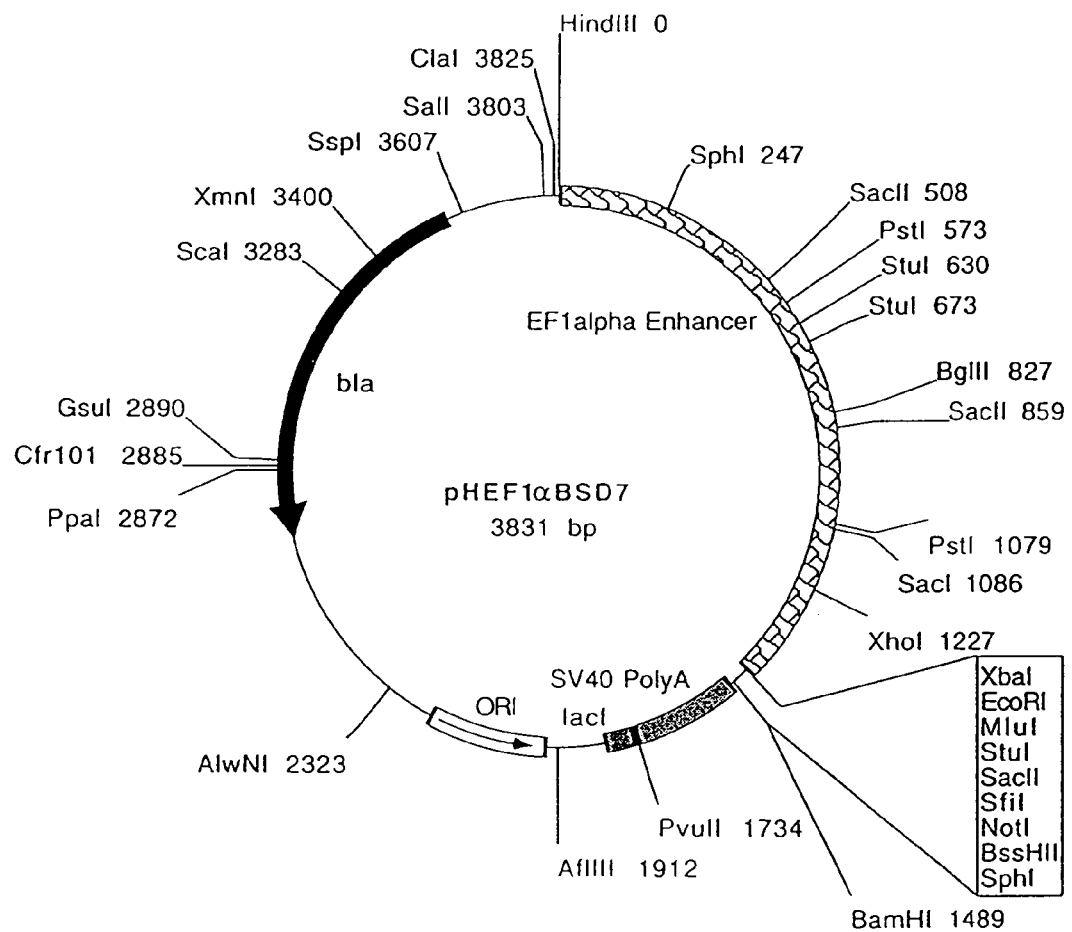
FIG. 10 shows the map of the expression vector pHEF1αBSD7. Selected restriction enzyme sites are indicated.

B. Construction of pHEF1αBSD5 and pHEF1αBSD7 pHEF1αBSD5 and pHEF1αBSD7 were constructed as described above for pHEF1αASD5 and pHEF1αASD7 with the exception that the HEF1αL3B primer was used instead of the HEF1αL3A primer with the HEF1αL5 primer to generate a ~1.45 kb fragment containing the human elongation factor 1α enhancer/promoter and a splice donor and acceptor from the human elongation factor 1α gene. The ~1.45 kb fragment corresponds to map units 125 to 1567 in the human elongation factor 1α gene (SEQ ID NO:11). The sequence of HEF1αL3B is 5'-TCTAGAGTTTTCACG ACACCTGA-3' (SEQ ID NO:12). The HEF1αL3B primer generates a XbaI site at the 3' end of the ~1.45 kb fragment. This fragment was digested with HindIII and XbaI and inserted into either pSSD5 or pSSD7 digested with HindIII and XbaI to generate pHEF1αBSD5 or pHEF1αBSD7, respectively. Digestion of pSSD5 and pSSD7 with HindIII and XbaI removes the SV40 enhancer/promoter and the SV40 16S splice junction. These SV40 sequences are replaced with the human elongation factor 1α enhancer/promoter and a splice donor and acceptor from the human elongation factor 1α gene. The maps of pHEF1αBSD5 and pHEF1αBSD7 are shown in FIGS. 9 and 10, respectively.

EXAMPLE 2

Construction of the Selection Vector pMSD5-HPRT pMSD5-HPRT contains a full length cDNA clone encoding the mouse HPRT enzyme under the transcriptional control of the Moloney LTR. The Moloney LTR contains a strong enhancer/promoter which is active in a broad range of cell types [Laimins et al., Proc. Natl. Acad. Sci. USA 79:6453 (1984)]. The pMSD5-HPRT expression vector is used as the selective plasmid (or selective or selectable marker) when HPRT⁻ cell lines, such as BW5147.G.1.A, are used as the recipient cell line for the generation of stable transformants. HPRT⁻ cell lines cannot grow in medium containing hypoxanthine, aminopterin or azaserine and thymidine (HAT medium). The addition of a functional HPRT gene by gene transfer allows the cells which have integrated the vector DNA encoding the HPRT gene to grow in HAT medium.

a. Isolation of a Full Length Mouse HPRT cDNA

Figure 11:
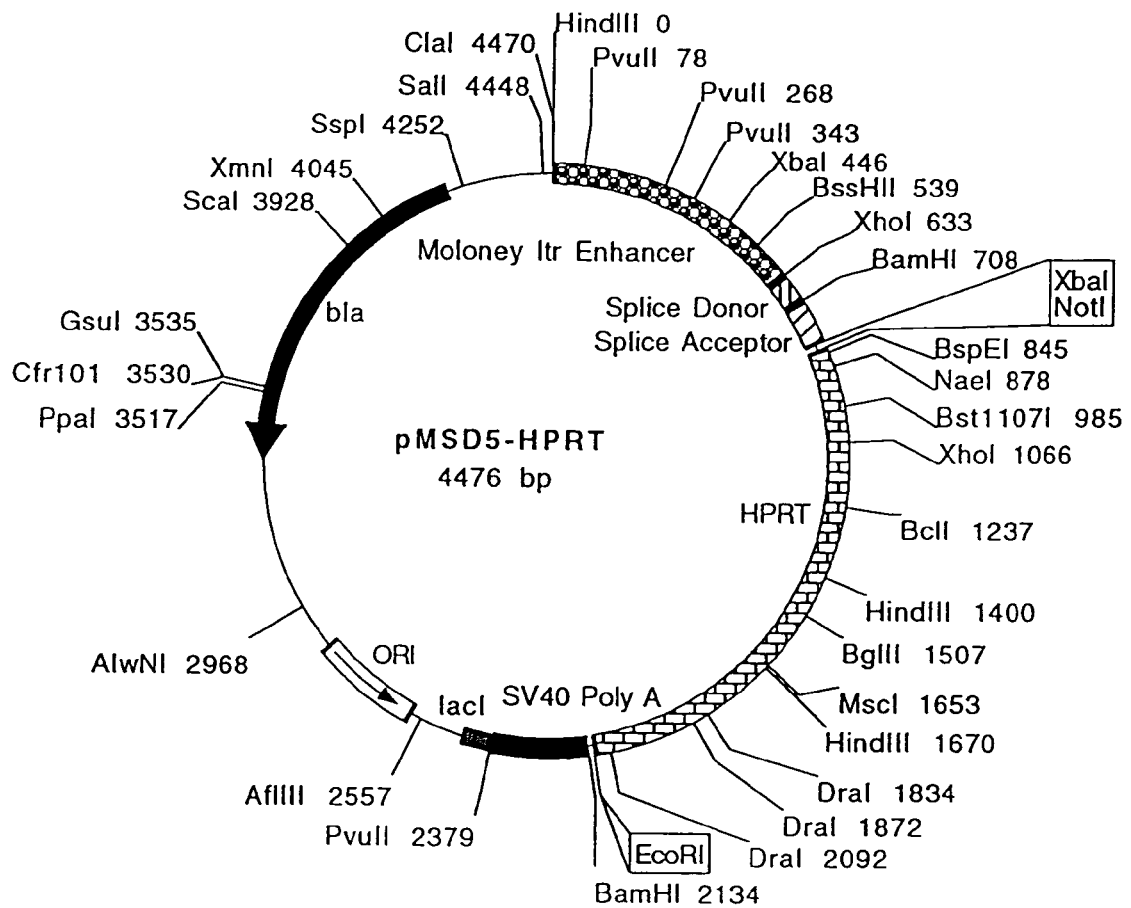
FIG. 11 shows the map of the expression vector pMSD5-HPRT. Selected restriction enzyme sites are indicated.

A cDNA library was prepared from poly A⁺ mRNA isolated from C6VL cells [Allison et al., J. Immunol., 129:2293 (1982)] using standard techniques [Sambrook et al., supra at 7.26-7.29]. cDNA was generated from the mRNA and inserted into the expression vector λgt10 using standard techniques [Huynh, et al., in *DNA Cloning: A Practical Approach* (D. M. Glover, ed.), Vol. 1, IRL Press Oxford (1985), pp. 49-78]. The full-length mouse HPRT cDNA was isolated using a full-length human HPRT cDNA clone containing an approximately 1.4 kb PstI-BamHI restriction fragment as a probe [pcD-HPRT; Jolly et al. (1983) Proc. Natl. Acad. Sci. USA 80:477]. The full length cDNA clone was digested with NotI and EcoRI to generate a 1.3 kb fragment containing the coding region of HPRT (the coding region of the mouse HPRT is listed in SEQ ID NO:13; the amino acid sequence encoded within SEQ ID NO:13 is listed in SEQ ID NO:14).

pMSD5 (described in Example 1) was digested with NotI and EcoRI and the 1.3 kb NotI/EcoRI fragment containing the mouse HPRT cDNA was inserted to generate pMSD5-HPRT. The map of pMSD5-HPRT is shown in FIG. 11.

EXAMPLE 3

Construction of the Amplification Vector pSSD7-DHFR pSSD7-DHFR contains a full length copy of the mouse DHFR cDNA under the transcriptional control of the SV40 enhancer/promoter. This promoter/enhancer is active in a wide variety of cell types from many mammalian species [Dijkema et al., EMBO J., 4:761 (1985)]. pSSD7-DHFR is referred to as the amplifiable marker as the use of this vector allows the selection of cell lines which have amplified the vector sequences by selecting for cell which can grow in increasing concentrations of MTX.

The mouse DHFR cDNA was isolated from double stranded cDNA generated from liver RNA using the PCR as follows. Poly A⁺ RNA was isolated from the liver of (Balb/cxC57B1/6) F1 mice using standard techniques. First strand cDNA was synthesized from the poly A⁺ RNA in a final reaction volume of 100 µl. The following reagents were added in order: 35.6 µl H$_2$O, 5 µl poly A⁺ RNA (1 µg) and 1.4 µl SBNSSdT primer (1 µg). The sequence of the SBNSSdT primer is 5'-GCAT GCGCGCGGCCGCGGAG-GCTTTTTTTTTTTTTTTTTT-3' (SEQ ID NO:15). The water, primer and RNA were heated at 60° C. for 2 minutes then placed on ice. Forty µl of all four dNTPs at 5 mM each, 10 µl 10× reverse transcriptase salts (1.0 M Tris-HCl, pH 8.3, 0.5 M KCl, 0.1 M MgCl$_2$, 0.1 M DTT), 2 µl RNasin (Promega) and 5 µl AMV reverse transcriptase (Molecular Genetic Resources, Tampa, Fla.). The reaction was run at 41° C. for 3 hours. The reaction was stopped by incubation at 65° C. for 10 minutes.

The reaction components were transferred to a Centricon 100 tube (Amicon) and 2.1 ml of 5 mM Tris-HCl, pH 8.3 was added. The tube was centrifuged at 300 rpm (~700 g) for 4 minutes at 10° C. 2.2 ml of Tris-HCl, pH 8.3 was added and the tube was centrifuged again as above. This washing step was repeated and then the tube was inverted and centrifuged at 2500 rpm for 5 minutes at 10° C. to recover the first strand cDNA (volume ~50 µl). Second strand cDNA was synthesized as follows. 96 µl H$_2$O and 20 µl 10× rTth RTase buffer (900 mM KCl, 100 mM Tris-HCl, pH 8.3) was added to the first strand cDNA. In a separate tube the following components were mixed: 20 µl 10 mM MnCl$_2$, 4 µl of each of the four dNTPs at 10 mM and 10 µl rTth reverse transcriptase (Perkin-Elmer). Both mixtures were heated to 60° C. and the second mixture was added to the cDNA mixture. The reaction was carried out at 60° C. for 10 minutes. The reaction was stopped by addition of 25 µl chelating buffer [50% glycerol (v/v), 1 mM KCl, 100 mM Tris-HCl, pH 8.3, 7.5 mM EGTA, 0.5% Tween 20] and the mixture was placed on ice.

The reaction mixture was then transferred to a Centricon 100 tube and 2.1 ml of 5 mM Tris-HCl, pH 7.5 was added. The tube was centrifuged at 5500 rpm for 30 minutes at 10° C. 2.2 ml of Tris-HCl, pH 7.5 was added and the tube was centrifuged again as above. This washing step was repeated and then the tube was inverted and centrifuged at 2500 rpm for 5 minutes at 10° C. to recover the double stranded cDNA (volume ~50 µl). The cDNA was precipitated with ethanol, resuspended in sterile H$_2$O and quantitated by absorption at 260 and 280 nm.

Two hundred pg of double stranded cDNA was used in a 400 µl PCR reaction. The primer set used to prime the PCR was: muDHFR.A: 5'-CGGCAAC GCGTGCCATCATGGT-TCGAC-3' (SEQ ID NO:16) and muDHFR.B: 5'-CGGCA GCGGCCGCATAGATCTAAAGCCAGC-3' (SEQ ID NO:17). The PCR reaction conditions were as reported in Saiki et al., Science 239:487 (1988). Briefly, the reaction was run at 94° C. for 1 minute, 55° C. for 1 minute, 72° C. for 1.5 minutes and 30 cycles were performed. Taq DNA polymerase was obtained from Perkin-Elmer and the reaction buffer used was that recommended by the manufacturer. The primer pair generates a 671 bp fragment having a MluI site at the 5' end and a NotI site at the 3' end (SEQ ID NO:18; the amino acid sequence encoded by SEQ ID NO:18 is listed in SEQ ID NO:19). The PCR reaction products were digested with MluI and NotI and electrophoresed on a low melting temperature agarose gel (SeaPlaque, FMC). The 671 bp fragment was cut out of the gel and the agarose was removed by digestion with β-Agarase I (NEB) followed by isopropanol precipitation according to the manufacturer's directions.

Figure 12:
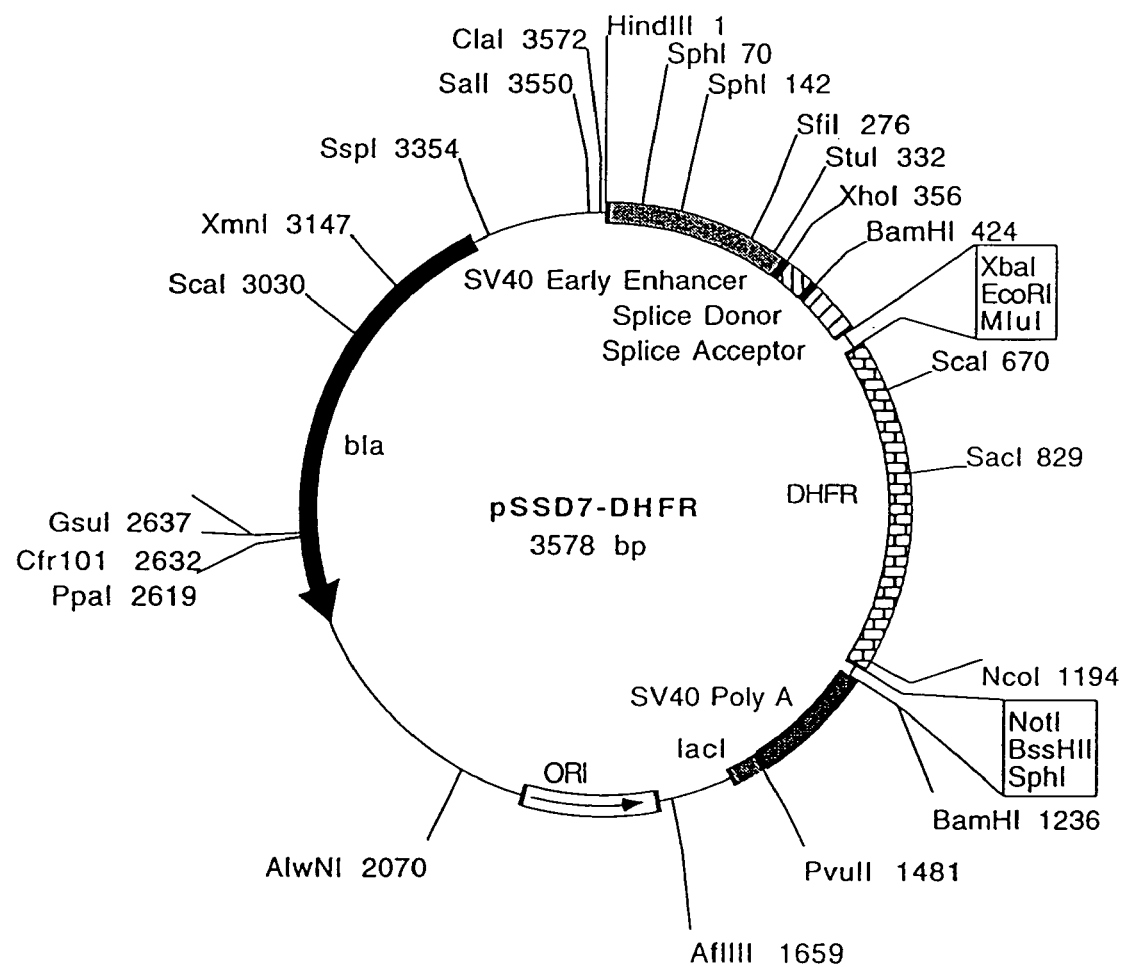
FIG. 12 shows the map of the expression vector pSSD7-DHFR. Selected restriction enzyme sites are indicated.

The 671 bp fragment was inserted into pSSD7 which digested with MluI and NotI to generate pSSD7-DHFR. The map of pSSD7-DHFR is shown in FIG. 12.

EXAMPLE 4

Construction of the Expression Vector pJFE 14ΔIL10 pJFE 14ΔIL10 contains a full length cDNA clone encoding the mouse interleukin 10 (IL-10) protein under the transcriptional control of the SRα enhancer/promoter. As discussed above, the SRα enhancer/promoter is active in a broad range of cell types. pJFE 14ΔIL10 is used to direct the expression of the IL-10 gene in transfected cells (i.e., pJFE 14ΔIL10 expresses IL-10 as the gene of interest).

a. Construction of pJFE 14ΔIL10

Figure 13:
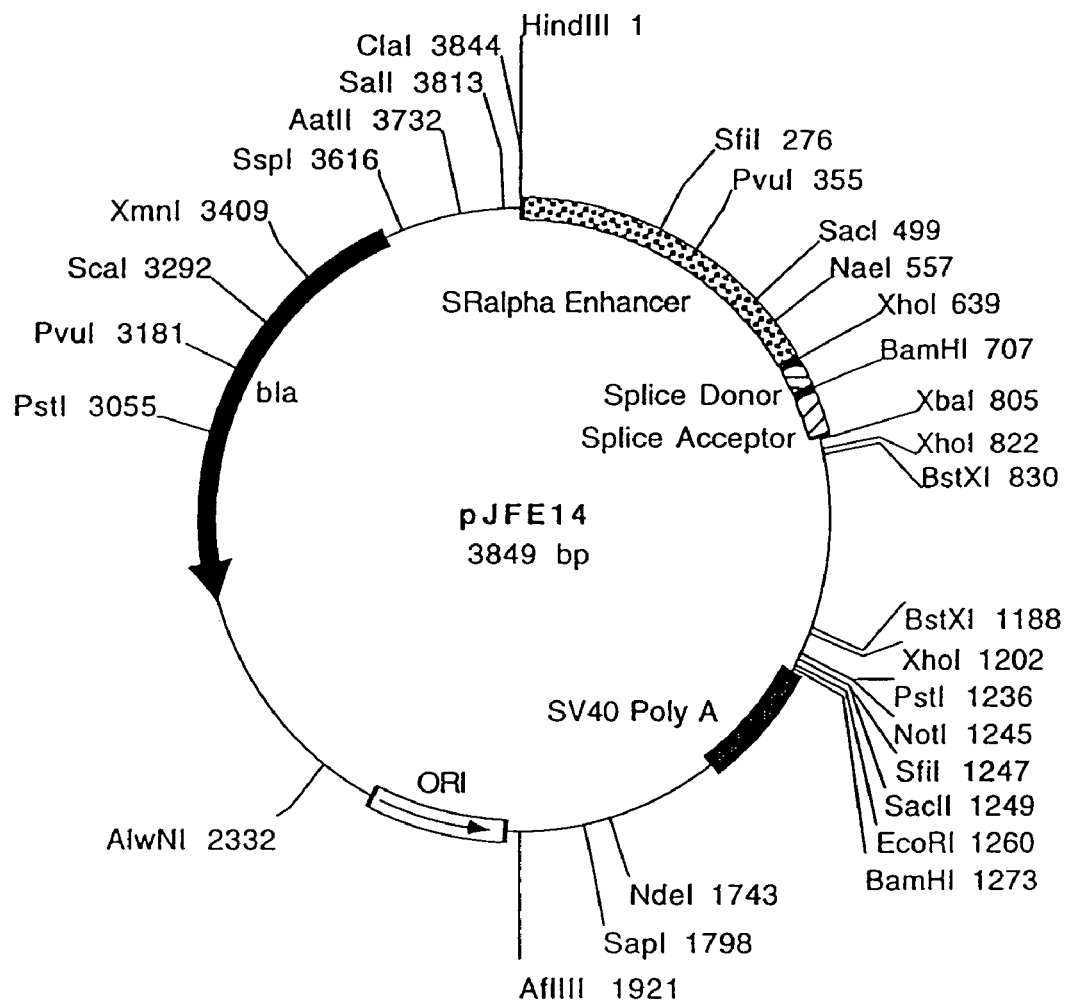
FIG. 13 shows the map of the expression vector pJFE 14. Selected restriction enzyme sites are indicated.

The plasmid pJFE14 [Elliott et al. (1990) Proc. Natl. Acad. Sci USA 87:6363] was constructed by combining DNA fragments from the plasmids pSSD, pcDL-SRα296 [Takebe et al. (1988) Mol. Cell. Biol. 8:466] and pCDM8 [Seed (1987) Nature 329:840]. pSSD was cut with HindIII and XhoI and a 2.77 kb fragment was isolated from an agarose gel. pcD-SRα296 was cut with HindIII and XhoI and an ~640 bp fragment was isolated from an agarose gel. The two gel-purified DNA fragments were ligated together to generate the plasmid pSRαSD. pSRαSD was cut with XbaI and NotI and a 3.4 kb fragment was isolated from an agarose gel. pCMD8 was cut with XbaI and NotI and a 440 bp fragment was isolated. The 3.4 kb and 440 bp XbaI/NotI fragments were ligated together to generate pJEL14. A schematic of pJFE14 is shown in FIG. 13.

Figure 14:
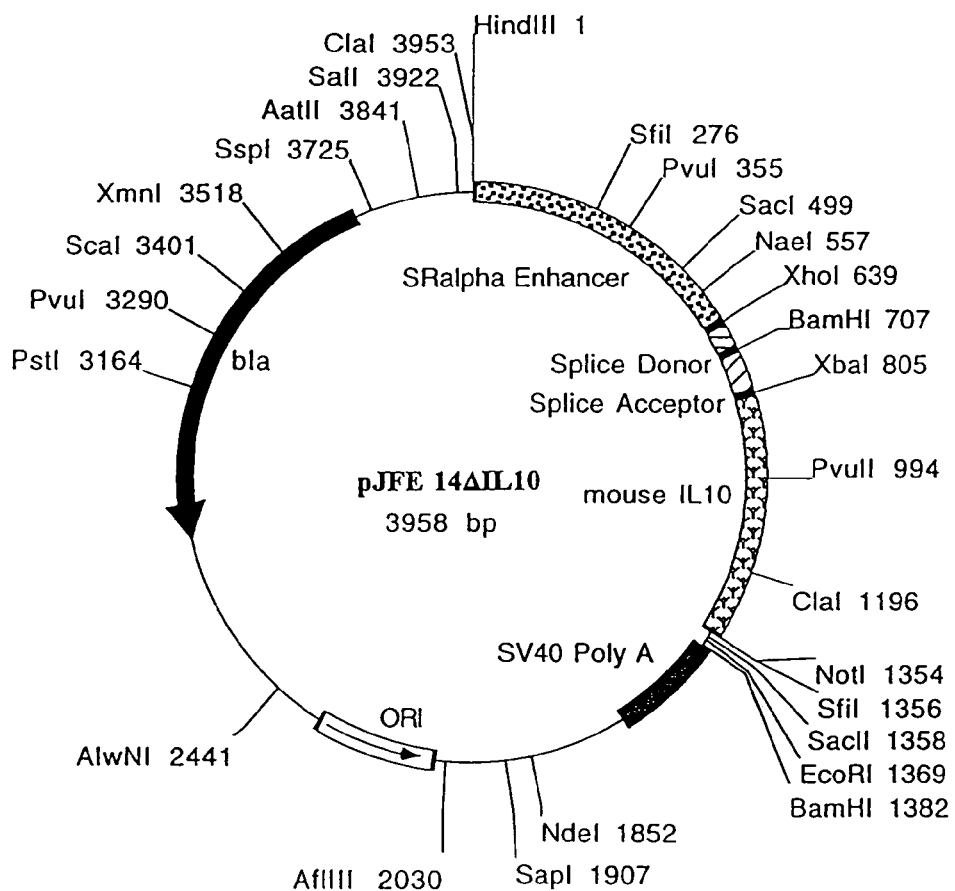
FIG. 14 shows the map of the expression vector pJFE 14ΔIL10. Selected restriction enzyme sites are indicated.

The ΔIL10 cDNA was generated from a full-length mouse cDNA clone, F115 [Moore et al. (1990) Science 248:1230] using the PCR. The pcDSRα-F115 clone was linearized with BamHI, which cuts out the cDNA insert. A PCR reaction was run using AmpliTaq™ DNA Polymerase (Perkin Elmer) and buffer supplied by the manufacturer according to their suggested conditions. The primers used in the PCR were IL10Δ-5' [5'-ATATATCTAGACCACCATGCCTGGCT-CAGCACTG-3' (SEQ ID NO:20)] and IL10Δ-3' [5'-ATTATTGCGGCCGCTTAGCTTTTCATTTTGAT CAT-3' (SEQ ID NO:21)]. The PCR reaction was run at 94° C., 1 min, 72° C., 1 min, 46° C., 1 min for 30 cycles. The PCR generated DNA has deleted essentially all of the non-coding sequences and placed an optimal Kozak sequence just 5' to the initiator ATG of the IL-10 gene sequences. The PCR generated DNA was extracted with phenol:CHCl$_3$ (1:1) and then with CHCl$_3$. The DNA was ethanol precipitated, pelleted in a microcentrifuge and resuspended in TE. The DNA was cut with XbaI and NotI. pJFE14 was cut with XbaI and NotI. Both digestion mixtures were run on a low melt agarose gel. The 550 bp ΔIL10 band and the 3.4 kb pJFE14 band were cut out of the gel and combined in a tube. The DNAs were co-extracted from the agarose, ligated together and transformed into the bacteria DH5α. Colonies were picked and the clone pJFE14-ΔIL10 was identified. A schematic map of pJFE14-ΔIL10 is shown in FIG. 14.

EXAMPLE 5

Construction of pSRαSD5-DRα-DAF pSRαSD5-DRα-DAF contains a cDNA clone encoding a chimeric mouse DRα gene. In this chimeric protein, the extracellular domain of the DRα protein is joined to sequences derived from the decay accelerating factor (DAF) gene. The DAF sequences provide a glycophosphatidylinositol linkage which allows the chimeric protein to be cleaved from the surface of the cell (cell surface expression requires the expression of the DRβ chain in the same cell) by treatment of the cell with phospholipase C.

a. Construction of the Phagemid Vector pDAF20

To generate pSRαSD5-DRα-DAF and pSRαSD5-DRβ1-DAF (Example 6), a vector containing sequences encoding a portion of decay accelerating factor (DAF) which anchors DAF to the cell surface via a glycophosphatidylinositol linkage was constructed. pDAF20 was constructed as follows.

Two micrograms of pBluescript KS(−) (Stratagene) was cut with EcoRV (NEB). TE buffer was added to such that the final volume was 200 µl. Spermine was added to a final concentration of 1.4 mM and the DNA was allowed to precipitate for 20 minutes on ice. The precipitated DNA was then pelleted by centrifugation for 10 min. in a microcentrifuge and the spermine was washed from the pellet exactly as described [Hoopes and McClure (1988) Nucleic Acids Res. 9:5493]. Briefly, the pellet was dispersed in extraction buffer [75% EtOH, 1× Buffer 2 (0.3M sodium acetate, 0.01M magnesium acetate)] by vortexing; the dispersed pellet was then left on ice for 1 hour. The pellet was collected by centrifugation for 10 min. in a microcentrifuge. The pellet was dried at room temperature and resuspended in 14 µl H$_2$O. On ice, 250 ng each of DAFa (SEQ ID NO:22) and DAFb (SEQ ID NO:23) unphosphorylated oligonucleotides were added to the resuspended DNA. The DNA-oligonucleotide mixture was then brought to a final concentration of 50 mM Tris-HCl (pH 7.5), 10 mM MgCl$_2$, 10 mM DTT and 1 mM rATP in a final reaction volume of 20 µl. Eighty units of T4 DNA ligase (NEB) was added and the ligation mixture was placed at 14° C. overnight. The ligation mixture was then heated to 65° C. for 10 min. NaCl was added to a final concentration of 50 mM and the DNA was digested with EcoRV (NEB). An aliquot of the DNA was then used to transform competent HB101.

Clones were picked and miniprep DNA was examined by restriction enzyme digestion. A clone, called DAF20, was isolated that has the DAF sequence cloned in the EcoRV site of pBluescript KS(−) with the XbaI at one end of the DAF sequence adjacent to the EcoRI site in the polylinker and away from the HindIII site in the polylinker. The sequence of the pDAF20 polylinker region containing the DAF insert is listed in SEQ ID NO:24.

The resulting plasmid pDAF20 contains DNA encoding the final 37 amino acids of the form of DAF that is anchored to the cell surface by a glycophosphatidylinositol (PI) linkage [Caras et al. (1987) Nature 325:545]. Chimeric proteins containing these 37 amino acids at their C-terminus, can be expressed on the cell surface of mammalian (and insect) cells with this PI anchor. This anchor can be readily cleaved and the protein solubilized from the cell surface using phosphatidylinositol-specific phospholipase C [Caras et al. (1987) Science 238:1280].

Phosphatidylinositol-specific phospholipase C was purified from *Bacillus thuringiensis* (ATCC 10792) exactly as described [Kupke et al. (1989) Eur. J. Biochem. 185:151]; phosphatidylinositol-specific phospholipase C is available commercially (e.g., Sigma).

The use of soluble class II molecules complexed with specific peptides has been suggested for the treatment of autoimmune disease [Sharma, et al. (1991) Proc. Natl. Acad. Sci. USA 88:11465]. Such therapy requires that ample quantities of soluble class II molecules be available. The present invention allows large quantities of soluble class II molecules to be produced from cells expressing class II molecules on the cell surface wherein these molecules are anchored to the cell via the PI anchor provided by sequences derived from DAF. Alternatively, soluble forms of cell surface proteins can be produced according to the methods of the present invention using DNA sequences encoding chimeric class II molecules containing a thrombin cleavage site between the extracellular domain and the transmembrane domain of each chain comprising the class II heterodimer.

b. Isolation of a Full-Length HLA DRα cDNA

A cDNA library was prepared from poly A+ mRNA isolated from IBw4 cells (GM03104B, NIGMS Human Genetic Mutant Cell Repository at the Coriell Institute for Medical Research, Camden, N.J.) using standard techniques [Sambrook et al., supra at 7.26-7.29]. cDNA was generated from the mRNA and inserted into the cloning vector λgt10 using standard techniques [Huynh et al., in *DNA Cloning: A Practical Approach* (D. M. Glover, ed.), vol. 1, IRL Press Oxford (1985), pp. 49-78]. A full-length DRα cDNA was isolated from the library using a partial DRα cDNA as a probe; the partial DRα cDNA was contained within pDRα1 [Stetler et al. (1982) Proc. Natl. Acad. Sci. USA 79:5966]. The resulting full-length DRα cDNA was contained on a 1.2 kb NotI/EcoRI fragment.

C. Construction of SRαSD5-DRα-DAF

An in-frame connection between the extracellular coding sequence of DRα and the DAF sequence was performed using site-directed in vitro deletional mutagenesis [Kunkel et al. (1987) Methods in Enzymology 154:367]. The mutational, bridging oligonucleotide encodes the desired connection.

The full length DRα cDNA was subcloned as a NotI-EcoRI fragment into pDAF20 (section a above). The pDAF20-DRα was isolated and transformed into the bacteria BW313 [Kunkel et al. (1987), supra]. A colony was then grown overnight in LB containing 100 µg/ml ampicillin. The overnight culture was diluted 1:10 in a final volume of 6 ml and grown at 37° C. After 1 hour, 400 µl of a stock of helper phage R408 [Russel et al. (1986) Gene 45:333] having a titer of approximately $1 \times 10^{11}$ pfu/ml was added to the culture and the culture was grown at 37° C. for approximately 8 hours. One point four (1.4) ml aliquots of the culture were then placed into 4 microcentrifuge tubes and spun in a microcentrifuge 5 min at 4° C. One point one (1.1) ml of each supernatant was transferred to fresh microcentrifuge tubes containing 150 µl of 20% PEG(6000), 2.5 M NaCl. The contents of the tubes were mixed and allowed to stand at room temp. for at least 20 min. Precipitated, ssDNA containing phage particles were pelleted in a microcentrifuge for 5 min at 4° C. Care was taken to remove all the PEG-containing supernatant from the pellets. The four pellets were resuspended in a total of 200 µl of 300 mM NaOAc, pH 7 and extracted with an equal volume of phenol:$CHCl_3$ (1:1) twice, and then once with $CHCl_3$. Two volumes of ethanol was added to the supernatant and chilled to −20° C. The ssDNA was pelleted in a microcentrifuge 20 min at 4° C. The pellet was dried and resuspended in 10 µl TE buffer.

The bridging oligonucleotide was phosphorylated in a volume of 20 µl containing 50 mM Tris-HCl (pH 7.4), 10 mM $MgCl_2$, 10 mM DTT, 1 mM rATP and 65 ng of the RADAF2 oligonucleotide (SEQ ID NO:25) with 8 units of T4 DNA polynucleotide kinase (Pharmacia) at 37° C. for 1 hour. To anneal the bridging oligonucleotide to the ssDNA template, 1.1 µl of the phosphorylated RADAF2 oligonucleotide (SEQ ID NO:25) and 5 µl of the ssDNA prep were mixed in a final volume of 15 µl of 40 mM Tris-HCl (pH 7.5), 20 mM $MgCl_2$, 50 mM NaCl, heated to 70° C. and allowed to cool to room temp. on the bench top. In the reaction tube, the concentrations of the buffers were adjusted to give, in a final volume of 95 µl, 16.8 mM Tris-HCl, pH 7.5, 11.6 mM $MgCl_2$, 7.9 mM NaCl, 10.5 mM DTT and 1.1 mM rATP. Four units of T4 DNA ligase (NEB) and 3.8 units of Sequenase (US Biochemicals) were added to the reaction, which was incubated at room temp. for 5 min and 37° C. for 1 hour. The reaction was adjusted to 58 mM NaCl and heated at 65° C. for 10 min. The tube was cooled to 37° C. and the DNA cut with EcoRI and XbaI. An aliquot of DNA was transformed into *E. coli* strain TG2 and plated on ampicillin-containing plates. A clone that showed the proper deletion of DNA between the desired connection of the DRα and DAF sequences was isolated. This clone was sequenced to confirmed the presence of the desired sequences using standard techniques. The coding region for the DRα-DAF protein is listed in SEQ ID NO:26; the amino acid sequence encoded by SEQ ID NO:26 is listed in SEQ ID NO:27.

Figure 15:
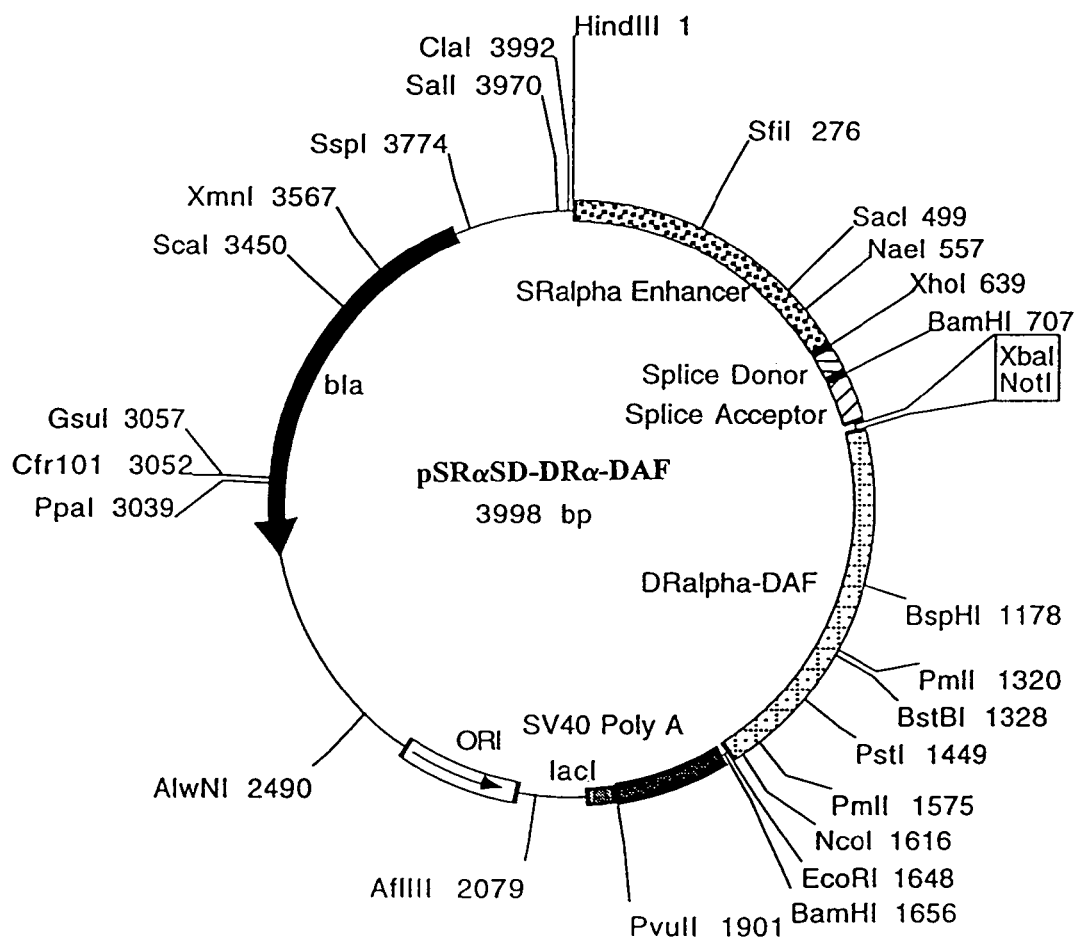
FIG. 15 shows the map of the expression vector pSRαSD-DRα-DAF. Selected restriction enzyme sites are indicated.

The plasmid containing the correct DRα-DAF construct was cut with HindIII. The ends generated by HindIII digestion were made blunt with Klenow enzyme and unphosphorylated EcoRI linkers were ligated onto the blunt ends using standard techniques. The DNA was transformed into competent *E. coli* and clones which contained the DRα-DAF sequences as a NotI-EcoRI fragment were isolated. The DRα-DAF DNA was then subcloned into the pSRαSD5 plasmid as a NotI-EcoRI fragment to generate pSRαSD5-DRα-DAF. The map of pSRαSD5-DRα-DAF is shown in FIG. 15.

EXAMPLE 6

Construction of pSRαSD5-DRβ1-DAF pSRαSD5-DRβ1-DAF contains a cDNA clone encoding a chimeric mouse DRβ1-DAF gene. In this chimeric protein, the extracellular domain of the DRβ1 protein is joined to sequences derived from the DAF gene. The DAF sequences provide a glycophosphatidylinositol linkage which allows the chimeric protein to be cleaved from the surface of the cell (cell surface expression requires the expression of the DRα chain in the same cell) by treatment of the cell with phospholipase C.

a. Isolation of a Full-Length DRβ1 cDNA

A cDNA library was prepared from poly A+ mRNA isolated from IBw4 cells (GM03104B, NIGMS Human Genetic Mutant Cell Repository at the Coriell Institute for Medical Research, Camden, N.J.) using standard techniques [Sambrook et al., supra at pp. 7.26-7.29]. cDNA was generated from mRNA and inserted into the cloning vector λgt10 using standard techniques [Huynh et al., in *DNA Cloning: A Practical Approach* (D. M. Glover, ed.), vol. 1, IRL Press Oxford (1985), pp. 49-78]. A full-length DRβ1 cDNA clone was isolated from the library using a full length DRβ cDNA probe which was contained within the plasmid p2918.4 [Bell et al. (1985) Proc. Natl. Acad. Sci. USA 82:3405]. The resulting full-length DRβ1 clone was contained on a 1.2 kb NotI/EcoRI fragment.

b. Construction of pSRαSD5-DRβ1-DAF

An in-frame connection between the extracellular coding sequence of DRβ and the DAF sequence was performed using site-directed in vitro deletional mutagenesis [Kunkel et al. (1987), supra] as described in Example 5c.

The full length DRβ1 cDNA (section a above) was subcloned into pDAF20 (Ex. 5a) as a NotI-EcoRI fragment to generate pDAF20-DRβ1. pDAF20-DRβ1 DNA was isolated and transformed into the *E. coli* strain BW313. A colony was then grown overnight in LB containing 100 μg/ml ampicillin. The overnight culture was diluted and incubated with helper phage as described in Example 5c to generate single-stranded pDAF20-DRβ1 DNA. The ssDNA was precipitated and resuspended in TE buffer as described in Example 5c.

The bridging oligonucleotide, RQBDAF2 (SEQ ID NO:28), was phosphorylated as described in Example 5c. To anneal the bridging oligonucleotide to the ssDNA template, 1.1 μl of phosphorylated RADAF2 and 5 μl of the ssDNA prep were mixed, heated and cooled as described in Example 5c. The reaction mixture was adjusted to give, in a final volume of 95 μl, a concentration of 16.8 mM Tris-HCl (pH 7.5), 11.6 mM $MgCl_2$, 7.9 mM NaCl, 10.5 mM DTT and 1.1 mM rATP. Four units of T4 DNA ligase (NEB) and 3.8 units of Sequenase (US Biochemicals) were added to the reaction, which was incubated at room temp. for 5 min and 37° C. for 1 hour. The reaction was adjusted to 58 mM NaCl and heated at 65° C. for 10 min. The tube was cooled to 37° C. and the DNA digested with EcoRI and XbaI. An aliquot of the digested DNA was used to transform *E. coli* strain TG2. The transformed cells were plated on plates containing ampicillin. A clone that showed the proper deletion of DNA between the desired connection of the DRβ1 and DAF sequences was isolated. The presence of the desired sequences was confirmed by DNA sequencing using standard techniques. The coding region for the DRβ1-DAF protein is listed in SEQ ID NO:29; the amino acid sequence encoded by SEQ ID NO:29 is listed in SEQ ID NO:30.

Figure 16:
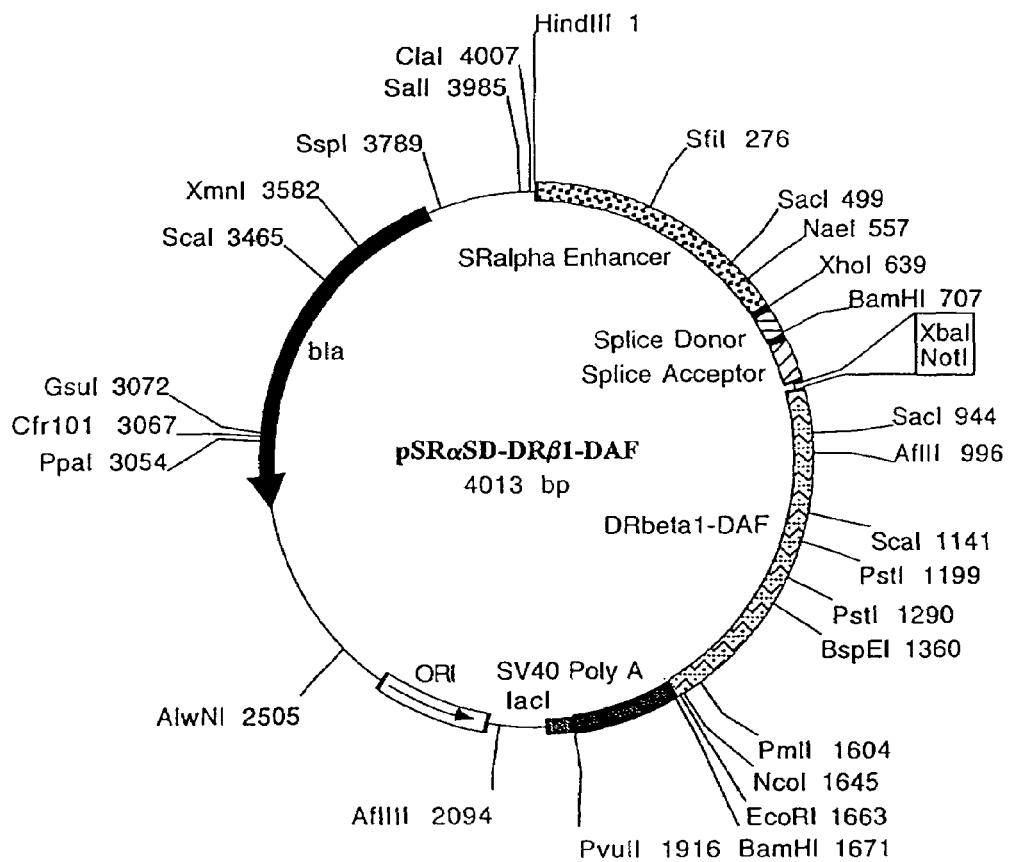
FIG. 16 shows the map of the expression vector pSRαSD-DRβ1-DAF. Selected restriction enzyme sites are indicated.

The plasmid containing the correct DRβ1-DAF construct was cut with HindIII. The DNA was blunted with Klenow enzyme and EcoRI linkers were added to the blunted ends using standard techniques. The DNA was transformed into bacteria that contained the DRγ1-DAF as a NotI-EcoRI fragment were isolated. The DRβ1-DAF DNA was subcloned into pSRαSD5 as a NotI-EcoRI fragment to generate pSRαSD5-DRβ1-DAF. The map of pSRαSD5-DRβ1-DAF is shown in FIG. 16.

EXAMPLE 7

High-Level Expression of Recombinant IL-10 in Lymphoid Cells

High levels of IL-10 were expressed in BW5147.G.1.4 cells (a T lymphoid cell line) by co-amplification of the following three plasmids: 1) the expression vector pJFE 14ΔIL10 which encodes mouse IL10; 2) the selection vector pMSD5-HPRT which encodes the HPRT enzyme and 3) the amplification vector pSSD7-DHFR which encodes the mouse DHFR enzyme. The plasmids were introduced into BW5147.G.1.4 cells by electroporation. The plasmid DNA was isolated from bacterial cells using CsCl density gradient centrifugation.

The plasmids were prepared for electroporation as follows. First, the plasmids were linearized in the same reaction tube. 200 μg of pJFE 14ΔIL10 was digested with SalI. Ten μg of pMSD5-HPRT was digested with SalI. Twenty μg of pSSD7-DHFR was digested with SalI. SalI was obtained from New England BioLabs and restriction digests were performed according to the manufacturer's instructions. The linearized plasmids were then precipitated with ethanol and resuspended in 0.5 ml of 1×HBS(EP) buffer [20 mM HEPES (pH 7.0); 0.75 mM $Na_2HPO_4/NaH_2PO_4$ (pH 7.0); 137 mM NaCl; 5 mM KCl and 1 gm/l dextrose].

BW5147.G.1.4 cells were grown in RPMI 1640 medium (Gibco/BRL) containing 10% FCS (HyClone) and 50 μg/ml gentamycin (Sigma). Prior to electroporation, the cells were washed twice in ice cold 1×HBS(EP) buffer and resuspended at $2 \times 10^7$ cells/ml in 0.5 ml of 1×HBS(EP). The cells were then placed in a 1 ml cuvette (Sarstedt) which contained the linearized DNAs in 0.5 ml of 1×HBS(EP). The cuvette was placed on ice. The electroporation was performed at 225 volts using an ISCO Model 493 power supply. The electroporation apparatus was constructed exactly as described [Chu, G. et al., (1987) Nucl. Acids Res. 15:1311]. The electroporation device was set on constant voltage (225V) at the 2× setting (i.e., both capacitors were used). Following electroporation, the cells were allowed to recover by incubation on ice for 5 to 15 minutes.

The electroporated cells were then transferred to a T75 flask (Falcon) containing 30 ml of RPMI 1640 medium containing 10% FCS and 50 μg/ml gentamycin. The cells were placed in a humidified atmosphere containing 5% $CO_2$ at 37° C. for 36 hours. The cells were then plated in 24 well plates (Falcon, Lincoln Park, N.J.) at a density of $1 \times 10^4$ cells/well in selective medium [RPMI 1640 containing 10% FCS, 100 μM hypoxanthine (Sigma) and 2 μg/ml azaserine (Sigma)]. Each well contained 0.5 ml of selective medium. One week after plating the cells in the 24 well plates, 0.5 ml of fresh selective medium was added.

HPRT+ colonies (i.e., wells containing growing cells or positive wells) were visible after approximately 10 days. At day 13 (with the day of electroporation being day zero) 100 μl of culture supernatant was removed and assayed for the presence of mouse IL10 using an ELISA assay performed as described [Mosmann et al. (1990) J. Immunol. 145:2938]. The monoclonal antibody (mcab) SXC1 (PharMingen, San Diego, Calif.) was used as the capture antibody and biotinylated mcab SXC2 [the mcab JESS-2A5 (PharMingen) may be used in place of SXC2] was used as the detection antibody. Briefly, 20 μl of mcab SXC1 at a concentration of 2 μg/ml in PBS was allowed to bind to the wells of flexible vinyl 96 well plates (Falcon) by incubating for 30 min to 3 hours at 37° C. Excess protein binding sites were then blocked by adding 200 μl/well PBS, 10% FCS. After 30 minutes of blocking at 37°

C., the plates were washed with PBS, 0.1% Tween 20 (ICN Biochemicals, Aurora, Ohio). Samples to be tested were added at 50 µl/well and incubated 1 hour at 37° C. Plates were washed with PBS, 0.1% Tween 20 and 20 µl/well of PBS, 0.1% Tween 20, 1 µg/ml biotinylated mcab SXC2 was added. The plates were incubated 30 min. at 37° C. The supernatants were removed and the plates were washed with PBS, 0.1% Tween 20. A 1/5000 dilution of streptavidin-horseradish peroxidase conjugate (Jackson Immunoresearch Laboratories, West Grove, Pa.) in PBS, 0.1% Tween 20, 0.1% BSA was added at 50 µl/well and incubated 30 min. at 37° C. The plates were then exhaustively washed with PBS, 0.1% Tween 20 and 100 µl/well of 44 mM $NaH_2PO_4$, 28 mM Citric Acid, 0.003% $H_2O_2$, 1 mg/ml 2,2' azino-bis(3-ethylbenzothiazoline-6-sulfonic acid) (Sigma) was added. The optical densities (ODs) of the wells were measured after 1 hour using a VMAX microplate reader (Molecular Devices, Menlo Park, Calif.) with a test wavelength of 405 nm and a reference of 490 nm.

The cells from wells containing 1 to 3 apparent clones and which contained greater than or equal to 100 units IL10/ml were cloned by limiting dilution using standard techniques [Cloning by Limiting Dilution, in Current Protocols in Immunology (J. E. Coligan et al., eds.) John Wiley & Sons, New York, section 2.5.10]. For the limit dilution cloning, the cells were plated at 2 cells or 4 cells per well in a 96 well plate (Falcon) in selective medium; one 96 well plate was set up for each cell density (2 or 4 cells/well). In total, 16 independent colonies were cloned by limit dilution.

Eight days after limit dilution cloning was initiated, isolated colonies were picked from each of the limit dilution plates; these colonies were transferred to a 96 well plate; each well contained 5 ml RPMI 1640 containing 10% dialyzed FCS (HyClone) and 100 µM hypoxanthine. The use of dialyzed serum at this point increases the speed and frequency of amplification of the transfectants; hypoxanthine is added to the medium at this point as it is required for the growth of the cells for a few passages until the azaserine level is diluted to a negligible concentration.

Two days later, 100 µl of culture supernatant was tested for the presence of IL-10 using an ELISA as described above. The two best-producing clones from each of the original wells (e.g., the 24 well plate) were chosen for further manipulation. In total 19 clones (termed selectants as these clones have survived growth in selective medium but have not yet been subjected to amplification by growth in the presence of methotrexate) were chosen.

Five days after the transfer of the isolated colonies (cloned by limit dilution) to 96 well plates, the colonies were transferred to 24 well plates and allowed to expand. The expanded colonies were then transferred to 5 ml flasks (Falcon) containing 5 ml of RPMI 1640 medium containing 10% dialyzed FCS. The clones produced between 100 and 200 units/ml of IL-10.

The selected clones were then subjected to amplification by growing the cells in the presence of methotrexate. The 19 clones were each tested for their sensitivity to methotrexate (MTX). Five×$10^4$ cells from each clone was placed into a well in a series of 24 well plates. The clones were grown in the presence of RPMI 1640 medium containing 10% dialyzed FCS and either 3, 10, 30, 60 or 90 nM MTX. Six clones were able to grow in the presence of greater than or equal to 30 nM MTX; these six clones were retained.

The six clones resistant to ≧30 nM MTX were plated in T25 flasks (Falcon) containing 5 ml of RPMI 1640 medium containing 10% dialyzed FCS and either 90, 150 or 210 nM MTX. Three flasks were set up for each clone. The clones were allowed to grow for 15 days at these three concentrations of MTX and then supernatants were taken from each flask and assayed for IL-10 production using an ELISA as above. All clones from flasks containing 90 or 150 nM MTX produced between 800 and 1200 units/ml of IL10. The best producing clone from each of the six original $MTX^r$ clones was selected (one from a 90 nM MTX flask and the rest from 150 nM MTX flasks). These clones were then expanded to 5 mls in medium containing the appropriate concentration of MTX (over a 6 day period). The clones were then transferred into medium containing either 450, 750 or 1050 nM MTX. Sixteen days later supernatants from clones growing in the presence of 1050 nm MTX were assayed for IL-10 production. The clones were found to produce between 12,000 and 76,000 units/ml of IL-10 (one clone produced 12,000 u/ml, one clone produced 15,000 u/ml and eight clones produced between 50,000 and 76,000 u/ml).

The two clones producing the highest levels of IL-10 were chosen; these clones were designated as 9-2 and 11-2. Clones 9-2 and 11-2 were then grown in the presence of 5 µM MTX for 3 weeks, expanded and then frozen. Cultures were frozen as follows. Thirty milliliters of media containing cells at a density of 6 to 10×$10^5$ cells per ml were pelleted in a 50 ml conical tube (Falcon) at 500×g for 5 minutes. The supernatant was poured off and the cells were resuspended in 7.5 ml of Freezing Media (40% FCS, 53% RPMI 1640, 7% DMSO) and placed in 5 freezing vials (Nunc, Naperville, Ill.). The cells were placed in a −70° C. freezer for 24 to 96 hours and then transferred to liquid nitrogen for long term storage.

Aliquots of each clone were thawed after approximately 2 months, re-tested for IL-10 production and grown continuously in the presence of 5 µM MTX. These two clones (9-2 and 11-2) continue to produce between 64,000 to 86,000 units/ml of IL10.

The levels of expression of IL10 were roughly equivalent when the cells were grown at 1 or 5 µM MTX (compare 76,000 at 1 µM to 64-86,000 at 5 µM). The use of concentrations of MTX greater than 5 µM appeared to make the cells grow more slowly so that the total yield of protein was no greater than that obtained by growing the cells in the presence of 1 to 5 µM MTX.

It should be noted that selective pressure to maintain the expression of the HPRT protein (i.e., growth in the presence of medium containing hypoxanthine and azaserine) was not used after the cells were transferred into medium containing MTX with no loss of IL-10 expression. Furthermore, because the level of IL-10 continued to rise with increasing concentrations of MTX, the endogenous DHFR gene is not likely to be amplified in the $MTX^r$ cells. In other words, the increase in MTX-resistance is due to the amplification of the exogenous DHFR gene present on the amplification vector pSSD7-DHFR.

EXAMPLE 8

High-Level Expression of DR Class II MHC in Lymphoid Cells

High levels of DR class II MHC molecules were expressed on the surface of BW5147.G.1.4 cells by co-amplification of the following four plasmids: 1) the expression vector pSRαSD5-DRα-DAF which encodes the alpha chain of the human DR molecule linked to a DAF tail; 2) the expression vector pSRαSD5-DRβ1-DAF which encodes the beta chain of the human DR molecule linked to a DAF tail; 3) the selection vector pMSD5-HPRT which encodes the HPRT enzyme and 3) the amplification vector pSSD7-DHFR which encodes the mouse DHFR enzyme. The plasmids were introduced into BW5147.G.1.4 cells by electroporation. The plasmid DNAs were isolated from bacterial cells using the standard technique of CsCl density gradient centrifugation.

The isolated plasmid DNAs were prepared for electroporation as follows. First the plasmids were linearized in the same reaction tube. All four plasmids were linearized with SalI. The following amounts of plasmid were used: 200 µg of pSRαSD5-DRα-DAF; 200 µg of pSRαSD5-DRβ1-DAF; 10 µg of pMSD5-HPRT and 25 µg of pSSD7-DHFR. The linearized plasmids were then precipitated with ethanol and resuspended in 0.5 ml of 1×HBS(EP) buffer.

BW5147.G.1.4 cells were grown in RPMI-1640 medium containing 10% FCS and 50 µg/ml gentamicin. Prior to electroporation the cells were washed twice in ice cold 1×HBS (EP) buffer and resuspended at a density of $2\times10^7$ cells/ml in 0.5 ml of 1×HBS(EP). The cells were then placed in a 1 ml cuvette (Sarstedt) which contained the linearized DNAs in 0.5 ml of 1×HBS(EP). The cuvette was placed on ice. The electroporation was performed as described above.

After electroporation the cells were allowed to recover by incubation on ice and then they were placed in a T75 flask (Falcon) containing 30 ml of RPMI-1640 medium containing 10% FCS and 50 µg/ml gentamicin. The cells were placed in a humidified atmosphere containing 5% $CO_2$ at 37° C. and grown in bulk culture for 36 hours. The cells were then plated into four 48 well plates (Costar) at a density of $10^4$ cells/well in 0.5 ml selective medium [RPMI 1640 containing 10% FCS, 100 µM hypoxanthine (Sigma) and 2 µg/ml azaserine (Sigma)]. The use of a cell density of $1\times10^4$ ensures that any colonies which arise are derived from a single cell; that is this density provides for limit dilution cloning. Any remaining cells were plated at a density of $1\times10^5$ cells/well in 0.5 ml of selective medium. One week after plating in the 48 well plates an additional 0.5 ml of selective medium was added.

Wells containing clones capable of growth in the selective medium (selectants) were visible after 8 days. Positive colonies (i.e., positive for growth in selective medium) were picked into 12 well plates (Costar) containing 4 ml of RPMI 1640 containing 10% dialyzed FCS (HyClone) and 100 µM hypoxanthine 10-12 days after the application of selective medium. The use of dialyzed serum at this point increases the speed and frequency of amplification of the selectants; hypoxanthine is added to the medium at this point as it is required for the growth of the cells for a few passages until the azaserine level is diluted to a negligible concentration. The cells were allowed to grow for 3-4 days in the 12 well plates.

Colonies which grew in the presence of hypoxanthine and azaserine (selectants) were checked for the ability to express the DR molecule on the surface of the cell by staining cells with the monoclonal antibody L243. L243 binds specifically to the human HLA-DR antigens [Lampson and Levy, J. Immunol., 125:293 (1980)].

The antibody was prepared as follows. Hybridoma L243 was grown and the culture supernatant collected using standard techniques [Harlow and Lane, eds., *Antibodies: A Laboratory Manual*, Cold Spring Harbor Press, New York (1988), pp. 272, 276]. The monoclonal antibodies were purified from the hybridoma supernatants. L243 was purified on a Protein A-SEPHAROSE column (Pharmacia) using the protocol supplied by the manufacturer. The purified monoclonal antibody was then biotinylated using standard techniques [*Antibodies: A Laboratory Manual*, supra at p. 341]. Biotin was obtained from Vector. Biotinylated L243 was used at a dilution of 1:200.

The cells were stained as follows. The contents of the wells on the 12 well plates were gently mixed by pipeting the medium. One to 2 ml of the cell suspension was removed; this sample size contains $1\text{-}3\times10^6$ cells. The cells were pelleted by centrifugation at 1000 rpm for 4 minutes at 4° C. One hundred µl of L243 diluted into staining media (10 mM HEPES, pH 7.0, 5% calf serum, 4 mM sodium azide in Hanks balanced salt solution) was added. The cells were incubated for 20 minutes on ice. The cells were then washed by adding 1 ml of staining media and then the cells were underlaid with 1 ml of calf serum. The cells were pelleted through the serum by centrifugation at 1000 rpm for 4 minutes at 4° C. The supernatant was removed by aspiration. The cells were then suspended in 100 µl of fluorescein isothiocyanate (FITC) conjugated avidin (Vector, used at 1:50 dilution). The cells were incubated for 20 minutes on ice. The cells were then washed as described above.

The supernatant was removed and the cells were suspended in 200 µl of staining media containing 2 µg/ml propidium iodide. Propidium iodide is excluded from living cells but taken up by dead or dying cells. The addition of propidium iodide allows the exclusion of dead cells (propidium iodide-bright cells) from the analysis. The cells were filtered through nylon screen (Nitex nylon monofilament, 48 micron mesh, Fairmont Fabrics, Hercules, Calif.) prior to analysis on a FACScan™ (Becton-Dickinson). An aliquot of parental BW5147.G.1.4 cells (i.e., not transfected) was stained as above to provide a negative control.

Figure 17:
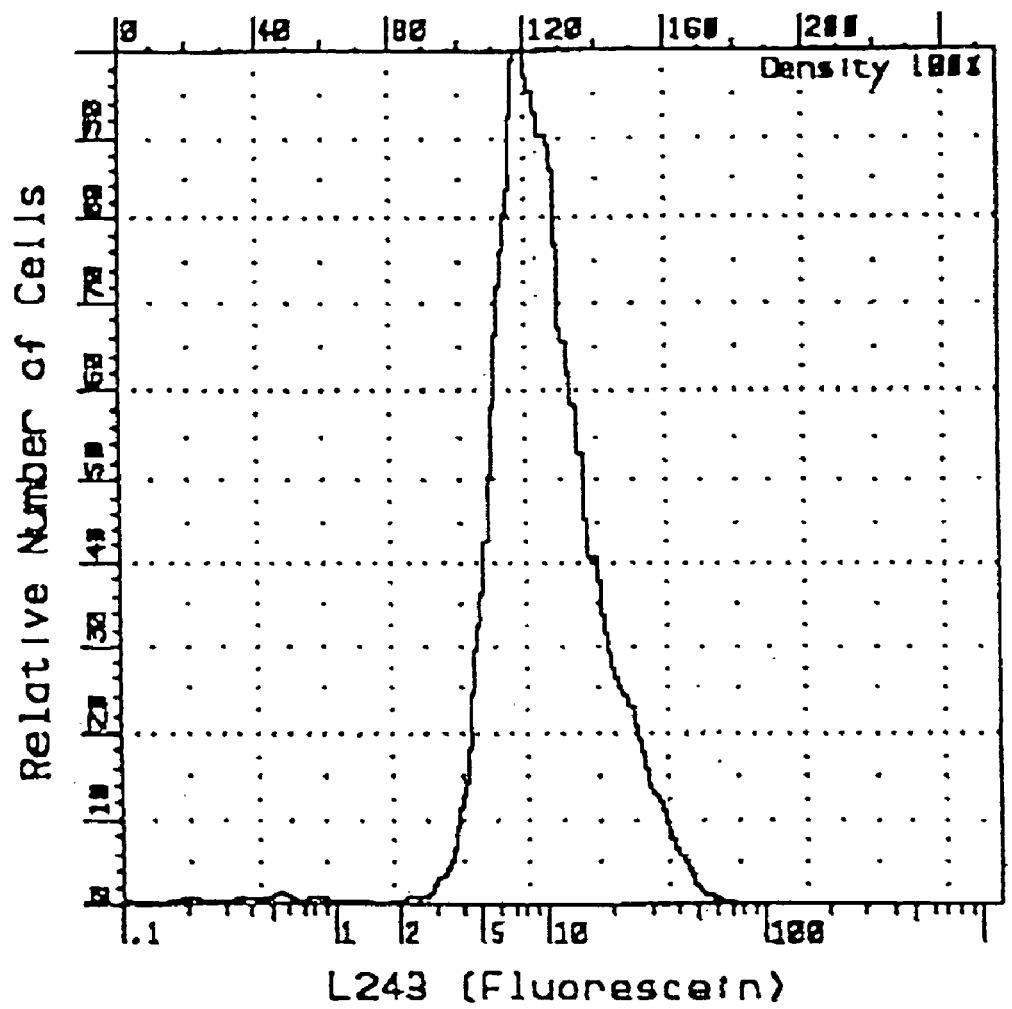
FIG. 17 is a histogram showing the clone 5 cells selected for growth in hypoxanthine and azaserine stained with the L243 monoclonal antibody.

FIG. 17 shows the results of staining a representative selectant clone, clone 5, with L243. FIG. 17 is a histogram showing the log of fluorescein (x axis) plotted against the relative number of cells in the sample. Cells which express the DR molecule on the surface of the BW5147.G.1.4 cell appear as fluorescein bright cells due to staining of the cell surface with biotinylated-L243 followed by FITC-avidin. As shown in FIG. 17, all of the cells in clone 5 express the transfected DR molecule. The fact that surface expression of the DR molecule is seen shows that both the α and the β chain DR constructs are expressed inside clone 5.

Eight selectant clones having the highest levels of expression of DR were chosen for further manipulation. These eight selectant clones were then tested for their sensitivity to MTX. Each clone was plated at a density of $2\times10^4$ cells/well in a 24 well plate. Each well contained 1 ml of medium containing RPMI-1640, 10% dialyzed FCS and MTX. The clones were grown in the presence of either 3, 10, 30, 60 or 90 nM MTX. Non-transfected BW5147.G.1.4 cells were also grown in the above range of MTX as a control. Clones which grew in MTX levels at least 2-3 fold higher than that tolerated by the parental BW5147.G.1.4 (typically less than or equal to 10 nM MTX) were selected for further analysis. Four of the selectant clones grew in greater than or equal to 30 nM MTX and were retained; these clones are the primary transfectants chosen for amplification. All 4 clones which grew in >30 nM MTX were analyzed for the ability to express DR molecules on the surface by an ELISA. The cell surface ELISA was performed as follows.

Between 5 and $20\times10^4$ cells/well were put into a U-bottom 96 well plate. The cells were pelleted in a centrifuge using a plate carrier at 1000 rpm for 3 min at 4° C. The supernatant was flicked from the wells, the cells dispersed from their pellets by tapping and the plate was placed on ice. Fifty microliters of a 1/200 dilution of biotinylated mcab L243 (Becton-Dickinson) in staining media [Hank's Basic Salt Solution (Irvine Scientific), 10 mM HEPES, pH 7, 5% calf serum] was added to each well. The cells were incubated with the biotinylated mcab for 20 min on ice. Ice cold staining media was added to a final volume of 200 µl/well. The cells were pelleted and the supernatant flicked out and the pellets dispersed as described above. The cells were washed twice more with 200 μl/well of ice cold staining media. Fifty microliters of a 1/1000 dilution of Horseradish peroxidase conjugated Avidin (Vector Laboratories, Burlingame, Calif.) was added per well and incubated on ice for 20 min. Ice cold staining media was added to a final volume of 200 μl/well. The cells were pelleted and the supernatant flicked out and the pellets dispersed as described above. The cells were washed three more with 200 μl/well of ice cold staining media. After the final wash, the plate was again tapped to disperse the cell pellets and each well received 200 μl of freshly made OPD Substrate Solution [16 mM Citric Acid, 34 mM Sodium Citrate, 0.01% $H_2O_2$, 1 mg/ml O-phenylene diamine dihydrochloride (Sigma)]. The plate was allowed to sit at room temp for 10 to 20 min. The cells were then pelleted at 1000 rpm for 3 min at 4° C. One hundred microliters of supernatant from each well was transferred to a fresh, flat bottom 96 well plate (Costar) and the plate was read on a VMAX microplate reader (Molecular Devices, Menlo Park, Calif.) at a wavelength of 450 nm.

Figure 18:
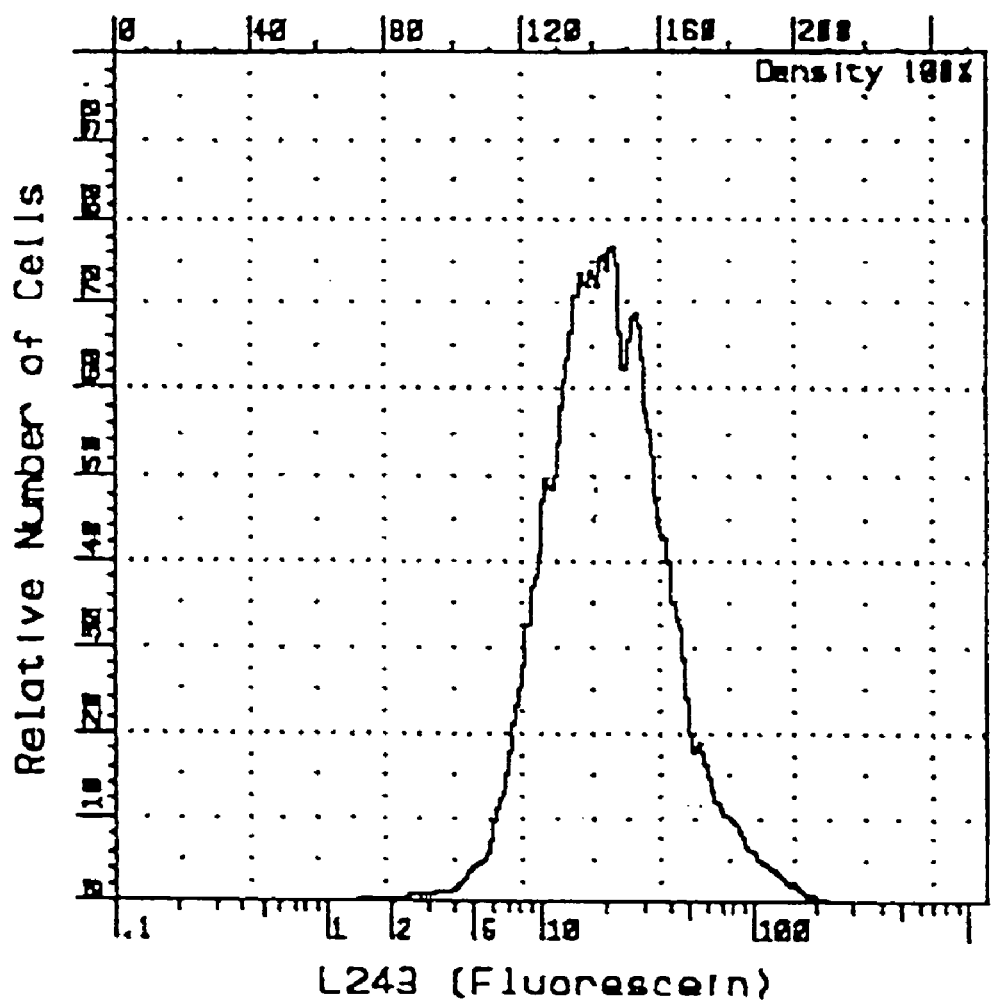
FIG. 18 is a histogram showing the clone 5 cells selected for growth in 80 nM MTX stained with the L243 monoclonal antibody.

All four clones expressed the DR molecule as judged by ELISA analysis. Each of these four clones was grown in the highest MTX level at which obvious growth still occurred as determined by the test for MTX sensitivity above; the levels ranged from 30 to 80 nM MTX. The clones were then again checked for the ability to express DR on the cell surface by staining with L243 and FACS analysis as above. One out four first round amplificants, clone 5, showed both an increased resistance to MTX and the best corresponding increase in DR expression (all four clones showed increased DR expression). The histogram of cells from clone 5 grown in 80 nM MTX is shown in FIG. 18. In FIG. 18 the log of fluorescein (x axis) is plotted against the relative number of cells in the sample. Growth in 80 nM MTX represents the first round of amplification for clone 5.

Figure 19:
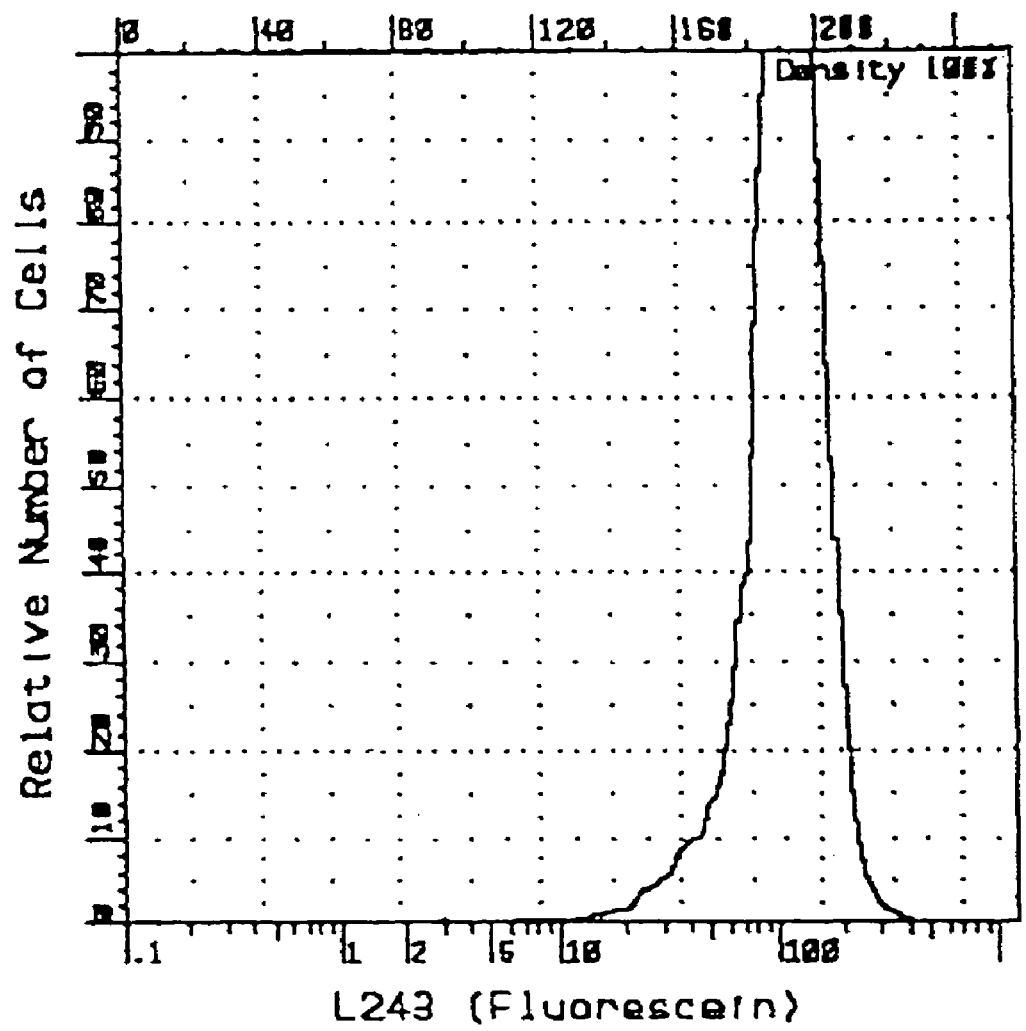
FIG. 19 is a histogram showing the clone 5 cells selected for growth in 320 nM MTX stained with the L243 monoclonal antibody.
Figure 20:
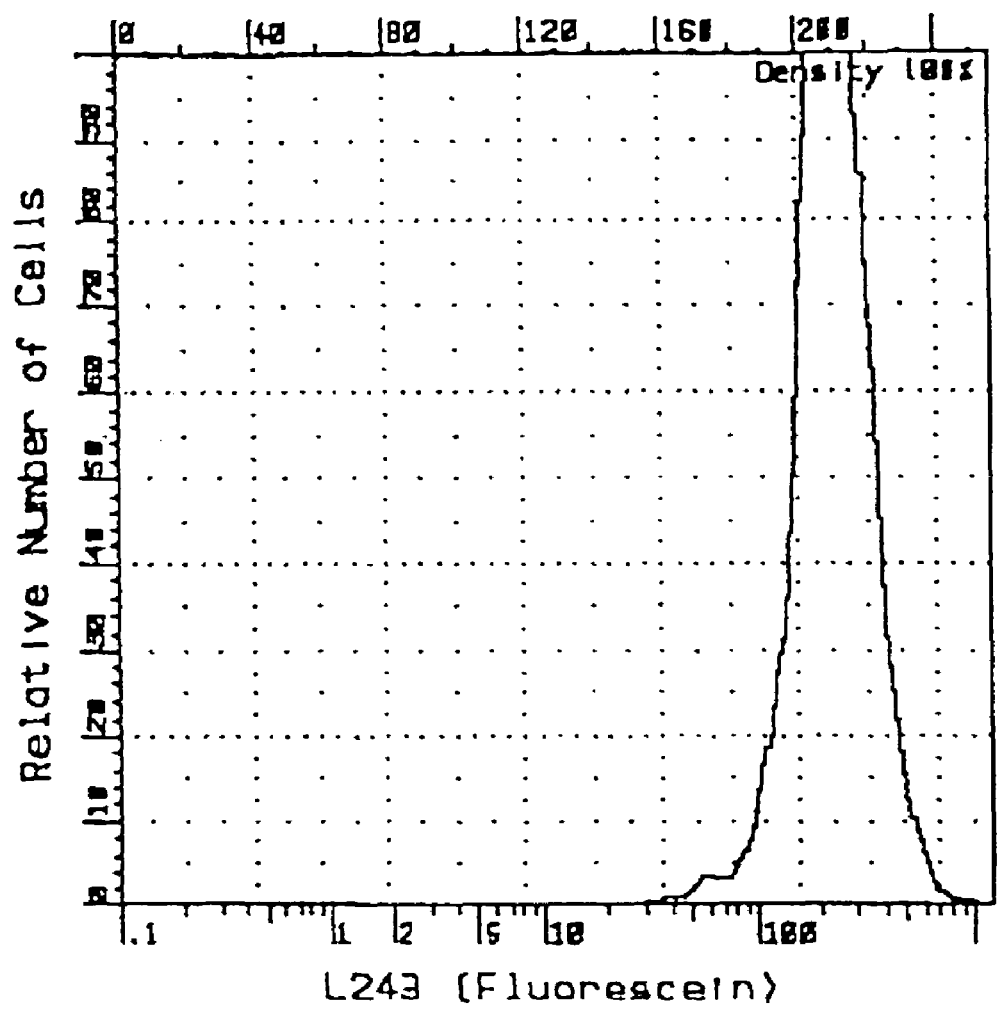
FIG. 20 is a histogram showing the clone 5 cells selected for growth in 1 μM MTX stained with the L243 monoclonal antibody.

The three clones which grew in higher levels of MTX but which did not show a high coincidental increase in the expression of DR were discarded. Clone 5 was retained and subjected to further rounds of amplification by grow in increasing concentrations of MTX. FIGS. 19 and 20 show histograms of cells from clone 5 grown in 320 nM and 1 μM MTX, respectively. The cells were stained with L243 and analyzed on a FACScan as described above. As is shown in FIGS. 19 and 20, clone 5 continued to show a coincidental increase in DR expression and increased MTX-resistance. Integration of the area under the peaks of fluorescence from each of FIGS. 17-20 showed that clone 5 achieved a 30-fold increase in DR expression between the initial selectant stage and the third round of amplification (1 μM MTX$^r$).

Continued analysis of clone 5 demonstrated that it is extremely stable. Clone 5 grown in 1 μM MTX (referred to as the 1 μM MTX amplificant of clone 5) can be grown for 2 to 3 weeks in medium lacking MTX without any apparent drop in expression of DR (as judged by cell surface ELISA assays).

EXAMPLE 9

Production of Large Quantities of Soluble T Cell Receptor and Class II MHC Molecules Tumors of B and T cells (i.e., lymphomas and leukemias) are often clonal in nature and therefore the Ig or TCR carried on the surface of the tumor cell can serve as a tumor-specific antigen. Soluble forms of the tumor-specific Ig have been used to immunize patients in order to invoke an immune response against the tumor cell [Kwak et al. (1992) N. Engl. J. Med. 327:1209 and Hsu et al. (1996) Nature Med. 2:52]. The therapeutic use of soluble forms of a patient's tumor-specific antigen requires that large quantities of the soluble antigen be produced in a short period of time so that immunization of the patient can be carried out quickly (i.e., before the patient's disease progress to a point that therapy is pointless). Large quantities of soluble class II MHC molecules are required to allow treatment of autoimmune disease using soluble class II molecules complexed with specific peptides [Sharma, et al. supra].

The methods of the present invention allow the production of large quantities of soluble forms of class II MHC molecules and TCR to be produced in a rapid manner. These methods allow for the production of customized tumor cell vaccines comprising soluble TCR for the treatment of lymphoma and leukemia patients as well as the production of soluble class II MHC molecules for the treatment of autoimmune disease. DNA sequences encoding the chains comprising the extracellular domains of the TCR or class II MHC molecules expressed by the patient's tumor cells are cloned using the PCR. These sequences are joined to sequences encoding a thrombin cleavage site followed by the transmembrane and cytoplasmic domains of either the α or β chain of a mammalian class II MHC heterodimer. The sequences encoding each chain of the chimeric TCR or class II MHC molecules (i.e., the genes of interest) are inserted into any of the SD7 vectors described herein (e.g., pSRαSD7; Ex. 1) and the resulting vectors are co-transfected into BW5147.G.1.4 cells along with an amplification vector (e.g., pSSD7-DHFR; Ex. 3) and, if so desired, a selection vector (e.g., pMSD5-HPRT; Ex. 2). The transfected cells will express the chimeric TCR or class II MHC molecules on the cell surface. The transfected cells are subjected to selection and/or amplification in order to produce amplified cell lines which express large quantities of the chimeric TCR or class II MHC molecules on the cell surface. These chimeric proteins can be cleaved from the cell surface to produce soluble TCR or class II MHC molecules by digestion with thrombin.

The following discussion illustrates the production of soluble TCR or class II MHC proteins using amplified cell lines. An analogous approach can be used to produce soluble forms of any multi-chain cell surface protein.

a. Construction of Vectors Encoding Chimeric TCR Chains

Sequences encoding chimeric α chain of a TCR are constructed which comprise (from the amino- to carboxyl-termini) the extracellular domains of the α chain of a TCR followed by 21 amino acids derived from the thrombin receptor which comprise a thrombin cleavage site followed by 41 amino acids comprising the transmembrane and cytoplasmic domains of the class II MHC molecule DRα. An analogous construct is used to construct a chimeric β chain of a TCR comprising (from the amino- to carboxyl-termini) the extracellular domains of the β chain of a TCR followed by 21 amino acids derived from the thrombin receptor which comprise a thrombin cleavage site followed by 42 amino acids comprising the transmembrane and cytoplasmic domains of the class II MHC molecule DRβ1. Any mammalian class II MHC αβ pair can be used to provide sequences encoding the transmembrane and cytoplasmic domains of the MHC molecule which permit the association of the chimeric TCR chains. While, the number of amino acid residues comprising the transmembrane and cytoplasmic domains of the α and β chains of the class II MHC molecules differs by one, both MHC junctions are at the third amino acid residue from the beginning of the transmembrane domain. This arrangement preserves the glutamate residue from the α chain and the lysine from the β chain which have been shown to have a positive effect upon heterodimer formation of class II MHC molecules [Cosson and Bonifacino (1992) Science 258:659].

A vector containing sequences encoding the thrombin and class II MHC sequences is constructed by synthesizing the DNA sequences listed in SEQ ID NO:31 and SEQ ID NO:33. The amino acid sequence encoded by SEQ ID NO:31 is listed in SEQ ID NO:32 and amino acid sequence encoded by SEQ ID NO:33 is listed in SEQ ID NO:34.

SEQ ID NO:31 encodes the thrombin site-DRα chimeric sequence and SEQ ID NO:33 encodes the thrombin site-DRβ1 chimeric sequence. Inspection of these sequences shows that the sequences at the 5' end which encodes the thrombin site contains the recognition site for the following restriction enzymes: BamHI, PvuI and FspI. A NotI site is located at the 3' end of the thrombin site-DRβ$_1$ chimeric sequences. The synthetic DNA is inserted into any suitable vector (e.g., pUC 18 or pUC 19) as a BamHI-NotI fragment. The thrombin site encoded by these sequences is very efficiently cleaved by thrombin due to the presence of the hirudin-like domain following the thrombin cleavage site [Vu et al. (1991) Cell 64:1057 and Vu et al. (1991) Nature 353:674].

DNA sequences encoding TCR chains are isolated from double-stranded cDNA generated from a cell line or a patient's tumor (double-stranded cDNA may be generated using the protocol set forth in Example 3; oligo d(T) may be used to prime first strand cDNA synthesis in place of the SBNSSdT primer). The double stranded cDNA is then used in PCRs which contain primer pairs designed to amplify either the α chain or the β chain of the human TCR. The PCR is conducted using 1 unit/100 µl reaction Pfu polymerase (Stratagene) in the reaction buffer provided by Stratagene, 5 ng/100 µl of a cloned template or 25 ng/100 µl of ds-cDNA derived from polyA+RNA isolated from a cell line or tumor, 0.1 mM of each of the four dNTPs and 0.5 µM of each primer. The PCR is cycled at 94° C. for 15 sec followed by 60° C. for 30 sec followed by 75° C. for 2 min for 21 cycles.

The 5' primer used to amplify TCR sequences contains the following restriction sites at the 5' end of the primer: XbaI, EcoRI and MluI followed 18-21 nucleotides comprising a consensus sequence derived from the V regions of human TCRs. Therefore the 5' primer will comprise sets of degenerate primers having the following sequence: 5'-TCTAGAAT-TCACGCGT(N)$_{18-21}$-3', where N is any nucleotide and the 18-21 nucleotide stretch represents a consensus V region sequence. The following 3' primer is used in conjunction with the above-described consensus 5' primer to amplify the extracellular domains of human TCR α chains: 5'-CGATCGTG-GATCCAAGTTTAGGTTCGTATCTGTTTCAAA-3' (SEQ ID NO:35). The 3' connection for the TCR α chain is made after the asparagine which appears at position 10 of the constant (C) region of the α chain. The following 3' primer is used in conjunction with the above-described consensus 5' primer to amplify the extracellular domains of human TCR β chains: 5'-CGATCGAGGATCC AAGATGGTGGCAGACAG-GACC-3' (SEQ ID NO:36). The 3' connection for the TCR α chain is made after the isoleucine which appears at position 147 of the C region of the β chain. These 3' primers are designed such that in both cases (i.e., for both the α and the β chain of the TCR) the connection between the extracellular domains of the TCR with the thrombin site is made at the fourth amino acid residue from the apparent beginning of the respective transmembrane regions of the TCR chains. Both 3' primers contain recognition sites for PvuI and BamHI at their 5' ends. The restriction sites located at the 5' ends of the primers allows the resulting PCR products comprising a TCR chain to be removed as a XbaI or EcoRI or MluI (5' end)-BamHI or PvuI (3' end) fragment and joined with the appropriate thrombin-transmembrane DNA sequence [as a BamHI or PvuI (5' end)-NotI (3' end) fragment] and inserted into any of the SD7 vectors (e.g., pSRαSD7). The resulting expression vectors (one for each of the α chains and the β chains of the chimeric TCR) are co-transfected using electroporation into BW5147.G.1.4 cells along with the amplification vector pSSD7-DHFR (Ex. 3) and the selection vector pMSD5-HPRT (Ex. 2). The amount of each plasmid DNA to be used (the plasmids are linearized before electroporation), the conditions for electroporation, selection and amplification are described above. The resulting amplified cell lines will express the chimeric TCR heterodimer on the surface of the cell. The TCR is solubilized by digestion of the cells with thrombin. The thrombin solubilized extracellular domains will have 3 (TCR or 4 (TCR α) novel amino acids at the C-termini.

b. Construction of Vectors Encoding Chimeric Class II MHC Chains

Sequences encoding a chimeric α chain of a class II MHC protein are constructed which comprise (from the amino- to carboxyl-termini) the extracellular domains of the α chain of DRα followed by 21 amino acids derived from the thrombin receptor which comprise a thrombin cleavage site followed by 41 amino acids comprising the transmembrane and cytoplasmic domains of the class II MHC molecule DRα. An analogous construct is used to construct a chimeric β chain of a class II MHC protein comprising (from the amino- to carboxyl-termini) the extracellular domains of the β chain of DRβ$_1$ followed by 21 amino acids derived from the thrombin receptor which comprise a thrombin cleavage site followed by 42 amino acids comprising the transmembrane and cytoplasmic domains of the class II MHC molecule DRβ$_1$.

Sequences encoding the extracellular domains of the α and β chains of a class II MHC heterodimer are isolated using the PCR as described above with the exception that the following primer pairs are used in the PCR. Sequences encoding the extracellular domain of DRα are amplified using 5'-ACGCGTCCACCATGGCC ATAAGTGGAGTCCCT-3' (SEQ ID NO:37) (this primer contains a MluI site at the 5' end) and 5'-GGATCCAACTCTGTAGTCTCTGGGAGAG-3' (SEQ ID NO:38) (this primer contains a BamHI site at the 5' end). The use of these primers allows the connection of the extracellular domain of DRα with the thrombin site-transmembrane sequences (described above) after amino acid 191, a glutamate residue in the mature (i.e., after the removal of the signal sequence) DRα protein.

Sequences encoding the extracellular domain of DRβ$_1$ are amplified using: 5'-ACGCGTCCACCATGGTGTGTCT-GAAGCTCCTG-3' (SEQ ID NO:39) (this primer contains a MluI site at the 5' end) and 5'-GGATCCAACTTGCTCTGT-GCA GATTCAGA-3' (SEQ ID NO:40) (this primer contains a BamHI site at the 5' end). The use of these primers allows the connection of the extracellular domain of DRβ with the thrombin site-transmembrane sequences (described above) after amino acid 198, a lysine residue, in the mature DRβ protein.

The restriction sites located at the 5' ends of the primers allows the resulting PCR products comprising the class II MHC chains to be removed as a MluI (5' end)-BamHI (3' end) fragment and joined with the appropriate thrombin-transmembrane DNA sequence [as a BamHI (5' end)-NotI (3' end) fragment] and inserted into any of the SD7 vectors (e.g., pSRαSD7). The resulting expression vectors (one for each of the α chains and the β chains of the chimeric class II MHC protein) are co-transfected using electroporation into BW5147.G.1.4 cells along with the amplification vector pSSD7-DHFR (Ex. 3) and the selection vector pMSD5-HPRT (Ex. 2). The amount of each plasmid DNA to be used (the plasmids are linearized before electroporation), the conditions for electroporation, selection and amplification are described above. The resulting amplified cell lines will express the chimeric class II heterodimer on the surface of the cell. The class II MHC heterodimer is solubilized by digestion of the cells with thrombin.

EXAMPLE 10

Production of Custom Multivalent Vaccines for the Treatment of Lymphoma and Leukemia The existing approach toward vaccination (i.e., active immunotherapy) of B-cell lymphoma and leukemia involves the production of a custom vaccine comprising autologous immunoglobulin idiotype which corresponds to the most abundant antibody molecule expressed on the surface of the B-cell tumor. An analogous approach for the treatment of T-cell lymphomas and leukemias would involve the production of a custom vaccine comprising autologous T cell receptor (TCR) idiotype which corresponds to the most abundant TCR molecule expressed on the surface of the T-cell tumor.

Existing methods for the production of custom vaccines for the treatment of B-cell lymphoma employ the "rescue fusion" technique. The rescue fusion technique involves the removal of lymphoma cells by surgical biopsy. The tumor cells are then fused with the heterohybridoma cell line K6H6/B5 which has lost the ability to secrete endogenous Ig. Hybrid cells which secrete Ig corresponding to the immunophenotype of the tumor sample are expanded and the secreted Ig is purified for use as a vaccine [Kwak et al. (1992), supra]. The Ig produced by rescue fusion represents a single Ig derived from the patient's tumor; this Ig is presumably the predominant Ig expressed by the tumor. Thus, vaccines produced by rescue fusion are monovalent and do not represent the full complexity of Ig expressed by tumors which contain somatic variants.

In order to produce multivalent custom vaccines from small numbers of cells quickly and efficiently, the gene amplification techniques described in the preceding examples are employed. In this example, methods for the production of tumor-specific Ig derived from a B-cell lymphoma patient are provided. However, the general approach outlined herein is applicable for the production of tumor-specific proteins generally (i.e., production of soluble TCR for treatment of T cell tumors, production of Ig for treatment of B cell leukemias, etc.).

In this novel approach, the variable regions corresponding to the patient's Ig ($V_H$ and $V_L$) are molecularly cloned and joined to an appropriate constant region gene contained within an expression vector. Expression plasmids containing the patient's $V_H$ region(s) joined to either a Cγ3 or Cγ4 sequence and expression plasmids containing the patient's $V_L$ region(s) joined to either a Cκ or Cλ2 sequence are cotransfected (via electroporation) along with the selectable and amplifiable marker pM-HPRT-SSD9-DHFR into the desired cell line (e.g., BW5147.G.1.4). The transfected cells are then subjected to selection and amplification as described in the preceding examples. The method outlined below permits the production of a multivalent vaccine which reflects the degree of somatic variation found within the patient's tumor. These novel multivalent vaccine preparations provide superior vaccines for the treatment of B-cell lymphoma and should reduce the rate of relapse observed when the current generation of monovalent vaccines are employed.

a) Construction of Expression and Selection/Amplification Plasmids

For the following constructions, unless otherwise stated, all enzymes are obtained from New England Biolabs (NEB) and used in conjunction with the buffers and reaction conditions recommended by the manufacturer.

i) Construction of pSRαSD9

Figure 21:
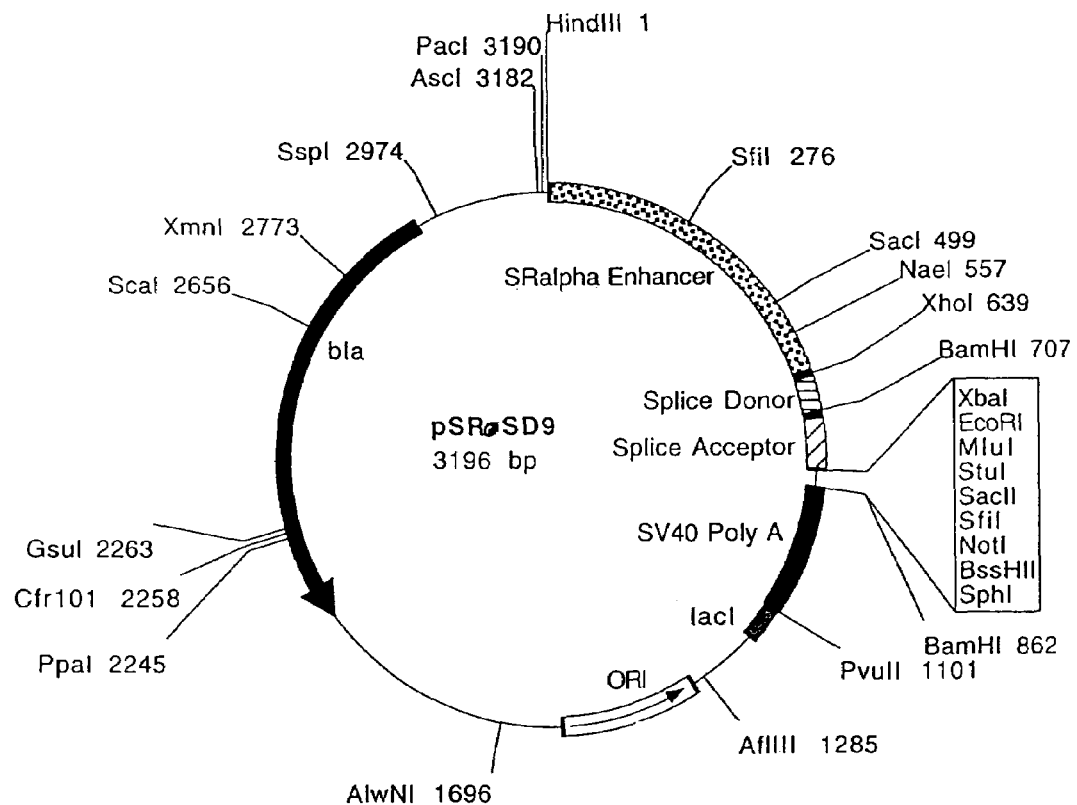
FIG. 21 shows the map of the expression vector pSRαSD9. Selected restriction enzyme sites are indicated.

Two micrograms of pSRαSD7 (Ex. 1) is cut with SalI and HindIII (NEB enzymes, buffers & conditions). The plasmid is spermine precipitated (Ex. 5) and resuspended in 34 µl H$_2$O and 4 µl of 10× T4 DNA ligase buffer. Equal molar amounts (6.3 ng each) of the unphosphorylated oligonucleotides SXAPH5 (SEQ ID NO:42) and SXAPH3 (SEQ ID NO:43) are added. The reaction is chilled on ice, 400 units of T4 DNA ligase is added and the tube is placed at 14° C. overnight. The ligation is transformed into bacteria and clones screened for the presence of the added AscI & PacI restriction sites. The resulting plasmid is called pSRαSD9. FIG. 21 provides a schematic map of pSRαSD9.

ii) Construction of pSRαSD9CG3C, pSRαSD9CG4C, pSRαSD9CKC and pSRαSD9CL2C

The plasmids pSRαSD9CG3C, pSRαSD9CG4C, pSRαSD9CKC and pSRαSD9CL2C contain sequences encoding the Cγ3, Cγ4, Cκ or Cλ2 constant regions, respectively. The constant regions contained within these expression vectors are encoded by synthetic DNA sequences which encode the same amino acid sequences as that found in the native proteins; however, the DNA sequences have been modified to utilize codons which are found most frequently in highly expressed mammalian proteins [Haas et al. (1996) Curr. Biol. 6:315 and Zolotukhin et al. (1996) J. Virol. 70:4646]. The DNA sequence encoding the Cγ3 region is listed in SEQ ID NO:44; the amino acid sequence encoded by SEQ ID NO:44 is listed in SEQ ID NO:45. The DNA sequence encoding the Cγ4 region is listed in SEQ ID NO:46; the amino acid sequence encoded by SEQ ID NO:46 is listed in SEQ ID NO:47. The DNA sequence encoding the Cκ region is listed in SEQ ID NO:48; the amino acid sequence encoded by SEQ ID NO:48 is listed in SEQ ID NO:49. The DNA sequence encoding the Cλ2 region is listed in SEQ ID NO:50; the amino acid sequence encoded by SEQ ID NO:50 is listed in SEQ ID NO:51.

Double stranded DNA corresponding to SEQ ID NOS:44, 46, 48 and 50 are synthesized (Operon Technologies). Each synthetic DNA sequence is cut with NotI and BglII, run through a 0.8% SeaPlacque Agarose gel (FMC) and recovered using β-agarase as described below. Each C region sequence is ligated to the two DNA restriction fragments generated from pSRαSD9 as follows. A 2 µg aliquot of pSRαSD9 is cut with HindIII and BamHI and a 2314 bp band is isolated. A second 2 µg aliquot of pSRαSD9 is cut with HindIII and NotI and an 854 bp band is isolated. These fragments are isolated by running each digest on a 0.8% SeaPlacque Agarose (FMC), the appropriate bands are cut out and combined in a microfuge tube. The agarose is remove by β-Agarase (NEB) digestion and the DNA is recovered by isopropanol precipitation exactly as indicated by NEB.

Figure 22:
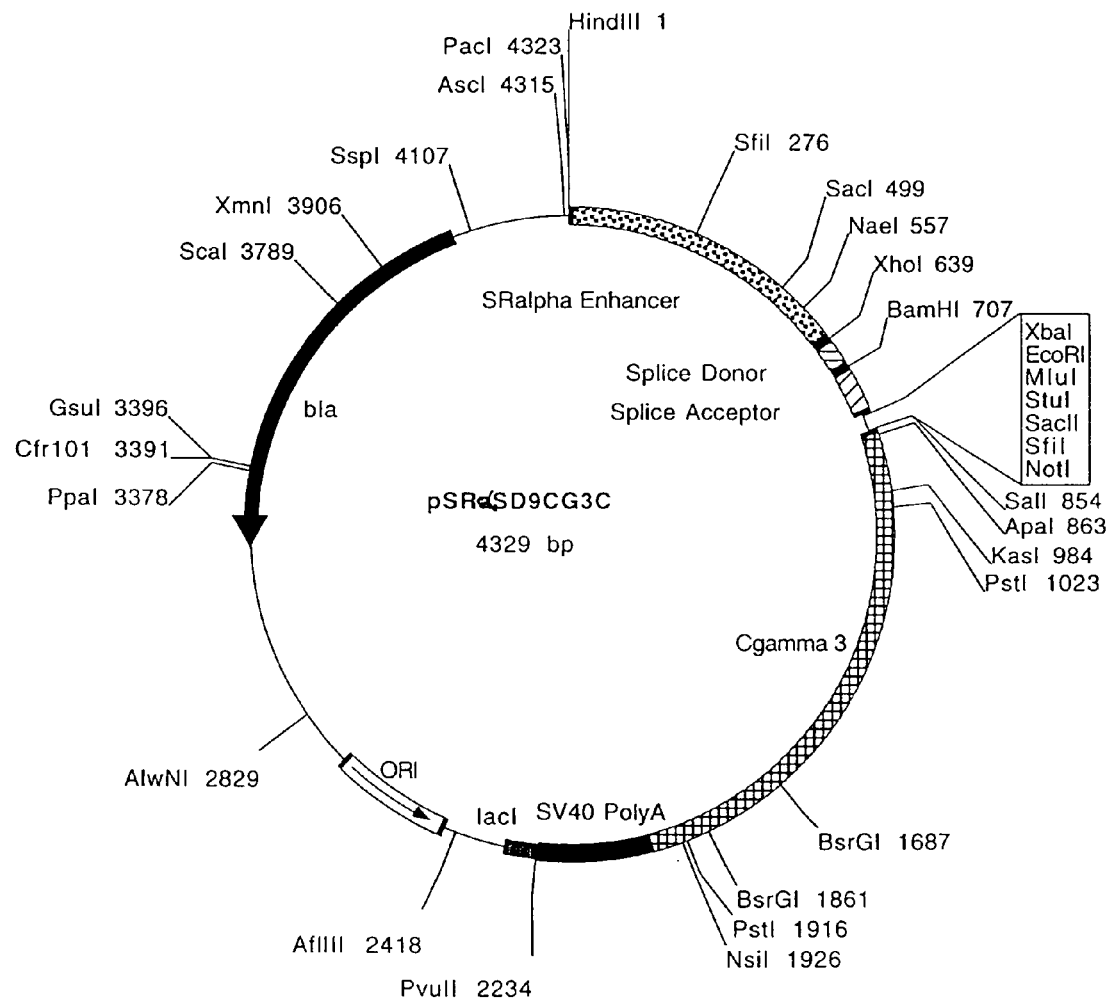
FIG. 22 shows the map of the expression vector pSRαSD9CG3C. Selected restriction enzyme sites are indicated.
Figure 23:
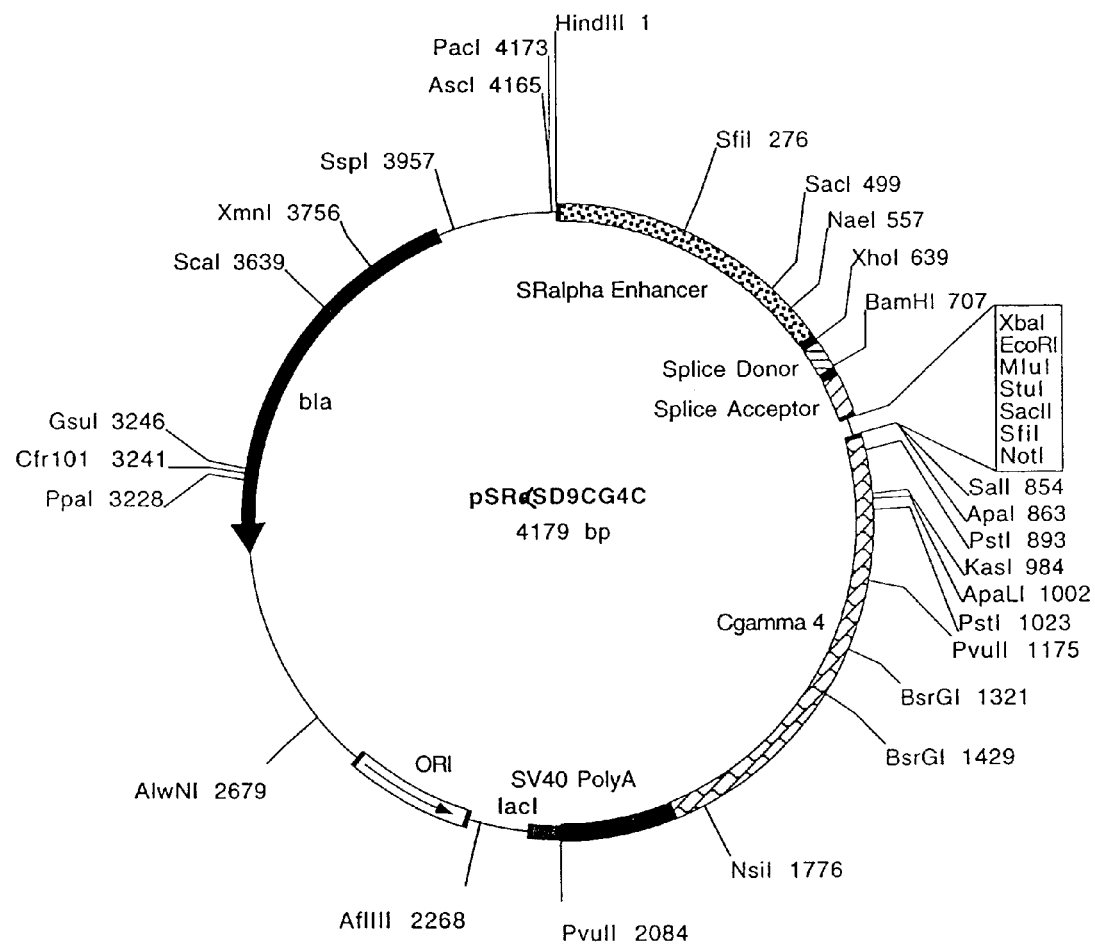
FIG. 23 shows the map of the expression vector pSRαSD9CG4C. Selected restriction enzyme sites are indicated.
Figure 24:
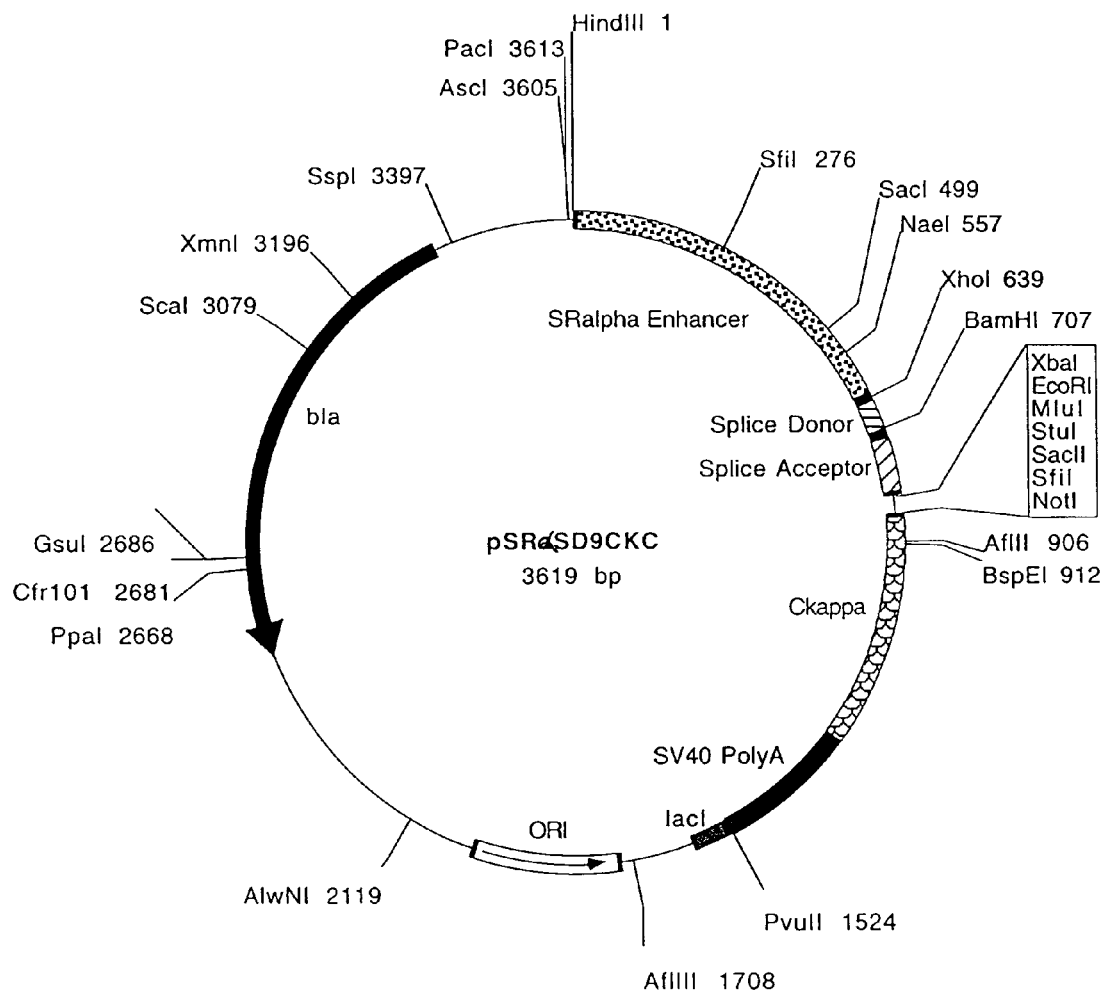
FIG. 24 shows the map of the expression vector pSRαSD-CKC. Selected restriction enzyme sites are indicated.
Figure 25:
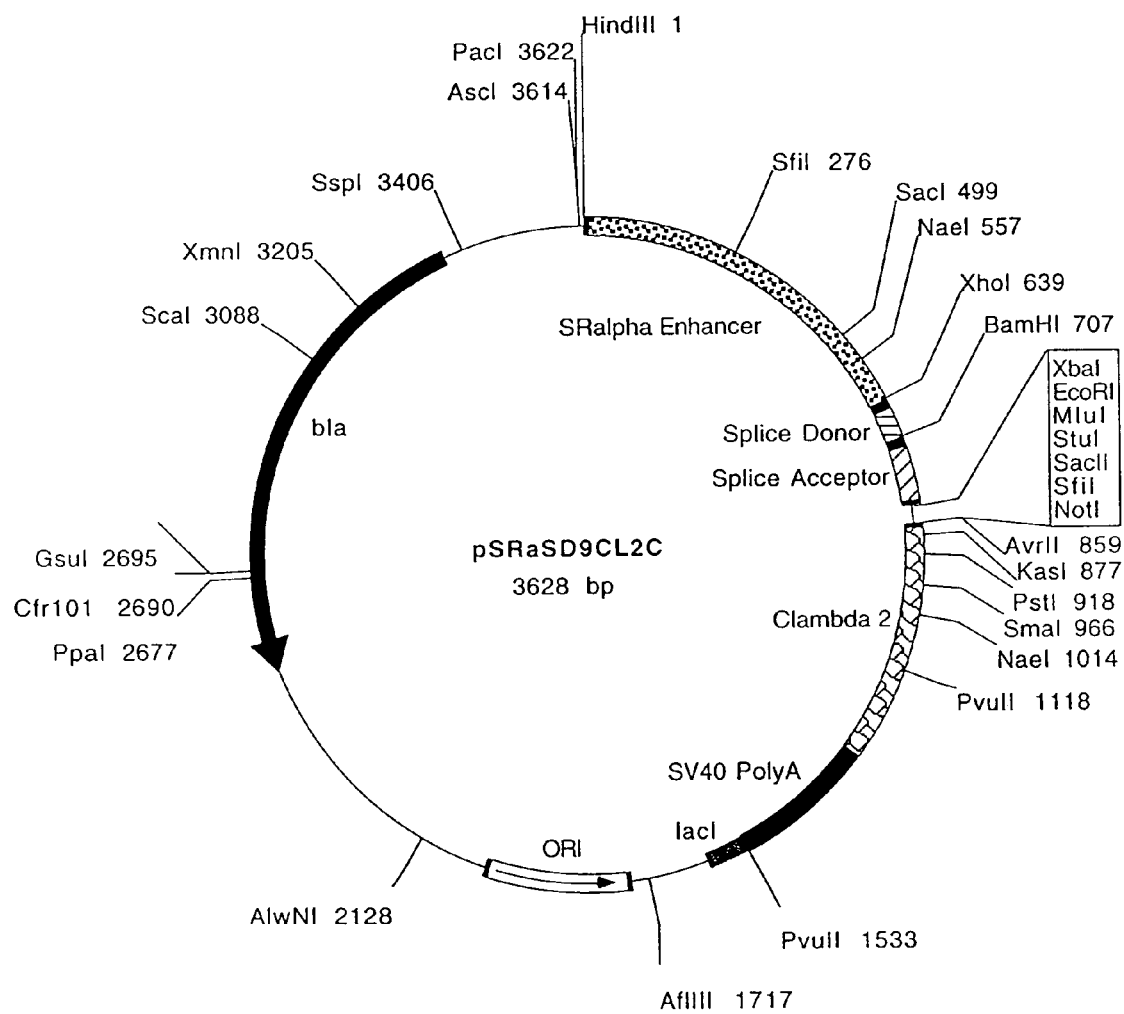
FIG. 25 shows the map of the expression vector pSRαSDCL2C. Selected restriction enzyme sites are indicated.
Figure 26:
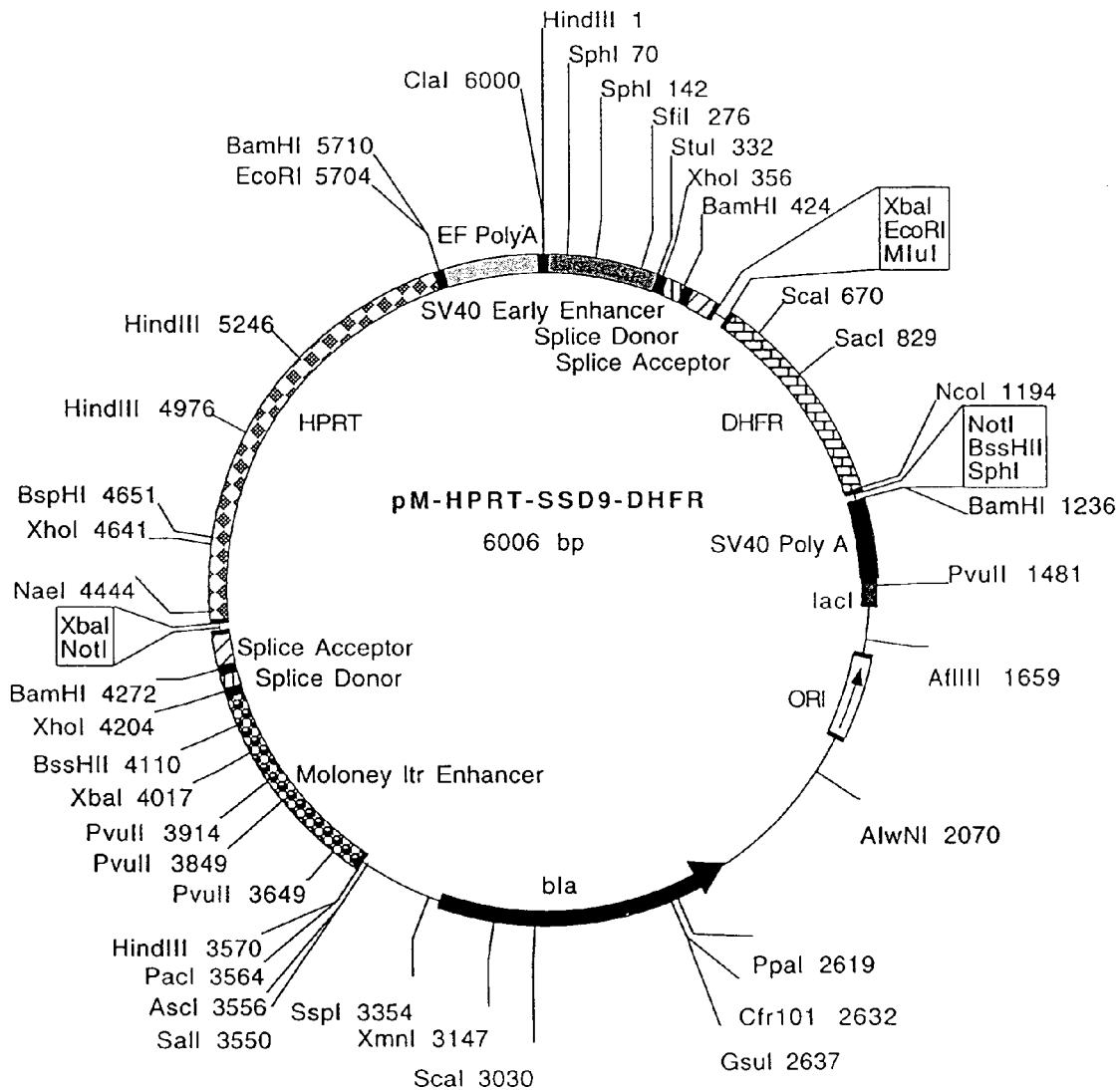
FIG. 26 shows the map of the selection and amplification vector pM-HPRT-SSD9-DHFR. Selected restriction enzyme sites are indicated.

The ligation of SEQ ID NO:44 (digested with NotI and BglII) with the above fragments of pSRαSD9 generates pSRαSD9CG3C (map shown in FIG. 22). The ligation of SEQ ID NO:45 (digested with NotI and BglII) with the above fragments of pSRαSD9 generates pSRαSD9CG4C (map shown in FIG. 23). The ligation of SEQ ID NO:46 (digested with NotI and BglII) with the above fragments of pSRαSD9 generates pSRαSD9CKC (map shown in FIG. 24). The ligation of SEQ ID NO:47 (digested with NotI and BglII) with the above fragments of pSRαSD9 generates pSRαSD9CL2C (map shown in FIG. 25).

iii) Construction of pM-HPRT-SSD9-DHFR pM-HPRT-SSD9-DHFR contains the hprt gene under the control of the Moloney enhancer/promoter and the dhfr gene under the control of the SV40 enhancer/promoter. pM-HPRT-SSD9-DHFR is constructed by first subcloning the HPRT cDNA (Ex. 2) into pMSD8 (described below) to create pMSD8-HPRT. The small DNA fragment located between the SalI and HindIII sites on pMSD8-HPRT is then replaced with a sequence containing AscI and PacI sites as follows. pMSD8-HPRT is digested with SalI and HindIII and the SXAPH5 and SAXPH3 oligonucleotides (SEQ ID NOS:42 and 43) are ligated to the ends of the digested pMSD8-HPRT (as described in section i above) to create pMSD9-HPRT. The ~2450 bp SalI-ClaI fragment containing the AscI and PacI sites, the Moloney enhancer/promoter, the HPRT cDNA and the EF1α poly A region is inserted between the SalI and ClaI sites of pSSD7-DHFR (Ex.) to generate pM-HPRT-SSD9-DHFR. FIG. 26 provides a map of pM-HPRT-SSD9-DHFR.

pMSD8 is similar to pMSD5 but contains the poly A site from the human elongation factor 1α gene. pMSD8 was constructed as follows: A 292 bp fragment containing the poly A site from the human elongation factor 1α gene (SEQ ID NO:78) was isolated from MOU cell (GM 08605, NIGMS Human Genetic Mutant Cell Repository, Camden, N.J.) genomic DNA using PCR. MOU genomic DNA was isolated using conventional techniques. The PCR was conducted using 10 µg MOU genomic DNA and 1 µM final concentration of each primer in a 400 µl reaction. Reaction conditions were 94° C. for 1 minute, 60° C. for 1 minute, 72° C. for 1.5 minutes, 30 cycles. Taq DNA polymerase was obtained from Perkin-Elmer. The following oligonucleotides were used to prime the PCR: 5EF1αPolyA: 5' GAATTCTTTTTTGCGT-GTGGCAG 3' (SEQ ID NO:79) and 3EF1αPolyA: 5' ATC-GATATTCCTTCCCCTTCC 3' (SEQ ID NO:80). The 3EF1αPolyA oligonucleotide generates a ClaI site at the 3' end of the poly A site and the 5EF1αPolyA oligonucleotide generates an EcoRI site at the 5' end of the poly A site. Digestion of the PCR product with EcoRI and ClaI yields a 292 bp EcoRI/ClaI fragment.

pSSD5 (Ex. 1) was digested with PvuII and a ClaI linkers (NEB, unphosphorylated) were ligated to the PvuII ends to convert the PvuII site located at the 3' end of the SV40 poly A site to a ClaI site. The resulting construct was then digested with SalI and ClaI and the ~2.1 kb fragment containing the plasmid backbone (e.g., the Amp$^R$ gene and plasmid ORI) was isolated and ligated to an ~870 bp SalI/EcoRI fragment containing the Moloney enhancer/promoter, splice donor/acceptor and polylinker isolated from pMSD5 (Ex. 1) together with the 292 bp EcoRI/ClaI fragment containing the poly A site of the human elongation factor 1α gene to generate pMSD8.

b) Collection of Tumor Cells

Cells are collected by either surgical biopsy of enlarged lymph nodes or by fine needle biopsy of effected lymph nodes. The biopsy sample is rapidly frozen on dry ice.

c) Isolation of RNA from Tumor Cells

RNA is isolated from the biopsy sample by using a variety of standard techniques or commercially available kits. For example, kits which allow the isolation of RNA from tissue samples are available from Qiagen, Inc. (Chatsworth, Calif.) and Stratagene (LaJolla, Calif.), respectively. Total RNA may be isolated from tissues and tumors by a number of methods known to those skilled in the art and commercial kits are available to facilitate the isolation. For example, the RNeasy® kit (Qiagen Inc., Chatsworth, Calif.) provides protocol, reagents and plasticware to permit the isolation of total RNA from tissues, cultured cells or bacteria, with no modification to the manufacturer's instructions, in approximately 20 minutes. Should it be desirable to further enrich for messenger RNAs, the polyadenylated RNAs in the mixture may be specifically isolated by binding to an oligo-deoxythymidine matrix, through the use of a kit such as the Oligotex® kit (Qiagen). Comparable isolation kits for both of these steps are available through a number of commercial suppliers.

In addition, RNA may be extracted from samples, including biopsy specimens, conveniently by lysing the homogenized tissue in a buffer containing 0.22 M NaCl, 0.75 mM MgCl$_2$, 0.1 M Tris-HCl, pH 8.0, 12.5 mM EDTA, 0.25% NP40, 1% SDS, 0.5 mM DTT, 500 u/ml placental RNAse inhibitor and 200 µg/ml Proteinase K. Following incubation at 37° C. for 30 min, the RNA is extracted with phenol: chloroform (1:1) and the RNA is recovered by ethanol precipitation.

A particularly preferred method for the isolation of total cellular RNA from patient tumor samples is the RNAzol method (Teltest, Inc., Friendswood, Tex.) which is performed according to the manufacturer's instructions.

d) Cloning of Ig Genes from Tumor Cells

Because the first and third complementarity determining regions (CDRs) of rearranged immunoglobulin genes are flanked by conserved sequences, it is possible to design PCR primers capable of amplifying cDNA for the variable regions from mRNA derived from Ig-expressing tumor cells without any specific knowledge of the nucleotide sequence of that specific antibody. Primers suitable for isolating the variable regions from a patient's tumor are provided below.

Using total cellular RNA isolated from the tumor, double stranded (ds) cDNA is generated as described in Example 3 with the exception that 20 µg of total cellular RNA is used instead of poly A$^+$ RNA. Five percent of the ds cDNA preparation is used for each PCR reaction. [Alternatively, ds cDNA may be produced using the technique of RT-PCR (reverse transcription-PCR); kits which permit the user to start with tissue and produce a PCR product are available from Perkin Elmer (Norwalk, Conn.) and Stratagene (LaJolla, Calif.). The RT-PCR technique generates a single-stranded cDNA corresponding to a chosen segment of the coding region of a gene by using reverse transcription of RNA; the single-stranded cDNA is then used as template in the PCR].

PCR reactions are carried out in a final volume of 50 µl and contain 1×Pfu Buffer (Stratagene), all 4 dNTPs at 100 µM each, primers at 0.5 µM each, Pfu polymerase (Stratagene) and 5% of the ds cDNA preparation. The reactions are thermocycled as follows: 94° C., 15 sec; 60° C., 30 sec; 75° C., 1.5 min for 15-30 cycles. Aliquots (5 µl) are removed after 15, 20, 25 and 30 cycles to examine the appearance of the primary PCR product. Preparative reactions of 200 µl using the correct V region primers will be then run for cloning purposes.

Prior to conducting a PCR reaction to obtain Ig sequences from a patient's tumor, the tumor is immunophenotyped using commercially available antibodies to determine the heavy chain and light chain isotypes; this allows the number of PCRs to be minimized. For example, if the Ig expressed by the patient's tumor utilizes a µ heavy chain and a κ light chain, then PCR reactions described below which contain Cγ and Cλ primers need not be run. However, the use of PCR primers corresponding to heavy and light chain isotypes which are not utilized (according to the immunophenotyping results) by the patient's tumor serves as a convenient means to confirm the immunophenotyping results.

PCR primers utilized to clone variable regions of the patient's tumor-specific Ig are summarized below in Tables 1 through 3:

TABLE 1

Heavy Chain Primers:

| | | |
|---|---|---|
| VH1L | 5'-TCT AGA ATT CAC GCG TGG ACC ATG GAC TGG ACC TGG AG-3' | SEQ ID NO:52 |
| VH2L | 5'-TCT AGA ATT CAC GCG TCC ACC ATG GAC ACA CTT TGC TAC AC-3' | SEQ ID NO:53 |
| VH3L | 5'-TCT AGA ATT CAC GCG TCC ACC ATG GAG TTT GGG CTG AGC TGG-3' | SEQ ID NO:54 |
| VH4L | 5'-TCT AGA ATT CAC GCG TCC ACC ATG AAA CAC CTG TGG TTC TTC CT-3' | SEQ ID NO:55 |
| VH5L | 5'-TCT AGA ATT CAC GCG TCC ACC ATG GGG TCA ACC GCC ATC CT-3' | SEQ ID NO:56 |
| VH6L | 5'-TCT AGA ATT CAC GCG TCC ACC ATG TCT GTC TCC TTC CTC ATC TT-3' | SEQ ID NO:57 |
| C$_\gamma$ | 5'-GCG TGA GTT CCA CGA CAC CGT CAC-3' | SEQ ID NO:58 |
| C$_\mu$ | 5'-GGG GAA AAG GGT TGG GGC GGA TGC-3' | SEQ ID NO:59 |
| JH1245 | 5'-GAG GGG CCC TTG GTC GAC GCT GAG GAG ACG GTG ACC AGG-3' | SEQ ID NO:60 |
| JH3 | 5'-GAG GGG CCC TTG GTC GAC GCT GAA GAG ACG GTG ACC ATT G-3' | SEQ ID NO:61 |
| JH6 | 5'-GAG GGG CCC TTG GTC GAC GCT GAG GAG ACG GTG ACC GTG-3' | SEQ ID NO:62 |

TABLE 2

Kappa Chain Primers:

| | | |
|---|---|---|
| VKI | 5'-TCT AGA ATT CAC GCG TCC ACC ATGGAC ATG AGG GTC CCC GCT CAG-3' | SEQ ID NO:63 |
| VKκIV | 5'-TCT AGA ATT CAC GCG TCC ACC ATG AGG CTC CCT GCT CAG C-3' | SEQ ID NO:64 |
| VκIII | 5'-TCT AGA ATT CAC GCG TCC ACC ATG GAA GCC CCA GCG CAG CTT-3' | SEQ ID NO:65 |
| VκIV | 5'-TCT AGA ATT CAC GCG TCC ACC ATG GTG TTG CAG ACC CAG GT-3' | SEQ ID NO:66 |
| VκV | 5'-TCT AGA ATT CAC GCG TCC ACC ATG GGG TCC CAG GTT CAG GT-3' | SEQ ID NO:67 |
| VκVIa | 5'-TCT AGA ATT CAC GCG TCC ACC ATG TTG CCA TCA CAA CTC ATT G-3' | SEQ ID NO:68 |
| VκVIb | 5'-TCT AGA ATT CAC GCG TCC ACC ATG GTG TCC CCGTGG CAA U-3' | SEQ ID NO:69 |
| Cκ | 5'-GGT TCC GGA CTT AAG CTG CTC ATC AGA TGG CGG G-3' | SEQ ID NO:70 |

TABLE 3

Lambda Chain Primers:

| | | |
|---|---|---|
| VL1 | 5'-TCT AGA ATT CAC GCG TCC ACC ATG GCC TGCTCT CCT CTC CTC CT-3' | SEQ ID NO:71 |
| VL2 | 5'-TCT AGA ATT CAC GCG TCC ACC ATG GCC TGG GCT CTG CTG CTC GT-3' | SEQ ID NO:72 |
| VL3 | 5'-TCT AGA ATT CAC GCG TCC ACC ATG GCC TGG ATC CTT CTC CTC CTC-3' | SEQ ID NO:73 |
| VL4 | 5'-TCT AGA ATT CAC GCG TCC ACC ATG GCC TGG ACC CCT CTC TGG CTC-3' | SEQ ID NO:74 |
| VL6 | 5'-TCT AGA ATT CAC GCG TCC ACC ATG GCC TGG GCC CCA CTA CT-3' | SEQ ID NO:75 |
| VL8 | 5'-TCT AGA ATT CAC GCG TCC ACC ATG GCC TGG ATG ATG CTT CTC CT-3' | SEQ ID NO:76 |
| Cλ | 5'-GGC GCC GCC TTG GGC TGA CCT AGG ACG GT-3' | SEQ ID NO:77 |

The VH1-6L primers contain recognition sites for XbaI, EcoRI and MluI at their 5' ends. The three JH primers contain recognition sites for ApaI and SalI at their 5' ends. The seven Vκ primers contain recognition sites for XbaI, EcoRI and MluI at their 5' ends. The Cκ primer contains recognition sites for BspEI and AflIII at the 5' end. The six VL primers contain recognition sites for XbaI, EcoRI and MluI at their 5' ends. The Cλ primer contains recognition sites for KasI and AvrII at the 5' end.

For each tumor sample, five $V_H$ PCR reactions are run. Each $V_H$ reaction will contain the Cμ and Cγ primers. The Cμ primer (SEQ ID NO:59) should result in ~590 bp product for the heavy chain V ($V_H$) region expressed in an IgM positive tumor. The Cγ primer (SEQ ID NO:58) should result in ~480 bp product for the heavy chain V region expressed in an IgG positive tumor. The VH1, VH2, VH3, and VH4 primers (SEQ ID NOS: 52-55, respectively) are used in separate PCR reactions and the VH5 and VH6 primers (SEQ ID NOS:56 and 57, respectively) are used together in the same reaction. The $V_H$ primer(s), which when used in connection with a $C_H$ region primer, gives a PCR product of the expected size is then be used in three separate PCR reactions containing either the JH1245, JH3 or JH6 primers (SEQ ID NOS:60-62, respectively) to generate a PCR product corresponding to the variable (V), diversity (D) and joining (J) regions present in the Ig(s) expressed by the patient's tumor. The VDJ reaction product is then subcloned into the pSRαSD9CG3C vector or pSRαSD9CG4C vector using the 5' XbaI, EcoRI or MluI sites and the 3' SalI or ApaI sites to provide an expression vector encoding the patient's heavy chain variable domain linked to either a γ3 or γ4 constant domain. As is understood by those in the art, the PCR product is subcloned into the expression vector using restriction enzymes which lack sites internal to the PCR product (i.e., within the Ig sequences). The PCR products are digested with restriction enzymes that have sites located within the PCR primers to confirm that the PCR product lacks an internal site for a given restriction enzyme prior to subcloning the PCR product into the desired expression vector. It is anticipated that the 5' MluI site can be employed for each PCR product given that MluI sites are very infrequently found in the genome; however the 5' primers also contain XbaI and EcoRI sites in the event a particular PCR product contains an internal MluI site. The following restriction enzymes (which have recognition sites in the above-described 3' PCR primers) are examined first for their inability to cut internally to the PCR products: SalI for heavy chain PCR products; AflII for kappa light chain PCR products; AvrII for lambda light chain PCR products. As discussed above, each 3' PCR primer provides alternative restriction enzyme sites.

With regard to choosing an expression vector, the pSRαSD9CG3C vector is initially chosen as Cγ3 is the least frequently used isotype in humans (Cγ4 is the next least frequently utilized isotype, with Cγ1 and Cγ2 being the most frequently used isotypes) and therefore ELISAs performed following immunization with a vaccine comprising Cγ3 are easier to conduct and interpret as the patient's anti-idiotype response will mainly consist of the γ1 and γ2 isotypes. However, Cγ4 may be chosen over Cγ3 if a given Cγ3 construct produces an Ig protein which tends to fall out of solution upon purification.

For each tumor sample, five Vκ PCR reactions are run. Each Vκ PCR reaction will contain the Cκ primer (SEQ ID NO:70). The VκI, VκII, and VκIII primers (SEQ ID NOS:63-65, respectively) will be run in separate reactions. The VκIV and VκV primers (SEQ ID NOS:66 and 67, respectively) are combined in one PCR reaction and the VκVIa and VκVIb primers (SEQ ID NOS:68 and 69, respectively) in another. The PCR reaction which yields a PCR product of the expected size (~480 bp) is used as the source of DNA encoding the variable domain derived from the light chain of the patient's Ig. The positive reaction product is subcloned into the pSRαSD9CKC vector using the 5' XbaI, EcoRI or MluI sites and the 3' AflII or BspEI sites.

For each tumor sample, six Vλ PCR reactions are run. Each Vκ PCR reaction will contain the Cλ primer (SEQ ID NO:77). The VL1, VL2, VL3, VL4, VL6 and VL8 primers (SEQ ID NOS:71-76, respectively) are used in separate reactions. The PCR reaction which yields a PCR product of the expected size (~420 bp) is used as the source of DNA encoding the variable domain derived from the light chain of the patient's Ig. The positive reaction product will be subcloned into the pSRαSD9CL2C vector using the 5' XbaI, EcoRI or MluI sites and the 3' AvrII or KasI sites. It is understood by those skilled in the art that the tumor cells will express either a κ or a λ light chain. Therefore, it is expected that a PCR product will be recovered from either the Vκ or Vλ PCRs but not from both.

e) Expression and Amplification of Tumor-Specific Ig in Mammalian Cells

Once expression vectors containing sequences derived from the variable regions of the heavy and light chains found in the patient's tumor are constructed, these plasmids are used to transform *E. coli* using conventional techniques. Between 18 and 24 colonies from each subcloning are screened for heavy and light chain inserts as appropriate by restriction enzyme analysis of miniprep DNA (from 1-1.5 ml cultures). Equal aliquots of the positive subclones are used to inoculate larger cultures (~250 mls) from which the DNA for electroporation is prepared. This allows for the isolation of the somatic variants in the tumor population and result in transfectants (e.g., BW5147.G.1.4 transfectants) expressing these somatic variants.

To further define the presence of somatic variants, 20 μl PCR reactions are run using ~100 pg of each miniprep DNA and the appropriate V region and C region primers. Digestion of the resulting PCR products with several four base recognition restriction enzymes allows the differentiation of somatic variants. In addition, DNA sequencing can be performed on individual subclones to demonstrate the presence of somatic variants within the pool of subclones containing the cloned heavy and light chain variable regions.

Plasmids encoding the chimeric heavy and light chains derived from the patient's Ig are electroporated along with pM-HPRT-SSD9-DHFR into BW5147.G.1.4 cells as follows. The Ig expression plasmids (which comprise a mixture of vectors containing the somatic variants found within the tumor Ig) are linearized by digestion with AscI or PacI. pM-HPRT-SSD9-DHFR is linearized with AscI or PacI. pM-HPRT-SSD9-DHFR and the Ig expression plasmids are used at a ratio of 1:20-50. Approximately 15 μg of pM-HPRT-SSD9-DHFR (10-20 μg) is used while a total of ~500 μg of the expression vectors are used. The linearized plasmids are digested, precipitated and resuspended in 0.5 ml electroporation buffer [i.e., 1×HBS(EP)] as described in Example 7. The linearized plasmids in 0.5 ml electroporation buffer are mixed with $2 \times 10^7$ cells (e.g., BW5147.G.1.4) in 0.5 ml electroporation buffer and electroporated as described in Example 7. The cells are then grown in selective medium followed by growth in medium containing MTX as described in Examples 7 and 8. Clones which grow in the selective medium are checked for the ability to express the cloned Ig proteins using standard methods (e.g., by ELISA). Primary selectants expressing high levels of the cloned Ig proteins are then grown in medium containing MTX as described in Examples 7 and 8 to amplify the transfected genes. The presence of the selectable and amplifiable markers on a single piece of DNA (i.e., pM-HPRT-SSD9-DHFR), obviates concerns that primary transfectants (i.e., cells capable of growing in medium containing Hx and Az) which express the genes of interest (i.e., the Ig proteins) at high levels have failed to integrate a DHFR gene.

f) Purification of Tumor-Specific Ig from Amplified Cell Lines

The tumor-specific Ig expressed by the amplified cell lines (using either the pSRαSD9CG3C or pSRαSD9CG4C vectors) is purified by chromatography of culture supernatants on Protein G Sepharose (Pharmacia); Protein G binds to both $IgG_3$ and $IgG_4$. The chromatography is conducted according to the manufacturer's instructions. When the tumor-specific Ig is produced using the pSRαSD9CG4C vector, Protein A Sepharose (Pharmacia) may also be employed for purification.

g) Administration of Tumor-Specific Ig (Multivalent Vaccine)

The purified tumor immunoglobulin-idiotype protein may be conjugated to a protein carrier such as keyhole limpet hemocyanin (KLH) (Calbiochem, San Diego, Calif.) prior to administration to the patient. If the immunoglobulin-idiotype protein is to be conjugated with KLH, the KLH is depleted of endotoxin using methods known to the art [Kwak et al. (1992), supra]. For example, the KLH is applied to a QAE Zeta Prep 15 disk (LKB, Broma, Sweeden) to produce a preparation of KLH containing less than 1000 endotoxin units per milliliter. Equal volumes of filter sterilized purified KLH and purified immunoglobulin-idiotype protein (each at 1 mg/ml) are mixed together. Sterile glutaraldehyde is added at a final concentration of 0.1%. The Ig-KLH conjugate is then dialyzed extensively against physiologic saline to remove excess glutaraldehyde.

Purified immunoglobulin-idiotype protein (conjugated or unconjugated) is mixed with an immunologic adjuvant such as SAF-1 (Syntex adjuvant formulation 1; Roche) or other adjuvant presently or subsequently approved for administration to humans [e.g., QS-21 (PerImmune, Inc., Rockville, Md.)]. The purified immunoglobulin-idiotype protein is emulsified in the desired adjuvant and injected subcutaneously at 0, 2, 6, 10 and 14 weeks. Booster injects may be given at 24 and 28 weeks. Each injection contains 0.5 mg of purified, tumor-specific idiotype immunoglobulin (which may be conjugated 1:1 with KLH).

An alternative to the use of KLH as a foreign carrier protein to boost the immune response to the immunoglobulin idiotype protein is the use of a fusion protein comprising idiotype protein and a cytokine (e.g., GM-CSF, IL-2 or IL-4) [PCT International Application PCT/US93/09895, Publication No. WO 94/08601 and Tao and Levy (1993) Nature 362:755 and Chen et al. (1994) J. Immunol. 153:4775]. In these fusion proteins, sequences encoding the desired cytokine are added to the 3' end of sequences encoding the immunoglobulin idiotype protein. The present invention contemplates the use of idiotype-cytokine fusion proteins for the treatment of B-cell lymphoma. The sequences encoding the heavy chain of the patient's immunoglobulin protein are cloned as described above and inserted into an expression vector containing sequences encoding the desired cytokine such that a fusion protein comprising, from amino- to carboxy-terminus, the heavy chain of the patient's tumor-specific immunoglobulin and the desired cytokine.

An alternative to the use of foreign carrier proteins, cytokines, or immunologic adjuvants is the use of autologous dendritic cells pulsed with the purified immunoglobulin-idiotype protein [see for example, Hsu et al. (1996), supra and PCT International Application PCT/US91/01683, Publication No. WO 91/13632]. Methods for the isolation of human dendritic cells from peripheral blood are known to the art [Mehta et al. (1994) J. Immunol. 153:996 and Takamizawa et al. (1995) J. Clin. Invest. 95:296]. Briefly, the patient is leukapheresed using a cell separator (COBE). Peripheral blood mononuclear cells (PBMCs) are collected by separation through Ficoll-Hypaque (Pharmacia). Monocytes are then removed by centrifugation through discontinuous Percoll (Pharmacia) gradients. The monocyte-depleted PBMCs are then placed in medium (RPMI 1640 containing 10% autologous patient serum) containing idiotype protein (2 µg/ml). Following incubation for 24 hours at 37° C. in a humidified atmosphere containing 10% $CO_2$, the dendritic cells are separated from lymphocytes by sequential centrifugation through 15% and 14% (wt/vol) metrizamide gradients. The preparation is then incubated for 14-18 hours in medium containing 50 µg/ml idiotype protein. The cells are then washed to remove free antigen (i.e., idiotype protein) and placed in sterile saline containing 5% autologous serum and administered intravenously.

Each patient is followed to determine the production of idiotype-specific antibody; the in vitro proliferative responses (to KLH, if used, and to immunoglobulin idiotype using 0 to 100 µg of soluble protein per milliliter in 5 day in vitro cultures) of PBMCs isolated from the treated patients may also be determined. These assays are conducted immediately before each immunization and 1 to 2 months following the last immunization. Patients are monitored for disease activity by physical examination, routine laboratory studies and routine radiographic studies. Regression of lymph nodes or cutaneous lymphomatous masses may be confirmed by computed tomography (CT). In addition, residual disease may be measured using a tumor-specific CDR3 analysis as described by Hsu et al. (1996), supra.

h) Treatment of T-cell Tumors

Vaccines comprising soluble T cell receptor (TCR) proteins derived from a patient's T cell tumor (i.e., a T cell leukemia or lymphoma) are produced using the methods described in Example 9 with the exception that pM-HPRT-SSD9-DHFR is used in place of separate selection and amplification vectors as described above. The thrombin solubilized TCR proteins are purified by chromatography on a resin comprising a monoclonal antibody (mcab) directed against a monomorphic determinant on human αβ TCRs [e.g., mcab T10B9.1A-31 (Pharmingen, San Diego, Calif.); mcab BMA031 (Immunotech, Westbrook, Me.); mcabs BW242/412, 8A3 or 3A8 (Serotec, Washington, D.C.). Antibodies directed against monomorphic (i.e., invariant) determinants on TCRs recognize all αβ TCRs.

The purified tumor-specific idiotype TCR protein is administered as described above for the purified tumor-specific idiotype Ig protein (i.e., mixing with an immunologic adjuvant, conjugation to a protein carrier, the use of TCR-cytokine fusion proteins, the use of dendritic cells pulsed with the purified TCR protein such as SAF-1, etc.). Patients are followed to determine the production of idiotype-specific antibody as described above. Patients are monitored for disease activity by physical examination, routine laboratory studies and routine radiographic studies.

From the above, it is clear that the present invention provides improved methods for the amplification and expression of recombinant genes in cells. The resulting amplified cell lines provide large quantities of recombinant proteins in a short period of time. The ability to produce large quantities of recombinant proteins in a short period of time is particularly advantageous when proteins unique to a patient's tumors are to be used for therapeutic purposes, such as for vaccination.

All publications and patents mentioned in the above specification are herein incorporated by reference. Various modifications and variations of the described method and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

I claim:
1. A cell expressing a multivalent composition, said multivalent composition for active idiotype immunotherapy, said cell produced according to a method comprising:
   a) providing:
      i) malignant B cells isolated from a patient having a quasi-clonal B-cell lymphoma;
      ii) at least one expression vector;
      iii) an amplification vector comprising a recombinant oligonucleotide having a sequence encoding a first inhibitable enzyme operably linked to a heterologous promoter; and
      iv) a T lymphoid parent cell line;
   b) isolating nucleic acid from said malignant cells, said nucleic acid comprising nucleotide sequences selected from the group consisting of nucleotide sequences encoding at least one $V_H$ region and at least two $V_L$ regions, nucleotide sequences encoding at least two $V_H$ regions and at least one $V_L$ region, and nucleotide sequences encoding at least two $V_H$ regions and at least two $V_L$ regions, wherein said at least two $V_L$ regions differ by at least one idiotope, wherein said at least two $V_H$ regions differ by at least one idiotope, and wherein said $V_H$ and $V_L$ regions are derived from immunoglobulin molecules expressed by said malignant cells;
   c) inserting said nucleic acid comprising nucleotide sequences encoding said $V_H$ and $V_L$ regions into said at least one expression vector;
   d) introducing said at least one expression vector and said amplification vector into said parent cell line to generate one or more transformed cells;
   e) growing said transformed cells in a first aqueous solution containing an inhibitor capable of inhibiting said first inhibitable enzyme wherein the concentration of said inhibitor present in said first aqueous solution is sufficient to prevent growth of said parent cell line; and
   f) identifying a transformed cell capable of growth in said first aqueous solution, wherein said transformed cell capable of growth expresses a combination of $V_H$ and $V_L$ regions selected from the group consisting of at least one $V_H$ region and at least two $V_L$ regions, at least two $V_H$ regions and at least one $V_L$ region, and at least two $V_H$ regions and at least two $V_L$ regions, wherein said at least two $V_L$ regions differ by at least one idiotope, wherein said at least two $V_H$ regions differ by at least one idiotope, and wherein said $V_H$ and $V_L$ regions comprise a protein molecule,
   wherein said multivalent composition comprises said expressed $V_H$ and $V_L$ regions.

2. The composition of claim 1, wherein nucleotide sequences encoding said $V_H$ and $V_L$ regions comprise at least two $V_H$ and at least one $V_L$ regions.

3. The composition of claim 1, wherein nucleotide sequences encoding said $V_H$ and $V_L$ regions comprise at least one $V_H$ and at least two $V_L$ regions.

4. A cell expressing a multivalent composition, said multivalent composition for active idiotype immunotherapy, said cell produced according to a method comprising:
   a) providing:
      i) malignant B cells isolated from a patient having a quasi-clonal B-cell lymphoma;
      ii) at least one expression vector;
      iii) an amplification vector comprising a first recombinant oligonucleotide having a sequence encoding a first inhibitable enzyme operably linked to a heterologous promoter;
      iv) a selection vector comprising a second recombinant oligonucleotide having a sequence which encodes a selectable gene product; and
      v) a T lymphoid parent cell line;
   b) isolating nucleic acid from said malignant cells, said nucleic acid comprising nucleotide sequences selected from the group consisting of nucleotide sequences encoding at least one $V_H$ region and at least two $V_L$ regions, nucleotide sequences encoding at least two $V_H$ regions and at least one $V_L$ region, and nucleotide sequences encoding at least two $V_H$ regions and at least two $V_L$ regions, wherein said at least two $V_L$ regions differ by at least one idiotope, wherein said at least two $V_H$ regions differ by at least one idiotope, and wherein said $V_H$ and $V_L$ regions are derived from immunoglobulin molecules expressed by said malignant cells;
   c) inserting said nucleic acid comprising said nucleotide sequences encoding said $V_H$ and $V_L$ regions into said at least one expression vector;
   d) introducing said at least one expression vector, said amplification vector and said selection vector into said parent cell line to generate transformed cells;
   e) introducing said transformed cells into a first aqueous solution, said first aqueous solution requiring the expression of said selectable gene product for growth of said transformed cells;
   f) identifying at least one transformed cell capable of growth in said first aqueous solution;
   g) introducing said transformed cell capable of growth in said first aqueous solution into a second aqueous solution, said second aqueous solution comprising an inhibitor capable of inhibiting said first inhibitable enzyme, wherein the concentration of said inhibitor present in said second aqueous solution is sufficient to prevent growth of said parent cell line; and
   h) identifying at least one transformed cell capable of growth in said second aqueous solution, wherein said transformed cell capable of growth expresses a combination of $V_H$ and $V_L$ regions selected from the group consisting of at least one $V_H$ region and at least two $V_L$ regions, at least two $V_H$ regions and at least one $V_L$ region, and at least two $V_H$ regions and at least two $V_L$ regions, wherein said at least two $V_L$ regions differ by at least one idiotope, wherein said at least two $V_H$ regions differ by at least one idiotope, and wherein said $V_H$ and $V_L$ regions comprise a protein molecule,
   wherein said multivalent composition comprises said expressed $V_H$ and $V_L$ regions.

5. A clone expressing a multivalent composition, said multivalent composition for active idiotype immunotherapy, said clone produced according to a method comprising:
   a) providing:
      i) malignant B cells isolated from a patient having a quasi-clonal B-cell lymphoma;
      ii) at least one expression vector;
      iii) an amplification vector comprising a first recombinant oligonucleotide having a sequence encoding a first inhibitable enzyme operably linked to a heterologous promoter;
      iv) a selection vector comprising a second recombinant oligonucleotide having a sequence which encodes a selectable gene product; and
      v) a T lymphoid parent cell line;
   b) isolating nucleic acid from said malignant cells, said nucleic acid comprising nucleotide sequences selected from the group consisting of nucleotide sequences encoding at least one $V_H$ region and at least two $V_L$ regions, nucleotide sequences encoding at least two $V_H$ regions and at least one $V_L$ region, and nucleotide sequences encoding at least two $V_H$ regions and at least two $V_L$ regions, wherein said at least two $V_L$ regions differ by at least one idiotope, wherein said at least two $V_H$ regions differ by at least one idiotope, and wherein said $V_H$ and $V_L$ regions are derived from immunoglobulin molecules expressed by said malignant cells;

c) inserting said nucleic acid comprising said nucleotide sequences encoding said $V_H$ and $V_L$ regions into said at least one expression vector;

d) introducing said at least one expression vector, said amplification vector and said selection vector into said parent cell line to generate transformed cells;

e) introducing said transformed cells into a first aqueous solution, said first aqueous solution requiring the expression of said selectable gene product for growth of said transformed cells;

f) identifying at least one individual clone of transformed cells capable of growth in said first aqueous solution;

g) introducing said individual clone capable of growth in said first aqueous solution into a second aqueous solution, said second aqueous solution comprising an inhibitor capable of inhibiting said first inhibitable enzyme, wherein the concentration of said inhibitor present in said first aqueous solution is sufficient to prevent growth of said parent cell line; and h) identifying at least one individual clone capable of growth in said second aqueous solution, wherein said clone capable of growth expresses a combination of $V_H$ and $V_L$ regions selected from the group consisting of at least one $V_H$ region and at least two $V_L$ regions, at least two $V_H$ regions and at least one $V_L$ region, and at least two $V_H$ regions and at least two $V_L$ regions, wherein said at least two $V_L$ regions differ by at least one idiotope, wherein said at least two $V_H$ regions differ by at least one idiotope, wherein said $V_H$ and $V_L$ regions comprise a protein molecule, wherein said multivalent composition comprises said expressed $V_H$ and $V_L$ regions.

* * * * *